US007824672B2

(12) United States Patent
Chaikof et al.

(10) Patent No.: US 7,824,672 B2
(45) Date of Patent: Nov. 2, 2010

(54) METHOD FOR COATING LIVING CELLS

(75) Inventors: Elliot L. Chaikof, Dunwoody, GA (US); Wanxing Cui, Norcross, GA (US); Zhifei Dai, Harbin (CN)

(73) Assignee: Emory University, Atlanta, GA (US)

( * ) Notice: Subject to any disclaimer, the term of this patent is extended or adjusted under 35 U.S.C. 154(b) by 952 days.

(21) Appl. No.: 11/091,939

(22) Filed: Mar. 28, 2005

(65) Prior Publication Data

US 2006/0002903 A1    Jan. 5, 2006

Related U.S. Application Data

(60) Provisional application No. 60/557,088, filed on Mar. 26, 2004.

(51) Int. Cl.
*A01N 63/00* (2006.01)
(52) U.S. Cl. .................................. 424/93.7; 435/325
(58) Field of Classification Search .................. None
See application file for complete search history.

(56) References Cited

U.S. PATENT DOCUMENTS

| | | | |
|---|---|---|---|
| 4,485,045 A | 11/1984 | Regen | |
| 4,522,803 A | 6/1985 | Lank et al. | |
| 4,560,599 A | 12/1985 | Regen | |
| 4,880,883 A | 11/1989 | Grasel et al. | |
| 4,906,465 A | 3/1990 | Chaikof et al. | |
| 5,071,532 A | 12/1991 | Taillet et al. | |
| 5,288,517 A | 2/1994 | Kanno et al. | |
| 5,399,331 A | 3/1995 | Loughrey et al. | |
| 5,417,969 A | 5/1995 | Hsu et al. | |
| 5,429,618 A | 7/1995 | Keogh | |
| 5,741,325 A | 4/1998 | Chaikof et al. | |
| 5,755,788 A | 5/1998 | Strauss | |
| 5,911,942 A | 6/1999 | Fofonoff et al. | |
| 6,071,532 A | 6/2000 | Chaikof et al. | |
| 6,171,614 B1 | 1/2001 | Chaikof et al. | |
| 6,583,251 B1 | 6/2003 | Chaikof et al. | |
| 6,699,952 B2 | 3/2004 | Chaikof et al. | |
| 6,936,298 B2 | 8/2005 | Chaikof et al. | |
| 2004/0063200 A1 | 4/2004 | Chaikof et al. | |
| 2004/0073295 A1 | 4/2004 | Chaikof et al. | |
| 2004/0110439 A1 | 6/2004 | Chaikof et al. | |
| 2004/0116677 A1 | 6/2004 | Chaikof et al. | |
| 2004/0171545 A1 | 9/2004 | Chaikof et al. | |
| 2005/0180945 A1 | 8/2005 | Chaikof et al. | |

FOREIGN PATENT DOCUMENTS

| WO | WO 96/21469 | 7/1996 |
|---|---|---|
| WO | WO 98/16198 | 4/1998 |
| WO | WO 00/00239 | 1/2000 |
| WO | WO 01/78800 | 10/2001 |
| WO | WO 01/80921 | 11/2001 |
| WO | WO 02/09647 | 2/2002 |
| WO | WO 02/055021 | 7/2002 |

OTHER PUBLICATIONS

Bunger et al. Biocompatibility and surface structure of chemically modified immunoisolating alginate-PLL capsules. J Biomed Mater Res A. Dec. 15, 2003;67(4):1219-1227.*
Akita et al. (1994) "Effect of FK506 and Anti-Cd4 Therapy on Fetal Pig Pancreas Xenografts and Host Lymphoid Cells in NOD/Lt, CBA, and BALB/c Mice," *Cell Transplantation* 3:61-73.
Anzai et al. (2000) "Constructon of Multilayer Thin Films Containing Avidin by a Layer-by-Layer Deposition of Avidin and Polu(anion)," *Langmuir* 16:6306-6311.
Anzai et al. (1999) "Layer-by-Layer Construction of Multilayer Thin Films Composed of Avidin and Biotin-Labeled Poly(amine)s," *Langmuir* 15:221-226.
Ao et al. (1995) "Microencapsulation Enhances Canine Islet Survival During Long-Term Culture," *Transplantation Proceedings* 27:3350.
Balamurugan et al. (2003) "Bioartificial Pancreas Transplantation at Prevascularized Intramuscular Space: Effect of Angiogenesis Induction on Islet Survival," *Pancreas* 26(3):279-285.
Beyer et al. (1996) "Covalently Attached Polymer Mono and Multilayers on Silanized Glass Substrates," *Thin Solid Films* 285:825-828.
Blankenburg et al. (1989) "Interaction Between Biotin Lipids and Streptavidin in Monolayers: Formation of Oriented Two-Dimensional Protein Domains Induced by Surface Recognition," *Biochem.* 28:8214-8221.
Blezer et al. (1998) "Initiation and Propagation of Blood Coagulation at Artificial surfaces Studied in a Capillary Flow Reactor," *Thromb. Haemost.* 79(2):296-301.
Cai et al. (1993) "A Solid-State NMR Study of Microphase Structure and Segmental Dynamics of Poly(styrene-b-methylphenylsiloxane) Diblock Copolymers," *Polymer* 34:267-276.
Calistri-Yeh et al. (1996) "Thermal Stability of Self Assembled Monolayers from Alkylchlorosilanes," *Langmuir* 12:2747-2755.
Cambell et al. (1994) "Biocompatible Surfaces Using Methacryloylphorylcholine Laurylmethacrylate Copolymer," *ASAIO J.* 40(3):M853-M857.
Chaikof, E.L. (1996) "Biomaterials that Imitate Cell Microenvironments," *Chemtech.* 26:17-24.
Chaikof, E.L. (1999) "Engineering and Materials Considerations in Islet Cell Transplantation," *Ann. Rev. Biomed. Eng.* 1:103-127.
Chaikof et al. (2002) "Microencapsulation Methods: Alginate-poly(L-lysine)," In; Atala et al Ed., *Methods of Tissue Engineering*, Academic Press, pp. 803-808.
Chapman, D. (1993) "Biomembranes and New Hemocompatible Materials," *Langmuir* 9:39-45.
Chen et al. (1997) "Phosphorylcholine Coating of ePTFE Grafts Reduces Neointimal Hyperplasmia in Canine Model," *Ann. Vasc. Surg.* 11(1):74-79.

(Continued)

*Primary Examiner*—Hope A Robinson
(74) *Attorney, Agent, or Firm*—Greenlee Sullivan P.C.

(57) ABSTRACT

The invention comprises anti-inflammatory conformal barriers with controllable permeability properties that can be applied to living cells prior to transplant, and methods for coating living cells with conformal barriers. The coatings comprise polymer layers deposited on a cell surface by layer-by-layer polymer assembly, wherein each layer contains a positive and a negative polymer pair. The barriers can be actively anti-inflammatory through incorporation of anticoagulant and/or anti-inflammatory agents into the barrier.

15 Claims, 27 Drawing Sheets

OTHER PUBLICATIONS

Cheung et al. (1994) "Molecular Self-Assembly of Conducting Polymers," *Thin Solid Films* 244:985-989.

Chen et al. (1996) "Studies on the Synthesis and Properties of Novel Phospholipid Analogous Polymers," *J. Appl. Polym. Sci.* 60:455-464.

Chon et al. (1999) "Cytomometic Biomaterials. 3. Preparation and Transport Studies of an Alginate/Amphiphilic Copolymer/Polymerized Phospholipid Film," *J. Biomater. Sci. Polymer. Ed.* 10:95-108.

Clayton et al. (1991) "The Effect of Capsule Composition on Biocompatibility on the Biocompatibility of Alginate-poly-l-lysine Capsules," *J. Microencapsulation* 8:221-233.

Colton et al. (1991) "Bioengineering in the Development of the Hybrid Artificial Pancreas," *J. Biochem. Eng.* 113:452-170.

Colton, C. (1992) "The Engineering of Xenogenic Islet Transplantation by Immunoisolation," *Diab. Nutr. Metabol.* 5:145-149.

Conboy et al. (2003) "Planar Supported Bilayer Polymers Formed from Bis-diene Lipids by Langmuir-Blodgett Deposition and UV Irradiation," *Biomacromolecules* 4:841-849.

Contreras et al. (2002) "Cytoprotection of Pancreatic Islets Before and Early After Transplantation Using Gene Therapy," *Kidney Int.* 61(Supp 1):79-84.

Crooks et al. (1990) "Microencapsulation of Mammalian Cells in a HEMA-MMA Copolymer: Effect on Capsule Morphology and Permeability," *J. Biomed. Mater. Res.* 24:1241-1262.

Cruise et al. (1998) "A Sensitivity Study of the Key Parameters in the Interfacial Photolopymerization of Poly(ethylene glycol) Diacrylate Upon Porcine Islets," *Biotechnol. Bioeng.* 57:655-665.

Cruise et al. (1999) "In Vitro and in Vivo Performance of Porcine Islets Encapsulated in Interfacially Photopolymerized Poly(ethylene glycol) Diacrylate Membranes," *Cell. Transplant* 8(3):293-309.

Cui et al. (2003) "A Novel Approach for Islet Encapsulation with Bio-Membrane Mimetic System," *Transplantation* 76:146.

Dai et al. (2001) "Novel Encapsulated Functional Dye Particles Based on Alternately Adsorbed Multi-Layers of Active Oppositely Charged Macromolecular Species," *Macromol. Rapid Commun.* 22:756-762.

Dai et al. (2002) "Downhill Energy Transfer of Multichromophores in Layer-by-Layer Self-Assembling Light-Harvesting Capsules," *J. Phys. Chem. B* 106:11501-11508.

Dai et al. (2002) "Highly Stable and Biocompatible Nafion-Based Capsules With Controlled Permeability for Low Molecular Species," *Chem. Eur. J.* 8:4751-4755.

Dai et al. (2001) "Layer-by-Layer Self-Assembly of Polyeletrolyte and Low Molecular Weight into Capsules," *Adv. Mater.* 13:1339-1342.

Dai et al. (2002) "Nanoengineering of Polymeric Capsules with a Shell-in-Shell Structure," *Langmuir* 18:9533-9538.

Dai et al. (2002) "Novel Capsules with High Stability and Controlled Permeability by Hierarchic Templating," *Chem. Int Ed.* 41:4019-4022.

Dai et al. (2002) "Mimicking Photosynthetic Two-Step Energy Transfer in Cyanine Triads Assembled into Capsules," *Langmuir* 18:4553-4555.

Decher, G. (1997) "Fuzzy Nanoassemblies: Toward Layered Polymeric Multicomposites," *Science* 277:1232-1237.

Dokoutchaev et al. (1999) "Colloidal Metal Deposition onto Functionalized Polystyrene Microsheres," *Chem. Mater.* 11:2389-2399.

Donath et al. (1998) "Novel Hollow Polymer Shells by Colloid-Templated Assembly of Polyelectrolytes," *Angew. Chem. Int. Ed.* 37:2201-2205.

Edmiston et al. (1998) "Molecular Oriented Distributions in Protein Films. 4. A Multilayer Composed of Yeast Cytochrome *c* Bound through an Intermediate Streptavidin Layer to a Planar Supported Phospholipid Bilayer," *J. Am. Chem. Soc.* 120:1665-1671.

Elbert et al. (1999) "Thin Polymer Layers Formed By Polyelectrlyte Multilayer Techniques on Biological Surfaces," *Langmuir* 15:5355-5362.

Elbert et al. (1998) "Self-Assembly and Steric Stabilization at Heterogeneous, Biological Surfaces Using Adsorbing Block Copolymers," *Chem. Biol.* 5:177-183.

Elender, G. et al. (1996) "Fictionalization of Si/SiO$_2$ and Glass Surfaces with Ultrathin Dextran Films and Deposition of Lipid Bilayers," *E. Biosensors Bioelectronics* 11:565-577.

Faucher et al. (2003) "Fabrication and Characterization of Glycocalyx-Mimetic Surfaces," *Langmuir* 19:1664-1670.

Feng et al. (2002) "Functional Reconstruction of Thrombomodulin Within a Substrate Supported Membrane-Mimetic Polymer Film," *Langmuir* 2002;18:9907-0013.

Feng et al. (2000) "Reconstitution of Thrombomodulin into Polymerizable Phospholipid Vesicles," *Polymer Preprints* 41:1653-1654.

Florin et al. (1993) "Painted Supported Lipid Membranes," *Biophys J.* 64:375-383.

Gnanou et al. (1998) "Synthesis of Star-Shaped Poly(ethylene oxide)," *Macromol. Chem.* 189:2885-2892.

Gomi et al. (1990) "Antithrombotic Effect of Recombinant Human Thrombomodulin on Thrombin-Induced Thromboembolism in Mice," Blood 75(7):1396-1399.

Goeden-Wood et al. (2002) "Improved Assembly of Multimeric Genes for the Biosynthetic Production of Protein Polymers," *Biomacromolecules.* 3(4):874-879.

Golden, M.A. (1990) "Healing of Polytetrafluoroethylene Arterial Grafts is Influenced by Graft Porosity," *J. Vascular Surgery* 11(6):838-844.

Goldsmith et al. (1986) "Rheological Aspects of Thrombosis and Haemostasis: Basic Principles and Applications," *Thromb. Haemostasis* 55(3):415-435.

Goosen, M.F.A. (1985), "Optimization of Microencapsulation Parameters: Semipermeable Microcapsules as a Bioartificial Pancreas," *Biotech. Bioeng.* 27:146-150.

Goosen et al. (1980) "Inactivation of Thrombin by Antithrombin III on a Heparinized Biomaterial," *Thrombisis Research* 20(5/6):543-554.

Grande et al. (2001) "Glycosaminoglycan Mimetic Biomaterials. 2. Alkene- and Acrylate-Derivatized Glycopolymers via Cyanoxyl-Mediated Free-Radical Polymerization," *Macromolecules* 34:1640-1646 (tentatively published on Web Feb. 13, 2001).

Grande et al. (2000) "Glycosaminoglycan Mimetic Biomaterials. 1. Nonsulfated and Sulfated Glycopolymers by Cyanoxyl-Mediated Free-Radical Polymerization," *Macromolecules* 33:1123-1125.

Grande et al. (2000) "Synthesis of Non-Sulfated and Sulfated Glycopolymers," *Polymer Preprints* 41(1):1000-1001.

Hall et al. (1989) "Biomembranes as Models for Polymer Surfaces," *Biomaterials* 10(4):219-224.

Halle et al. (1993) "Protection of Islets of Langerhans from Antibodies by Microencapsulation with Alginate-poly-L-lysine Membranes," *Transplantation,* 44:350-4.

Hayward et al. (1986) "Biomembranes as Models for Polymer Surfaces," *Biomaterials* 7:252-258.

Hayward et al. (1984) "Biomembrane Surfaces as Models for Polymer Design: The Potential for Haemocompatibility," *Biomaterials* 5:135-142.

Herron et al. (1992) "Specific Recognition-Induced Self-Assembly of a Biotin Lipid/Streptavidin/Fab Fragment Triple Layer at the Air/Water Interface: Ellipsometric and Fluorescence Microscopy Investigations," *Langmuir* 8:1413-1416.

Hill et al. (1997) "Immunoisolation of Adult Porcine Islets for the Treatment of Diabetes Mellitus. The Use of Photopolymerizable Polythylene Glycol in the Conformal Coating of Mass-Isolated Porcine Islets," *Ann. N.Y. Acad Sci.* 831:332-343.

Holland et al. (1998) "Biomimetic Engineering of Non-Adhesive Glycocalyx-Like Surfaces Using Oligosaccharide Surfactant Polymers," *Nature* 392:799-801.

Hou et al. (2003) "Synthesis of Water-Soluble Star-Block and Dendrimer-Like Copolymers Based on Poly(ethylene oxide) and Poly(acrylic acid)," *Macromol.* 36:3874-3881.

Ishihara, K. (1997) "Novel Polymeric Materials for Obtaining Blood-Compatible Surfaces," *TRIP* 5(12):401-407.

Ishihara et al. (1995) "Synthesis of Phospholipid Polymers Having a Urethane Bond in the Side Chain as Coating Material on Segmented Polyurethane and Their Platelet Adhesion-Resistant Properties," *Biomaterials* 16:873-879.

Kaneider et al. (2002) "Reversal of Thrombin-Induced Deactivation of CD39/ATPDase in Endothelial Cells by HMG-CoA Reductase Inhibition: Effects on Rho-GTPase and Adenosine Nucleotide Metabolism," *Arterioscler Thromb. Vasc. Biol.* 22(6):894-900.

Keller et al. (1995) "Photoinduced charge Separation in Multilayer Thin Films Grown by Sequential Adsorption of Polyelectrolytes," *J. Am. Chem. Soc.* 117:12879-12880.

Keuren et al. (2003) "Thrombogenicity of Polysaccharide-Coated Surfaces," *Biomaterials* 24:1917-1924.

Kim et al. (2000) "The Influence of Tiered Layers of Surface-Grafted Poly(ethylene glycol) on Receptor-Ligand-Mediated Adhesion Between Phospholipid Monolayer-Stabilized Microbubbles and Coated Glass Beads," *Langmuir* 16:2808-2817.

King et al. (1987) "Alginate-Polylysine Microcapsules of Controlled Membrane Molecular Weight Cutoff for Mammalian Cell Culture Engineering," *Biotech Progress* 3:231-240.

Kishida et al. (1994) "Immobilization of Human Thrombomodulin Onto Biomaterials," *ASAIO Journal* 40(3):M840-845.

Kishida et al. (1994) "Immobilization of Human Thrombomodulin on Biomaterials: Evaluation of the Activity of Immobilized Human Thrombomodulin," *Biomaterials* 15(14):1170-1174.

Kishida et al. (1994) "Immobilization of Human Thrombomodulin Onto Poly(ether urethane urea) for Developing Antithrombogenic Blood-Contacting Materials," *Biomaterials* 15(10):848-852.

Korbutt et al. (1995) "Successful Reversal of Diabetes in Nude Mice by Transplantation of Microencapsulated Porcine Neonatal islet Cell Aggregates," *Transplantation Proceedings* 27:3212.

Kühner et al. (1994) "Lipid Mono- and Bilayer Supported on Polymer Films: Composite Polymer-Lipid Films on Solid Substrates," *E. Biophys. J.* 67:217-226.

Lim et al. (1980) "Microencapsulated Islets as a Bioartificial Endocrine Pancreas," *Science* 210:908-910.

Linden J. (2001) "Molecular Approach to Adenosine Receptors: Receptor-Mediated Mechanisms of Tissue Protection," *Annu. Rev Pharmacol Toxicol* 41:775-787.

Lindhout et al. (1995) "Antithrombin Activity of Surface-Bound Heparin Studied Under Flow Conditions," *J. Biomed. Mater. Res.* 29(10):1255-1266.

Liu et al. (2002) "Generation of a Photopolymerized Membrane Mimetic Monolayer on an Alginate/poly-L-lysine Coacervate," *Polymer Preprints* 41:1036-37.

Liu et al. (2002) "A Membrane-Mimetic Barrier for Cell Encapsulation," *Langmuir* 18:1332-1339.

Loudovaris et al. (1992) "The Role of T Cells in the Destruction of Xenografts Within Cell Impermeable Membranes," *Transplantation Proceedings* 24:2938.

Lvov et al. (1993) "Assembly, Structural Characterization, and Thermal Behavior of Layer-By-Layer Deposited Ultrathin Films of Poly(vinyl sulfate) and Poly(allylamine)," *Langmuir* 9:481-486.

Mahal et al. (1997) Engineering Chemical Reactivity on Cell Surfaces Through Oligosaccharide Biosynthesis. *Science* 276:1125-1128.

Maoz et al. (1984) "On the Formation and Structure of Self-Assembling Monolayers," *J. Colloid Interface Sci.* 100(2):456.

Marra et al. (1997) "Cytomimetic Biomaterials. 1. In-Situ Polymerization of Phospholipids on an Alkylated Surface," *Macromolecules* 30:6483-6488.

Marra et al. (1997) "Cytomimetic Biomaterials. 2. In-Situ Polymerization of Phospholipids on a Polymer Surface," *Langmuir* 13:5697-5701.

Marra et al. (1997) "Stabilized Phosphatidylcholine Surfaces via in-situ Polymerization at a Solid-Liquid Interface," *Polymer Preprints* 38(2):682-683.

Mauk et al. (1998) "Structural Characterization of Self-Assembled Lipid Monolayers by $N\pi T$ Simulation," *Langmuir* 14:5255-5266.

Moya et al. (2000) "Lipid Coating on Polyelectrolyte Surface Modified Colloidal Particles and Polyelectrolyte Capsules," *Macromolecules* 33:4538-4544.

Nah et al. (2000) "Polymeric Micelle Formation of Multiblock Copolymer Composed of Poly(γ-benzyl L-glutamate) and Poly(ethylene oxide)," *Bull. Korean Chem. Soc.* 21(4):383-388.

Nah et al. (2000) "Drug-Delivery System Based on Core-Shell-Type Nanoparticles Composed of Poly(γ-benzyl L-glutamate) and Poly(ethylene oxide)," *J. App. Polymer Sci.* 75:115-1126.

O'Brien et al. (1998) "Polymerization of Preformed Self-Organized Assemblies," *Acc. Chem. Res.* 31:861-868.

Perez-Salas et al. (2003) "Characterization of a Biomimetic Polymeric Lipid Bilayer by Phase Sensitive Neutron Reflectometry," *Langmuir* 19:7688-7694.

Plant, A. L., (1993) "Self-assembled Phospholipid/alkanethiol Biomimetic Bilayers on Gold," *Langmuir* 9: 2764-2767.

Regen et al. (1993) "Polymer-Supported Membranes. A New Approach for Modifying Polymer Surfaces," *Macromolecules* 16:335-338.

Ringsdorf et al. (1988) "Molecular Architecture and Function of Polymeric Oriented Systems: Models for the Study of Organization, Surface Recognition, and Dynamics of Biomembranes," *Angew. Chem. Int. Ed. Engl.* 27:113-158.

Roberts et al. (1996) "Dopamine Secretion by PC12 Cells Microencapsulated in a Hydroxymethyl Methacrylate-Methyl Methacrylate Copolymer," *Biomaterials* 17:267-275.

Ross et al. (2003) "Planar Supported Lipid Bilayer Polymers Formed by Vesicle Fusion. 1. Influence of Diene Monomer Structure and Polymerization Method on Film Properties," *Langmuir* 19:1752-1765.

Ross et al. (2003) "Planar Supported Lipid Bilayer Polymers Formed by Vesicle Fusion. 2. Adsorption of Bovine Serum Albumin," *Langmuir* 19:1766-1774.

Ruegsegger et al. (2001) "Reduced Protein Adsorption and Platelet Adhesion by Controlled Variation of Oligomaltose Surfactant Polymer Coatings," *J Biomed Mater Res* 56(2):159-167.

Schuler et al. (2001) "Decomposable Hollow Biopolymer-Based Capsules," *Biomacromol.* 2:921-926.

Seifert et al. (1993) "Charge Transport by Ion Translocating Membrane Proteins on Solid Supported Membranes," *Biophys. J.* 64:384-391.

Sells et al. (1994) "Two-Dimensional Polymerization of Lipid Bilayers: Degree of Polymermerization of Acryloyl Lipids," *Macromolecules* 27:226-233.

Shi et al. (2001) "Release Behavior of Thin-Walled Microcapsules Composed of Polyelectrolyte Multilayers," *Langmuir* 17:2036-2042.

Spinke et al (1992) Polymer-Supported Bilayer on a Solid Substrate. *Biophys. J.* 63:1667-1671.

Sun et al. (1993) "Ultrathin Self-Assembled Polymeric Films on Solid Surfaces. 2. Formation of 11(n-pentyldithio)undecanoate-Bearing Polyacrylate Monolayers on Gold," *Langmuir* 9:3200-3207.

Sun et al. (1996) "Spontaneous Polymer Thin Film Assembly and Organization Using Mutually Immiscible Side Chains," *J. Am. Chem. Soc.* 118:1856-1866.

Sun et al. (1994) "Ultrathin Self-Assembled Polymeric Films on Solid Surfaces. III. Influence of Acrylate Dithioalkyl Side Chain Length on Polymeric Monolayer Formation on Gold," *J. Vac. Sci. Technol.* 12:2499.

Sun et al. (2002) "Cytomimetic Biomaterials: Fabrication, Characterization, and Applications." In: Dillow et al., editors. *Biomimetic Materials and Design*, Marcel Dekker; p. 139-157.

Sun et al. (2002) "Design and Synthesis of Biotin Chain-Terminated Glycopolymers for Surface Glycoengineering," *J. Am. Chem. Soc.* 124(25):7258-9.

Sun et al (1998) The Synthesis of Neoglycophospholipid Conjugates Via an Improved Reductive Amination of W-oxoalkylglycosides and Phosphatidylethanolamines. *Carbohydrate Res* 370:77-81.

Sun et al. (2001) "Synthesis and Terminal Functionalization of Polymerizable Phosphatidylethanolamine," *Bioconjug Chem* 12:673-677.

Sun et al. (1996) "Normalization of Diabetes in Spontaneously Diabetic Cynomologus Monkeys by Xenografts of Microencapsulated Porcine Islets Without Immunosuppression," *J Clin Invest* 98:1417.

Taoka et al. (2000) "Neuroprotection by Recombinant Thrombomodulin," *Thromb Haemost* 83(3):462-8.

Taton et al. (2003) "Polymerization of Ethylene Oxide Using a Calixarene-Based Precursor: Synthesis of Eight Arm Poly(ethylene oxide) Stars by the Core-First Methodology," *J Polymer Science: Part A: Polymer Chemistry* 41:1669-1676.

Voigt et al. (1999) "Membrane Filtration for Microencapsulation and Microcapsules Fabrication by Layer-by-Layer Polyelectrolyte Adsorption," *Ind. Eng. Chem. Res.* 38:3047-4043.

Weber et al. (1999) "Long-term Survival of Poly-L-lysine-Alginate Microencapsulated Islet Xenografts in Spontaneously Diabetic NOD Mice," In: Lanza et al. ed. *Handbook of Cell Encapsulation Technology*, New York: Springer-Verlag;. p. 117-137.

Weber et al. (1994) "Encapsulated Islet Iso-, Allo-, and Xenografts in Diabetic NOD Mice," *Transplantation Proceedings* 27:3308-3311.

Weber et al. (1994) "NOD Mouse Peritoneal Cellular Response to Poly-L-Lysine-Alginate Microencapsulated Rat Islets," *Transplantation Proceedings* 26:1116-1119.

Weber et al. (1990) "Microencapsulated Dog and Rat Islet Xenofrafts Into Streptozotocin-Diabetic and NOD Mice," *Horm Metab Res* 35:219-226.

Wilchek et al. (1988) "The Avidin-Biotin Complex in Bioanalytical Applications," *Anal. Biochem.* 171:1-32.

Winger et al. (1999) "Formation and Stability of Complex Membrane-Mimetic Monolayers on Solid Supports," *Langmuir* 15:3866-3874.

Yoshioka et al. (1990) "Encapsulation of Mammalian Cell with Chitosan-CMC Capsule," *Biotechnol. Bioeng.* 35:66-72.

Ziani-Cherif et al. (1999) "Preparation of Aryldiazonium-, Aryldiazo-, and Arylazido-Derivatized Copolymers and Their Surface Photografting," *Macromol.* 32:3438-3447.

Chen et al. (1998) "Preparation of Novel Core-Shell Nanocomposite Particles by Controlled Polymer Bridging," *J. Am. Ceram. Soc.* 81(1):140-144.

Cui et al. (2003) "A Novel Approach for Islet Encapsulation with Bio-Membrane Mimetic System," IPITA Jul. 8-11, 2003, p. S65.

Hou et al. (2003) "Synthesis of Functionalized Multiarm Poly(ethylene oxide) Stars," Polymer, 44:5067-5074.

Leporatti et al. (2000) "Scanning Force Microscopy Investigation of Polyelectrolyte Nano- and Microcapsule Wall Texture," *Langmuir*, 16:4059-4063.

Neu et al. (2001) "Biological Cells as Templates for Hollow Microcapsules," *J. Microencapsulation*, 18(3):385-395.

Orban et al. (2000) "Cytomimetic Biomaterials. 4. In-situ Photopolymerization of Phospholipids on an Alkylated Surface," *Macromolecules*, 33:4205-4212.

US 5,556,632, 09/1996, Kohler et al. (withdrawn)

\* cited by examiner

METHOD FOR COATING LIVING CELLS

CROSS-REFERENCE TO RELATED APPLICATIONS

This application claims the benefit of U.S. Provisional Application No. 60/557,088, filed Mar. 26, 2004 which is incorporated herein by reference in its entirety to the extent not inconsistent herewith.

STATEMENT REGARDING FEDERALLY SPONSORED RESEARCH OR DEVELOPMENT

This invention was made with government support under DK069275 awarded by NIH. The government has certain rights in the invention.

FIELD OF INVENTION

The present invention pertains to encapsulation of isolated cells with a shape conforming barrier to which anti-inflammatory and/or anticoagulatory agents are incorporated and methods for encapsulating cells with these shape conforming barriers.

BACKGROUND OF THE INVENTION

Cells can be transplanted from a donor to a patient to produce biologics that may be absent, disrupted, or produced at insufficient levels in the patient. More generally, cells can be transplanted to effect a change to alleviate medical symptoms in a patient. However, the introduction of foreign donor cells into a patient often generates a host immune response that can destroy the transplanted cells. Research has focused on methods to minimize or abolish host immune response, thereby maximizing the effectiveness of the transplanted cells.

Animal models and clinical trials suggest a major obstacle in islet transplantation is a high rate of primary nonfunction and early islet destruction after intraportal islet infusion. Acute blood mediated inflammatory injury is largely responsible for functional stunning or destruction of islets and may amplify later immune reactions. Thus, there is a need in the art to generate an islet encapsulation barrier that is "actively" anti-inflammatory while preserving appropriate permeability characteristics for the exchange of nutrient and waste products, as well as passage through the barrier of useful biologics generated by the encapsulated cell. A particularly useful application of this barrier technology is for islet transplantation.

Whole organ pancreatic allografts using current immunosuppressive protocols have an expected graft survival as high as 86% at one year and 74% at 5 years after transplantation (1). Despite these encouraging results, the risk of major perioperative morbidity, the associated complications of chronic immunosuppression therapy, and the persistent shortage of donor organ tissue remain limitations of this approach. As a consequence, pancreas transplantation continues to have a limited role in the management of diabetes (2, 3).

Barrier strategies have focused on the coating of alginate microbeads with a membrane-mimetic film. Indeed, microcapsules/beads offer several distinct advantages over the use of other barrier devices including, greater surface to volume ratio, ease of implantation, and retrievability by lavage and needle aspiration when implanted into the peritoneal cavity. Nonetheless, the currently favored site for clinical islet transplantation involves infusion into the portal vein, where islets lodge in the terminal portal radicals. Relative advantages of the intrahepatic site in comparison to the peritoneal cavity include a substantially higher oxygen tension, as well as greater efficiency in the delivery of nutrients and removal of wastes. Unfortunately, standard microcapsules cannot be used in this site due to their large size (d ~500-600 µm) and the increased risk of portal vein thrombosis. These large diameters are required to achieve a high rate of islet encapsulation. As a consequence, use of a conformally coated islet barrier, based upon LbL polymer self-assembly, as a starting point for incorporation of membrane-based immunomodulatory proteins and carbohydrates is advantageous. Of note, the use of a conformal coating (i.e. a thin barrier film coated directly on the islet surface) is also associated with an inherent reduction in the large void volume typical of microcapsules, which favors a more efficient exchange of oxygen and nutrients. Indeed, formation of conformal islet barriers comprised of a single layer of adsorbed and photocrosslinked polyethylene oxide show promise in an intraperitoneal murine model (109-111).

As an alternative approach, islet transplantation offers several important advantages over whole organ transplantation. First, islets can be maintained and manipulated more easily than whole organ grafts and may be harvested from donor grafts that otherwise would not be suitable for whole organ transplantation. Second, islet transplantation, in comparison to whole organ grafting, is associated with a considerable reduction in morbidity and mortality, a decrease in intensive care unit utilization, shorter hospital stays, with the promise of achieving major reductions in overall healthcare costs. Finally, the opportunity to use a cell encapsulating barrier offers the potential to circumvent the vigorous humoral and cellular responses of the host; facilitating the use of xenogeneic islets or insulin producing cell lines, and thereby increase the supply of non-human donor tissue (2-10). Indeed, current cell encapsulating membranes are capable of isolating the cell transplant from the effects of direct cell-cell interactions, as well as large macromolecules (>100 kD), such as antibodies or associated immune complexes. Nonetheless, despite the production of a variety of permselective capsular membranes, including multicomponent polymer blends and phase inversion membranes, none have resulted in a clinically effective device for either allo- or xenogeneic cell transplantation. The barriers of the present invention improve immunoisolation by structurally mimicking the capacity of the cell membrane to both limit non-specific cell-cell interactions and control interfacial transport processes. In addition, incorporation of membrane-based immunomodulatory proteins and carbohydrates further minimizes adverse immune response to the transplanted cells. In this manner, both inflammatory and immunological processes that contribute to graft failure are limited by the presence of a biologically functional barrier. The cell conforming barrier disclosed herein is not limited to only transplanted islet cells, but can be utilized for any to-be-transplanted cell.

The design characteristics of an immunoisolation barrier are dictated by an intent to limit the effects of rejection pathways initiated after the implantation of donor tissue. Notably, while some overlap exists, the immunological pathways responsible for autoimmune destruction of isogeneic islets or rejection of allogeneic islets differ from those primarily operative in the rejection of xenogeneic grafts. In the former two cases, islet damage appears to be mediated by a primary 'Th1' immune response in which the dominant effector cell is a cytotoxic $CD8^+$ T cell (11-14). Specifically, host $CD8^+$ T cells are activated by donor MHC-peptide complexes expressed on the surface of graft-derived antigen presenting cells; a process that has been referred to as direct antigen presentation. In contrast, rejection of islet xenografts is characterized by a 'Th2' response in which CD4+ helper T cells, but not CD8+ cells, play a major role (15-20). In this pathway, termed indirect antigen presentation, host antigen presenting cells display peptides scavenged from free donor proteins to engage CD4+ T cells, which develop into Th2 cells (21-23). In turn, Th2 cells stimulate the maturation of B cells into plasma cells, which secrete xenoantigen specific antibodies. Immune complexes are generated by the binding of newly formed antibodies to xenoantigens, which may lead to the activation of macrophages (MØ) and recruitment of neutrophils to the islet transplant by activation of the complement cascade or by direct binding of antigen-antibody complexes to leukocyte cell surface Fc receptors (24). Although CD8+ reactivity predominates in allograft immunity and CD4+ reactivity is a primary factor in xenograft immunity, these distinctions are not absolute and both pathways may be active to lesser or greater degrees.

Given this framework, cell isolation strategies that prevent cell-cell contact between donor cells and host immune cells block the direct antigen presentation pathway. While the feasibility of attaining this goal has been demonstrated, the capacity of a barrier to limit indirect antigen presentation by preventing the release of graft protein or peptide antigens, shed from the islet surface or liberated from necrotic or apoptotic cells, is difficult. Moreover, once an immune response is initiated, the selective exclusion of low molecular weight cytokines and free radicals that may be released by immune and inflammatory cells in the region of the graft, while simultaneously permitting the passage of insulin, glucose, or other nutrients, has not been achieved. There is a need in the art, therefore, to minimize an immune response while simultaneously permitting exchange across the barrier of selected substances produced by the transplanted cells. This invention addresses this need by incorporating inflammatory and/or thrombogenic inhibitors in a conformal barrier generated by layer-by-layer (LbL) polymer assembly. Such barriers "actively" limit those immune mediated responses related to indirect antigen presentation, in addition to preventing cell-cell interactions that underlie the initiation of the CD8+-dependent pathway. This is achieved by the incorporation of immunomodulatory proteins and carbohydrates into the encapsulation barrier, which limit the activation of macrophages and T cells, as well as the complement pathway. Such a barrier can also limit later induction of an immune response by abrogating early inflammatory graft injury.

Islets from two to four donor organs are typically required to reverse diabetes in a single patient, placing a significant burden on an already limited donor organ supply (26, 27). Moreover, a requirement for successive islet infusions within the portal bed necessitates re-interventions with increased costs, the attendant risk of periprocedural morbidity, and has been associated with increasing portal vein pressures that may indicate the development of a presinusoidal form of portal hypertension. Primary nonfunction may be the consequence of poor functional quality of the grafted tissue, an inadequate mass of transplanted islets, or lack of vascularization of the graft (28). However, substantial evidence now suggests that exposure to an early, nonimmune inflammatory injury is largely responsible for the observed functional stunning or destruction of islets and may well amplify subsequent immune reactions (29-33). The cell encapsulating barriers of the present, therefore, are useful in preserving islet function by limiting early nonimmune inflammatory injury, thereby reducing requirements for donor islet mass.

Although activation of the graft microenvironment by endotoxin (34, 35) and lipopolysaccharides has been postulated to contribute to induction of a local inflammatory response, an acute blood mediated inflammatory reaction is initiated upon intraportal infusion of islets (36-38). Specifically, in animal models and in recent clinical reports, marked activation of coagulation has been noted after islet infusion, despite the presence of heparin in the infusate, as indicated by increases in thrombin-antithrombin (TAT) complexes, prothrombin activation fragments, and fibrinopeptide A. Indeed, others have also observed overt, as well as subclinical episodes of portal vein thrombosis after islet transplantation (39, 40). Prothrombotic triggers include the expression of tissue factor (TF) either by transplanted islets or by locally injured endothelial cells (37, 38). As a consequence of thrombin generation, activated platelets bind to the islet surface and further amplify the coagulation cascade. Notably, thrombin is a direct mediator of inflammation, acting as a chemoattractant for neutrophils and monocytes and stimulating endothelial cells to express monocyte chemoattractant protein-1 (MCP-1) and other chemokines. Thrombin also induces endothelial cell expression of ICAM-1, VCAM-1, and P-selectin, as well as platelet activating factor, all of which leads to further recruitment of platelets and leukocytes to the graft site (41, 42). Likewise, by-products of the thrombin response, including fibrinogen degradation products and fibrin, also act as chemoattractants and serve to localize this inflammatory response by adhesion-dependent processes. Furthermore, thrombin activated endothelial cells leukocytes express oxygen free radicals, IL-1$\beta$, TNF-$\alpha$, IFN-gamma, and iNOS, which can damage islets, inducing either functional impairment or death (43). Consistent with these observations, immunohistochemical analysis of grafts with primary nonfunction has demonstrated robust macrophage infiltration (29, 44).

Both heparin and thrombomodulin have a pronounced inhibitory effect on thrombotic, inflammatory, and redox related responses. For example, heparin dramatically enhances the ability of heparin cofactor II and antithrombin III to inactivate thrombin. Moreover, heparin inhibits the formation of nitric oxide by binding superoxide dismutase (45) and limits complement mediated effects by inhibiting the formation of C3 convertase and the assembly of C5b-9 (46-48). Perhaps of greater physiologic significance is thrombomodulin (TM), a 60 kD type I transmembrane protein that forms a 1:1 molar complex with thrombin (49-53). In the process, TM switches off all known procoagulant/proinflammatory functions of thrombin, and instead channels the catalytic power of the enzyme into complex anticoagulant/anti-inflammatory activities. Specifically, thrombin bound to TM is incapable of cleaving fibrinogen, nor is it able to activate factor V or platelets (54). It is particularly noteworthy, however, that TM significantly enhances the rate of thrombin inactivation by ATIII (~8-fold) and dramatically accelerates (~20,000-fold) the ability of thrombin to activate protein C (APC). Activated protein C together with its cofactor protein S inactivates two coagulation factors, Va and VIIIa, thereby preventing the generation of Xa and thrombin, which are critical for the amplification of both inflammatory and coagulation responses. Apart from thrombin and Xa related processes, APC also inhibits mononuclear phagocyte (MØ) activation and the production of pro-inflammatory cytokines, such as TNF-a, IL-1b, which are known to be cytotoxic to islets (55-58). This inhibitory effect has been observed in response to LPS, IFN-gamma, as well as phorbol myristate acetate. APC also suppresses MØ-dependent proliferative responses of T cells, inhibits mixed lymphocyte responses of human and rat mononuclear cells, and when administered systemically prolongs xenograft survival in a guinea pig to rat cardiac transplant model (58). Furthermore, APC limits neutrophil binding to selectins (59), which indirectly reduces the elaboration of cytokines by endothelial cells. It is notable that a variety of pro-inflammatory cytokines downregulate endothelial cell expression of TM with a concomitant decrease in APC production (60). While APC and heparin have been administered systemically as anti-inflammatory agents, their potent anticoagulant activity limits their effective dose range and, therefore, diminishes their potential therapeutic impact.

In addition to thrombin generation, local release of adenine nucleotides, including ATP and ADP, from activated endothelium and platelets further potentiate proinflammatory and prothrombotic events. Specifically, both ATP and ADP are released into the extracellular environment from activated endothelium and are secreted in high concentrations by platelets following their stimulation with exogenous ADP, collagen, thrombin, or activated complement components (61, 62). These purinergic mediators act as a positive feedback stimulus initiating further recruitment and sequestration of platelets and activating endothelial cells. Of interest, both collagen and thrombin-induced platelet responses are critically dependent on the presence of released ADP, which interacts with purinergic type 2 (P2) receptors as a powerful agonist for platelet adhesion and aggregation. Extracellular ATP also interacts with P2 receptors, including P2X7 receptors that induce pore formation in cell membranes, and promotes IL-1 release from macrophages and endothelial cells. Furthermore, both ATP and ADP activate neutrophils and trigger nitric oxide release from endothelial cells. In summary, elevated concentrations of ATP and ADP predispose to thrombosis and inflammation at the vascular wall interface. An important regulator of these events is CD39, which is an endothelial cell transmembrane protein with both ecto-ATPase and ecto-ADPase activities, which rapidly metabolizes extracellular ATP and ADP to AMP (63-65). By reducing local concentrations of ATP and ADP, CD39 represents a physiologically important antithrombotic/anti-inflammatory regulatory mechanism-blocking platelet aggregation and recruitment in response to a wide range of stimuli, as well as other EC and leukocyte mediated pro-inflammatory events (66, 67). Indeed, in an intriguing report intravenous administration of soluble CD39 has been shown to prolong whole organ xenograft survival and abrogate platelet activation and deposition seen in this setting (68, 69). Of note, endothelial cell CD39 expression is rapidly downregulated by reperfusion injury, oxidant stress, or cytokine-mediated EC activation responses, all of which occur at the time of portal islet infusion (64, 70).

A comparatively new generation of polymeric shell has been recently introduced, based on the "layer-by-layer" (LbL) assembly of oppositely charged polymeric species onto an underlying substrate (71). The attractiveness of this strategy is based on the observation that film architectures and thickness are completely determined by the deposition sequence and that many different materials can be incorporated in individual multilayer films (72-76). Furthermore, since the process only involves adsorption from solution, there are no restrictions with respect to the size or topology of the object to be coated. In this regard, this strategy offers a new approach for the fabrication of thin multicomponent films directly on cell surfaces (77-79). Thus, the surface of the pancreatic islet and many of its attendant properties can be re-engineered. TM, heparin, and CD39, as components of a conformal islet coating, provide a rational strategy for generating an "actively" anti-inflammatory barrier that reduces primary islet non-function. Moreover, by abrogating early inflammatory graft injury, later induction of an immune response is limited with improved long-term graft survival. The LbL assembly strategy can be combined with membrane-mimetic strategies, as disclosed in U.S. patent application Ser. No. 10/343,408 filed Jul. 22, 2003, herein incorporated by reference, to further increase transplant efficacy.

BRIEF SUMMARY OF THE INVENTION

The invention comprises cells useful for transplantation into a patient that are coated with a thin-film shape-conforming barrier to maximize the efficacy and lifetime of the cells after transplantation, and methods of coating these cells with these shape-conforming barriers. The barrier is made by adsorbing alternate layers of oppositely charged polymers. In an embodiment, the negatively charged polymer alginate (ALG) is the initial layer bound to the cell surface. The positively charged polymer, poly-L-lysine, (PLL) is then adsorbed to form an ALG/PLL layer. The shape-conforming barrier can comprise one layer. The shape-conforming barrier can comprise more than one layer. In a preferred embodiment the shape conforming comprises between three and ten layers, inclusive. A film can be attached to the outermost polymer layer. The film can be an ALG polymer, a membrane mimetic film (MM), or an avidin-conjugated ALG layer. The outermost film can alternatively be a positively charged polymer, including PLL. PLL can be substituted with other positively-charged polymers, including protamine, as known in the art. The negatively charged layer can be substituted with other negatively-charged polymers, as known in the art. A polymer within a layer can be a polymer containing photoactive groups that can from interlayer covalent bonds. The photoactive group can be photoactive diazonium groups (DR). A polymer can contain avidin. Thus, a layer can assemble by electrostatic, covalent, avidin-biotin interactions, or any combination thereof.

The shape-confirming barrier has controllable permeability characteristics. The molecular weight of the polyelectrolytes can be varied to vary permeability properties. For example, relatively low molecular weight PLL reduces the size of bioactive agents that can cross the barrier. In addition, the barrier can comprise dendrimetic compounds to further control barrier permeability characteristics. The barrier can be "actively" nonimmunogenic by incorporating bioactive agents into the barrier.

In an embodiment individual cells, including islet cells, are coated. In another embodiment, the coating is for a group of cells, including an islet. The present invention encompasses coating any living cell, including both naturally occurring cells as well as cells that have been genetically modified. In a preferred embodiment the cell to be coated is an islet cell.

The invention encompasses methods for generating a conformal cell barrier via layer-by-layer polymer assembly. In an embodiment, the invention uses alternating layers of negatively charged and positively charged synthetic or native polymers, including linear, branched, or dendrimeric polymers. Each layer comprises a negative and positive polymer pair self-assembled. The invention includes two or more such layers. Preferably, there are between three and ten, inclusive, layers. The negatively charged layer can be alginate and the positively charged layer can be protamine. A polymer can contain photoactive groups, including photoactive diazonium groups, capable of forming interlayer covalent bonds. Thus, a layer can be formed by a combination of electrostatic and covalent bonds. In addition, a polymer can contain biotin, avidin or streptavidin so that layers can also be held together through biotin-(strept)avidin. Those skilled in the art recognize polymers can be held together by any on of these interactions, or any combination therein, and by other interacting means known in the art.

The external-most facing layer can comprise external surface anchoring groups for attachment. For example, biologic agents (including proteins and carbohydrates) for inhibiting inflammation can be attached, other cell types, vesicles, and vesicles containing biologic agents can all be attached. The conformal coating can itself comprise TM, heparin and/or CD39. TM, heparin and/or CD39 can be bound directly to the barrier via covalent, ionic, or biotin/streptavidin interactions. TM, heparin and/or CD39 can be attached to the surface via incorporation into lipid vesicles bound to the barrier surface. The invention encompasses other inhibitory biologics known in the art, for example albumin, prostacyclin analogues, etc. The invention encompasses surface barriers containing combinations of any anticoagulant and/or anti-inflammatory agent, either bound directly or indirectly to the surface. These agents can also be controllably released from the barrier surface. The conformal surface barriers can be for porcine islets, human islets, genetically engineered insulin secreting cells, any genetically engineered cell used for transplantation, neurons, cardiac myoblasts, mycocardial cells, chondrocytes, dopamine secreting cells, or other cell types intended for cell therapy by transplantation or implantation.

DETAILED DESCRIPTION OF THE INVENTION

Figure 1A:
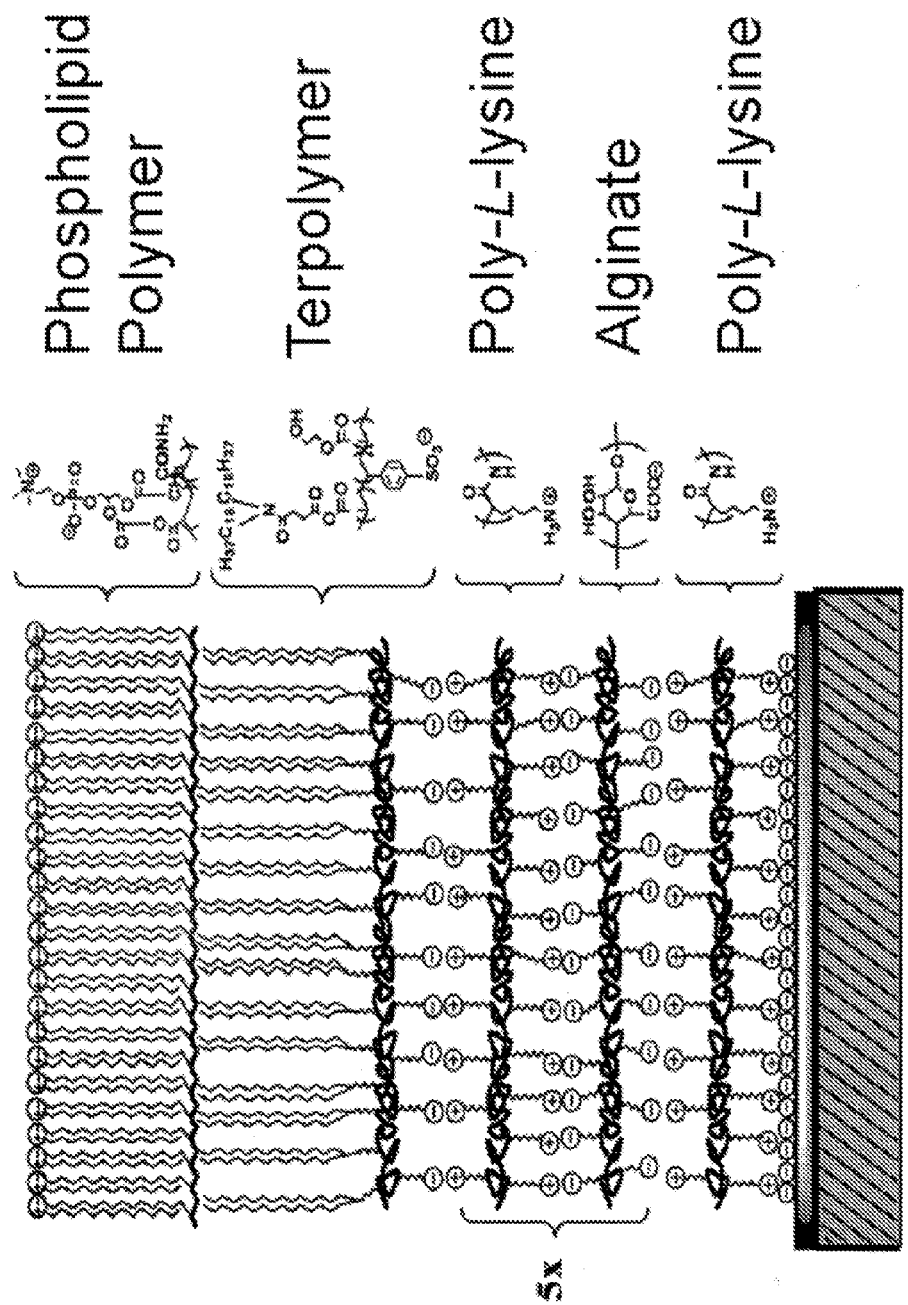
FIGS. 1A-B: (A) Illustration of a polymerized lipid bilayer on a supporting substrate. The supporting substrate is a multilayer assembly formed by consecutive adsorption of anionic and cationic polyelectrolytes followed by terpolymer and lipid deposition. (B) Chemical structure of bifunctional lipids: acrylPE-FITC (8), acrylPE-Biotin (9), and acrylPE-EMC (10). The FITC conjugate provides a mechanism for direct detection of the lipid membrane on supporting substrates.

The invention may be further understood by the following non-limiting examples. All references cited herein are hereby incorporated by reference to the extent not inconsistent with the disclosure herewith. Although the description herein contains many specificities, these should not be construed as limiting the scope of the invention but as merely providing illustrations of some of the presently preferred embodiments of the invention. For example, thus the scope of the invention should be determined by the appended claims and their equivalents, rather than by the examples given. In general the terms and phrases used herein have their art-recognized meaning, which can be found by reference to standard texts, journal references and contexts known to those skilled in the art. The following definitions are provided to clarify their specific use in the context of the invention.

The invention encompasses electrostatic LbL conformal barriers and covalent LbL conformal barriers and are particularly useful for coating islet cells. The electrostatic LbL conformal barriers are characterized as standard film (Alg/PLL)$_n$ Alg, membrane-mimetic film (Alg/PLL)$_n$MM and surface bound lipid vesicles (Alg/PLL)$_n$(Alg/avidin)$_m$-biotin-vesicle. The electrostatic covalent LbL conformal barriers are characterized as standard film (Alg/DR)$_n$Alg, membrane-mimetic film (Alg/DR)$_n$MM and surface bound lipid vesicles (Alg/DR)$_n$(Alg/avidin)$_m$-biotin-vesicle. In the simplest embodiment, n=1 and the barrier is one layer comprising a negatively and a positively charged polymer electrostatically interacting. In a preferred embodiment, n≧2 and m≧1 and alginate is the initial layer bound to the cell (e.g. an islet cell) or in the case of model films, a silicon wafer. MM refers to those systems in which a planar membrane-mimetic lipid film is deposited as the outermost layer. Barrier efficacy and effectiveness can be assessed by means known in the art, including minimizing non-specific inflammatory and/or pro-coagulant responses; limiting and/or maximizing passage of bioactive substances across the barrier; excluding access and/or binding to IgG and complement. Although Alg and PLL are specific polymers, those skilled in the art recognize that Alg can be substituted with a different negatively charged polymers and PLL can be substituted with a different positively charged polymer.

"Coating" is used herein to refer to the process whereby a living cell to be coated is immersed in a solution that can adsorb to the living cell's surface, thereby coating the surface. Alternatively, coating refers to the same process except the surface to be coated has already been coated. The coating need not cover the entire surface, so long as there is substantial coating. Substantial coating refers to the coating having a measurable improvement in the efficacy of coated transplanted cells relative to the uncoated transplanted cells. Efficacy can be evaluated, as known in the art, by cell survival after implantation and production of bioactive agents by the transplanted cells, for example.

A "conformal barrier" or "shape-conforming barrier" refers to a thin barrier film coated directly on the living cell surface. The barrier is generally less than one micron thick. As used herein, "cell" refers to living cells that have been removed from their natural conditions so that a relatively homogeneous cell population is obtained in vitro. Preferably, these are living cells that are to be transplanted into a patient to obtain a beneficial effect.

The coated cells can have a plurality (e.g. more than one) of layers coating the cell, thereby improving anti-inflammatory and anti-coagulant properties while maintaining permeability characteristics to allow exchange of beneficial substances across the barrier. These layers are formed by LbL polymer assembly, wherein the living cell is initially immersed in a positively (basic) charged polyelectrolyte, thereby adsorbing the polyelectrolyte to the cell surface. The living cell (now coated) is subsequently immersed (e.g. dipped) in alternating charged polyelectrolyte solutions. The charged polymers can be manipulated to provide additional control over barrier properties through covalent and non-covalent polymer interactions. Membrane-mimetic films can be attached to the outermost layer. Membrane-mimetic surface films are known in the art, as disclosed in U.S. patent Ser. No. 10/343,408 filed Jul. 22, 2003 and Ser. No. 10/257,805 filed Apr. 15, 2003, hereby incorporated by reference.

As used herein, "bioactive agent" is used very broadly to refer to any substance that has a biological effect. The bioactive agent can be naturally occurring or can be a pharmaceutical drug. In a preferred embodiment, bioactive agents attached to the barrier are anticoagulant and/or anti-inflammatory agents, as known in the art. Bioactive agent also encompasses agents secreted by the to be implanted cell that can have a beneficial biological effect on a patient once the cell has been transplanted.

Two-dimensional thin films. A thin film barrier can be constructed modeled on the structure of cellular membranes. FIG. 1A illustrates construction of a polymerized lipid bilayer on a supporting substrate. The supporting substrate is a multilayer assembly formed by consecutive adsorption of anionic and cationic polyelectrolytes followed by terpolymer and lipid deposition. Similar types of cell encapsulating barriers can function as effective immunoisolation barriers and have controllable transport properties and surface physiochemical characteristics. We successfully synthesized monoacrylate functionalized lipid monomers and demonstrated that, as unilamellar vesicles, these lipid monomers could fuse onto a variety of alkylated substrates and form a two-dimensional thin film (FIG. 1A). Stabilization of the lipid assembly was achieved using a rapid visible light-mediated photopolymerization scheme, which was effective at room temperature (83). Success in coating 2-D surfaces established a foundation for coating alginate microbeads (84, 85) and coating isolated cells. Detailed investigations of surface properties including contact angle goniometry, ESCA, ellipsometry, FT-IR spectroscopy, as well as neutron reflectivity and high resolution SEM have been reported for both 2-D and 3-D systems (83, 86-88).

Figure 1B:
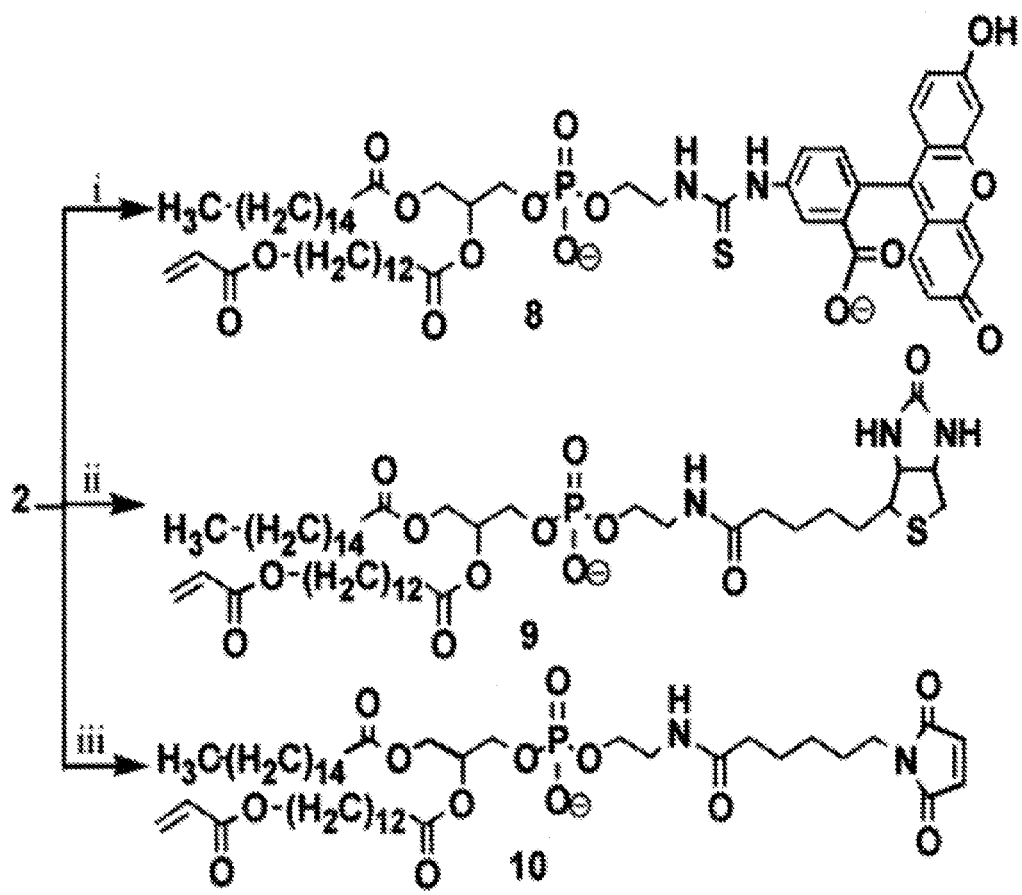

Synthesis and characterization of a multifunctional membrane-mimetic encapsulation barrier. In order to assess the uniformity of film coating, as well as the stability of the encapsulation barrier in vitro and in vivo, we described the synthesis of an acrylate-functionalized phosphatidylethanolamine (mono-AcrylPE, 2 (FIG. 1B). Notably, the amino function can serve as a handle for further modifications, including the introduction of terminal groups, such as biotinyl and N-(ε-maleimidocaproyl) succinimide (EMC) (FIG. 1B) (89, 90). We have confirmed that these linkers facilitate the incorporation of target molecules via high affinity biotin interactions or by covalent attachment (EMC). For example, we have generated polymerizable lipid conjugates that carry fluorophores, such as FITC or Texas red and utilized these probe molecules to visualize the film coating on alginate microbeads. A fluorescent image of an alginate/PLL microbead (300 micron diameter) coated with Acryl-PC (99 mol %) and AcrylPE-FITC (1 mol %) reveals a thin uniform fluorescence adjacent to the microbead-coated surface (data not shown). These conjugates allow visualization of the coat, thereby enhancing capacity to optimize the film coating process allowing us to demonstrate that polymeric lipid films have excellent stability during prolonged periods of incubation under shear or static conditions (87, 91).

Figure 2A:
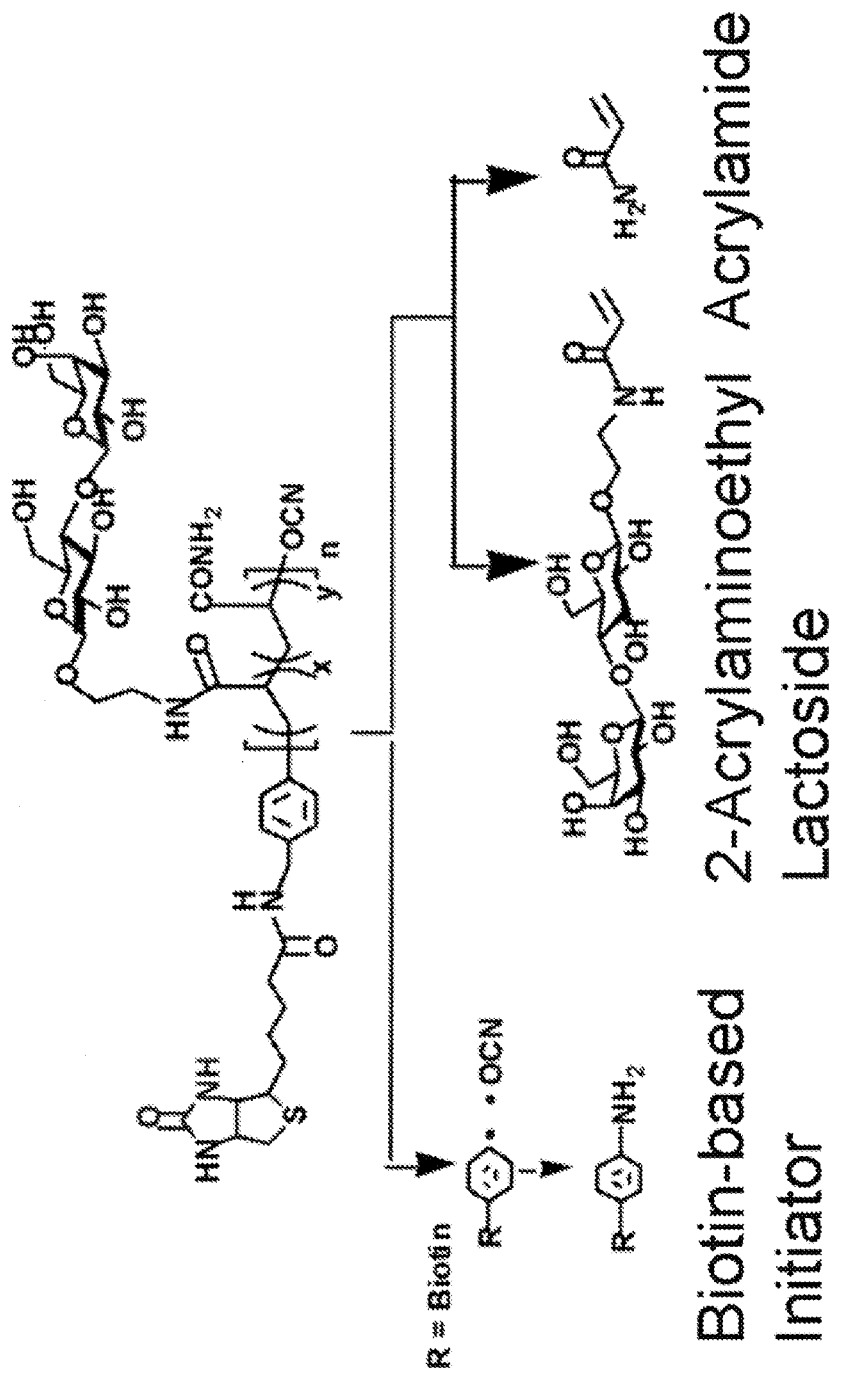
FIGS. 2A-D: (A) Synthetic scheme illustrating use of a biotin terminated initiator in the synthesis of a biotinylated lactose bearing glycopolymer. (B) Confocal fluorescent images of FITC-lectin binding to a glycopolymer film anchored to a patterned PET membrane via biotin/streptavidin interactions. (C) FITC-streptavidin bound to a membrane-mimetic thin film containing 25 mol % biotin-lipid demonstrating microdomain formation. (D) FITC-lectin bound to a glycopolymer coating anchored onto a membrane-mimetic thin film containing 25 mol % biotin-lipid illustrating that the extended chain conformation of the glycopolymer locally expands to create a uniform glycocalyx-like coating.
Figure 2B:
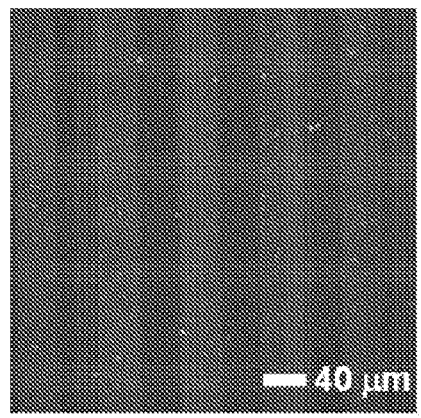
Figure 2C:
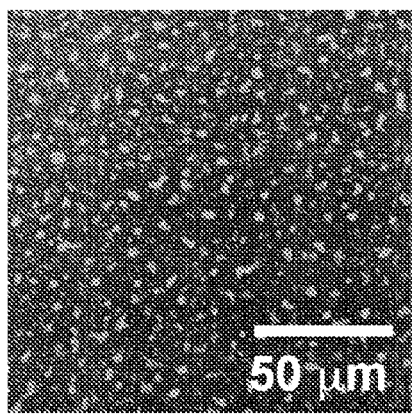
Figure 2D:
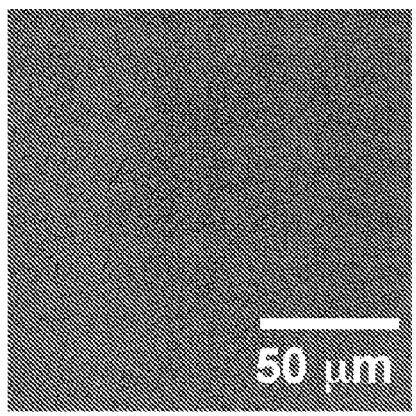

Synthesis of biotin terminated glycopolymers for generating a membrane-mimetic glycocalyx (88, 92). A single biotin group can be placed at the terminus of synthetic hydrophilic polymers bearing carbohydrate pendant groups (FIG. 2A). The motivation for this effort was based upon the observation that glycocalyx-like barriers reduce non-specific cell and protein interactions and thereby provide a route for enhancing film coating biocompatibility (93, 94). Details of these approaches, including synthetic schemes, yields, and surface property characterization have been described elsewhere (88, 95). In brief, glycocalyx like coatings have been produced on patterned streptavidin coated substrates, as well as on biotin-bearing lipid membrane-mimetic thin films (FIGS. 2B-D).

Figure 3:
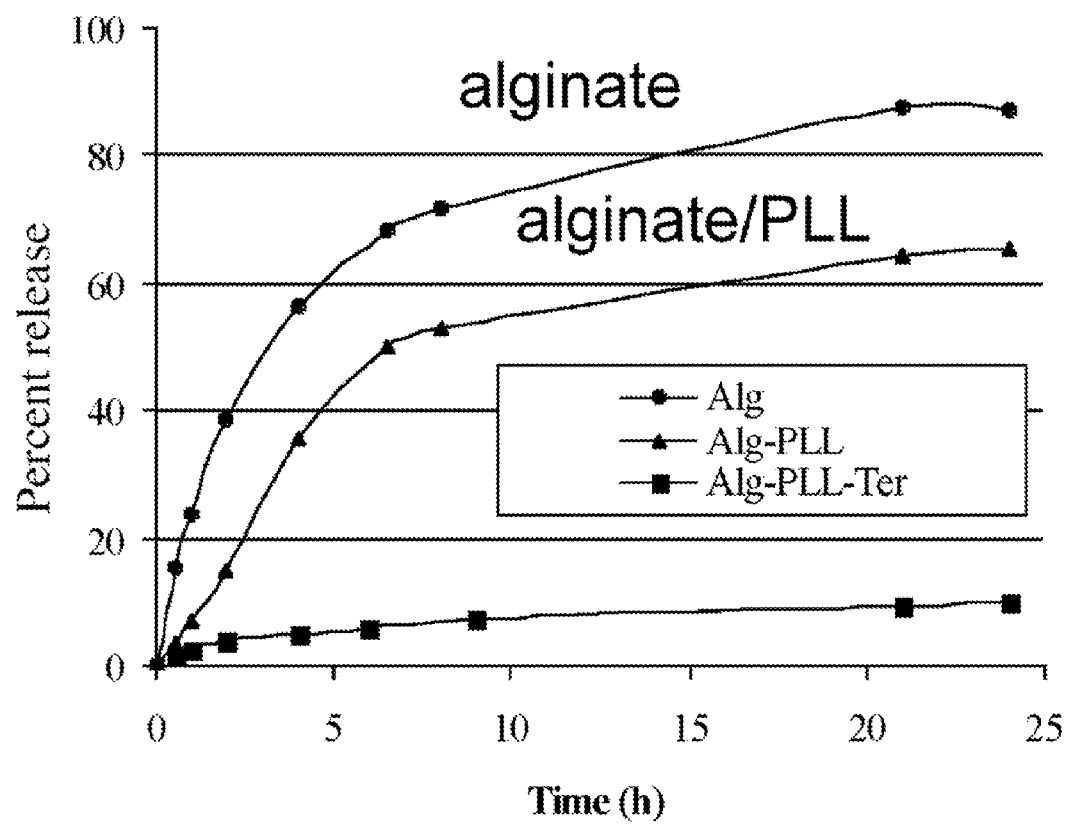
FIG. 3: Comparison of release rates of encapsulated 71 kDa FITC-dextran from alginate-PLL microbeads coated with a photopolymerized membrane-mimetic surface. Permeability decreased after coating with an alginate/PLL multilayer and was substantially reduced after placement of the first portion of the membrane-mimetic film (i.e. terpolymer base; Alg-PLL-Ter). No release of 71 kD FITC-dextran was observed after coating with final polymeric lipid layer (data not shown).

Manipulation of interfacial transport properties by alginate/PLL coating. Alginate-calcium chloride systems have been used to produce monodisperse, spherical, semipermeable beads at a high production rate. As a cell-compatible polysaccharide, alginate is an appealing polymer. Transport properties can be manipulated by post-coating of alginate with an additional thin film (97, 98). In contrast, a membrane-mimetic lipid assembly can provide a useful mechanism for modulating permeability. This permeability modulation was assessed using a series of FITC-labeled dextrans as model compounds (87). As illustrated in FIG. 3, the presence of an alginate/PLL layer decreases 71 kDa FITC-labeled dextran release. The presence of a polymerized lipid film with the alginate/PLL layer further decreases the permeability of the barrier to 71 kDa FITC-labeled dextran. These data demonstrate that a membrane-mimetic barrier can protect encapsulated cells from the effects of circulating antibodies. Additional details regarding the permselectivity of membrane-mimetic films have been reported elsewhere (87, 96). In addition, these data suggest that by varying the number of alginate/PLL layers the permeability can be likewise manipulated. Accordingly, two levels of control in barrier permselectivity have been established. First, permeability may be influenced by the formation of an alginate/PLL multilayer. For example, selection of a PLL of low molecular weight (e.g. 28 kD) will reduce permeability due to the interpenetration of PLL and alginate chains yielding a more compact membrane. Likewise, the number of alginate/PLL multilayers will also influence permeability. Thus, an alginate/PLL layer can be fabricated in a manner, which either contributes greatly or very little to barrier permeability. Second, as illustrated by these investigations, the presence and structure of a membrane-mimetic film has the capacity to provide an additional level of control over barrier permeability.

These experiments demonstrate that stable, membrane-mimetic barriers can be produced on alginate microbeads by a combination of self-assembly and in situ polymerization strategies. Significantly, the development of novel polymerizable lipid conjugates allows film uniformity and stability to be monitored in an unambiguous fashion. Moreover, by extending the chemical functionality of membrane lipid constituents, glycocalyx-like films can be fabricated. Finally, we have demonstrated that a membrane-mimetic coating provides a mechanism for modulating both surface and interfacial transport properties.

Figure 4A:
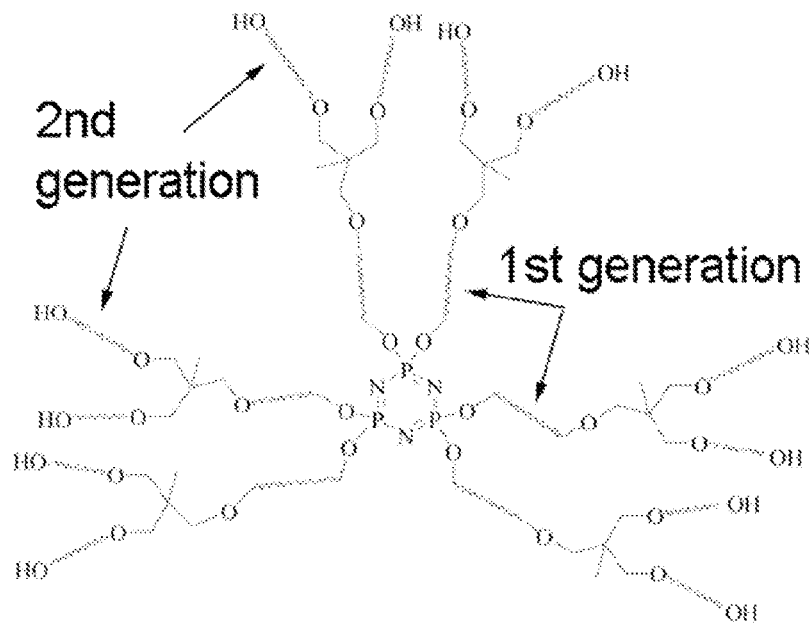
FIGS. 4A-C: (A) PEO dendrimer comprised of two macromolecular generations, which allows control of internal void volume or compactity. A two-generation dendrimer synthesized is illustrated for simplicity. (B) One example from a series of PEO-PAA dendrimers that have been synthesized to facilitate electrostatic anchoring to a charged surface via a negatively charged peripheral PM block. A two-generation $PEO_3$-b-$PAA_6$ dendrimer is illustrated. (C) Surface bound dendrimer anchored by negatively charged groups ($COO^-$ or $SO_3^-$) within a membrane-mimetic film creating a channel of size and porosity dictated by well-defined PEO branch size and structure.

Synthesis of dendrimer-like polymers to tailor both surface and transport properties of membrane-mimetic immunoisolation barriers. Synthesis of well-defined multi-generation poly(ethylene oxide) (PEO) dendrimers. Synthetic membrane-based pores of appropriate size and dimension can provide a mechanism for achieving greater control over macromolecular transport processes relevant to the creation of an immunoisolation barrier. Although a variety of molecular geometries have been exploited in the creation of transmembrane channels, star shaped polymers or dendrimers can provide a useful starting point for creating nanometer scale pores. New methodologies have been developed to synthesize dendrimers whose generations are true macromolecular chains of precisely controlled length (99-102) (FIG. 4). Because of the 'living' character of these polymerizations, the length of the PEO branches and thus the size of each generation can be accurately controlled. The polydispersity index ($M_w/M_n$) of these dendrimers is typically less than 1.2, which indicates the synthesis of very homogeneous macromolecules with a narrow distribution of molecular sizes. As a consequence of this effort, PEO dendrimers of up to six generations have now been produced with molecular weights as large as 400,000 (PDI 1.15).

Figure 4B:
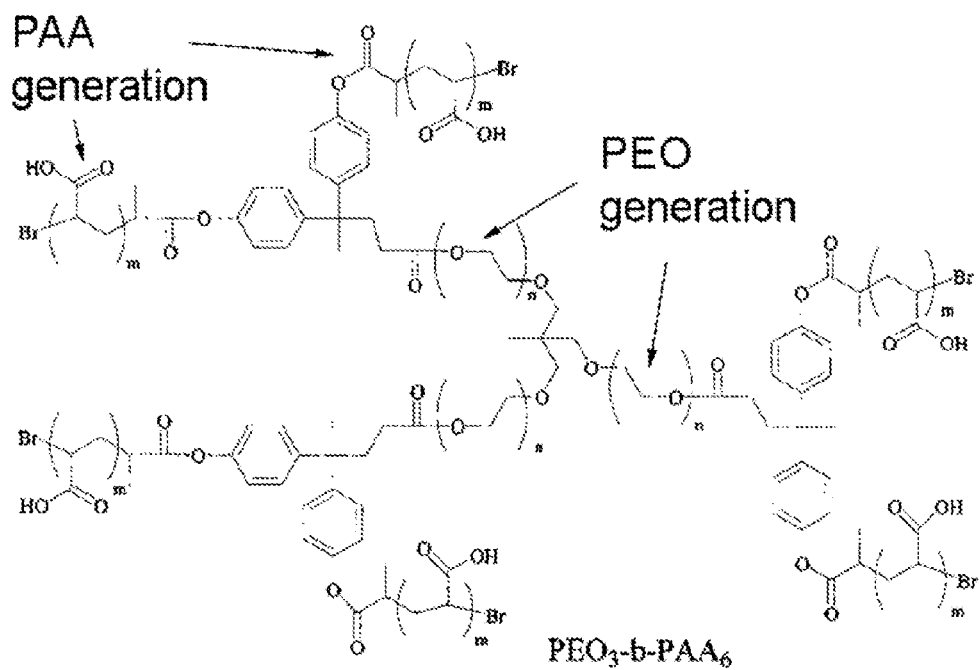
Figure 4C:
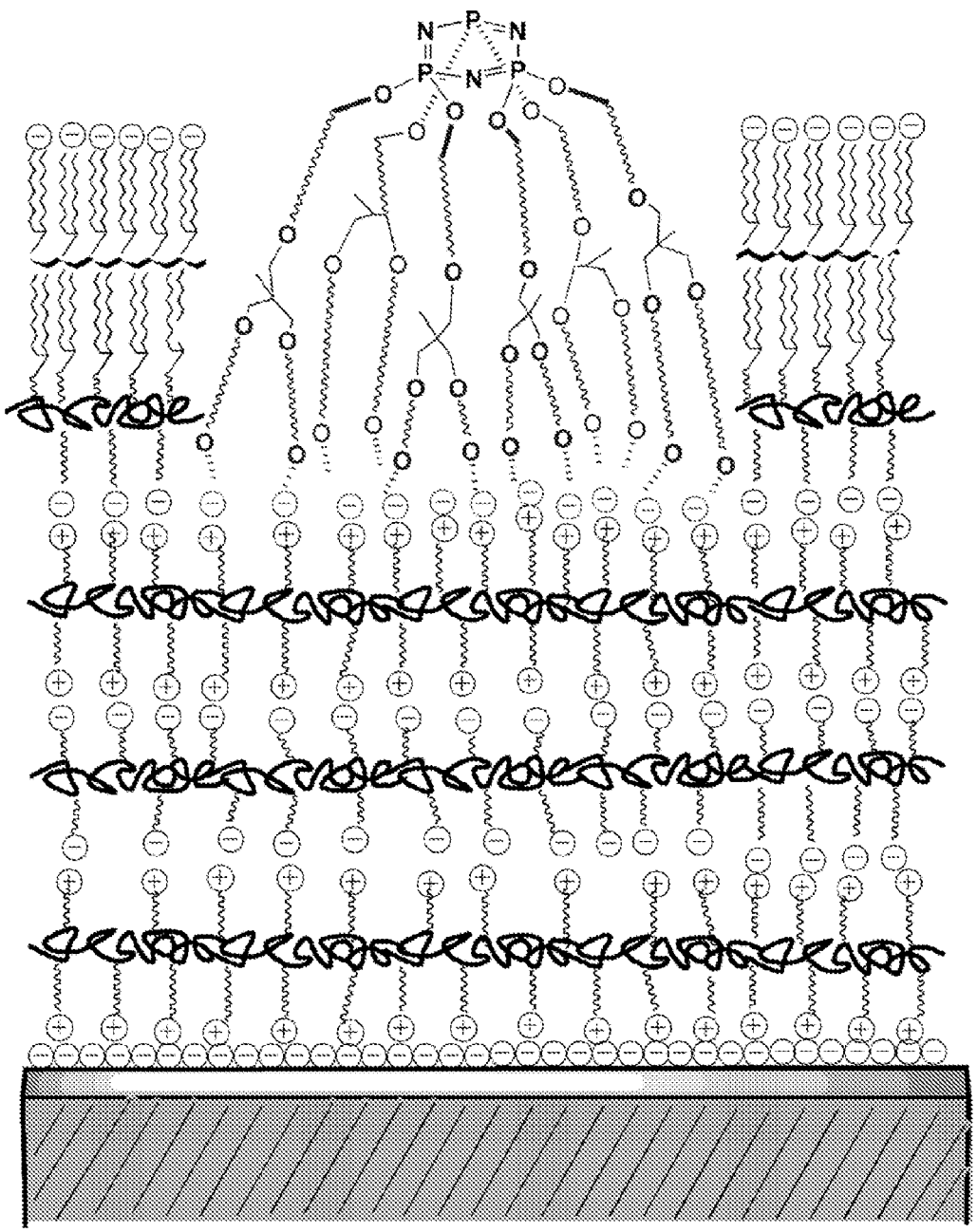

A critical requirement for stable incorporation of dendrimeric "artificial pores" into a membrane-mimetic film is the placement of substrate anchoring groups at the terminal ends of the outer generation of dendrimer chains. In this regard, we developed a strategy to synthesize PEO dendrimers containing an outer generation of negatively charged, poly(acrylic acid) (PAA) blocks. This was achieved by combining the anionic polymerization of ethylene oxide with the use of controlled/living radical polymerization (i.e. ATRP) of tert-butyl acrylate with subsequent hydrolysis of the tert-butyl groups to afford poly(acrylic acid) (102) (FIGS. 4B-C). All told, a variety of PEO-PAA dendrimer block copolymers have been synthesized and film transport studies demonstrate that these stars provide an additional level of control over barrier permeability when incorporated either into the outermost membrane-mimetic film or doped into the alginate solution used to produce the alginate/PLL multilayer.

Figure 5A:
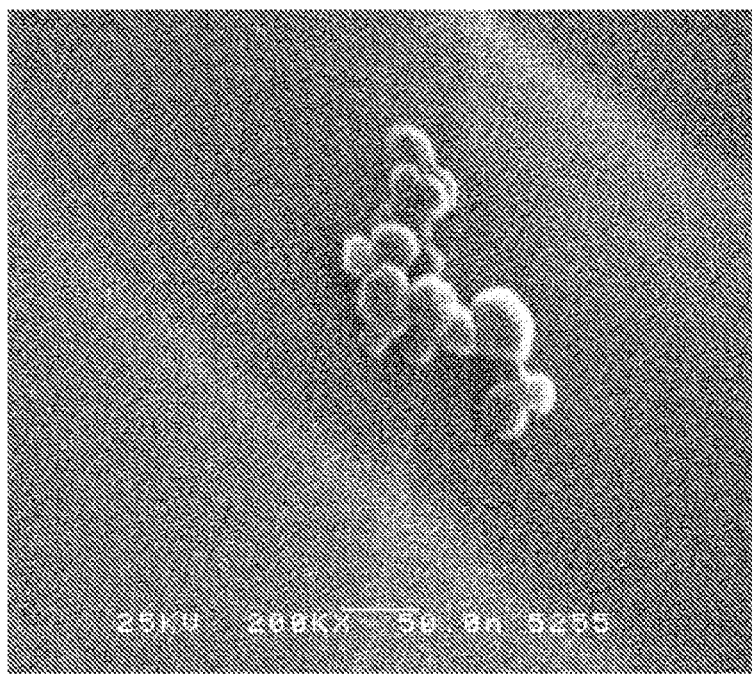
FIGS. 5A-B: (A) Cryo-high resolution scanning electron microscopy of PEO dendrimers (MW 405K) in vitrified water on a gold specimen carrier (freeze-fracture) d~30 nm. (B) Cryo-HRSEM of PEO dendrimers on a thin film.
Figure 5B:
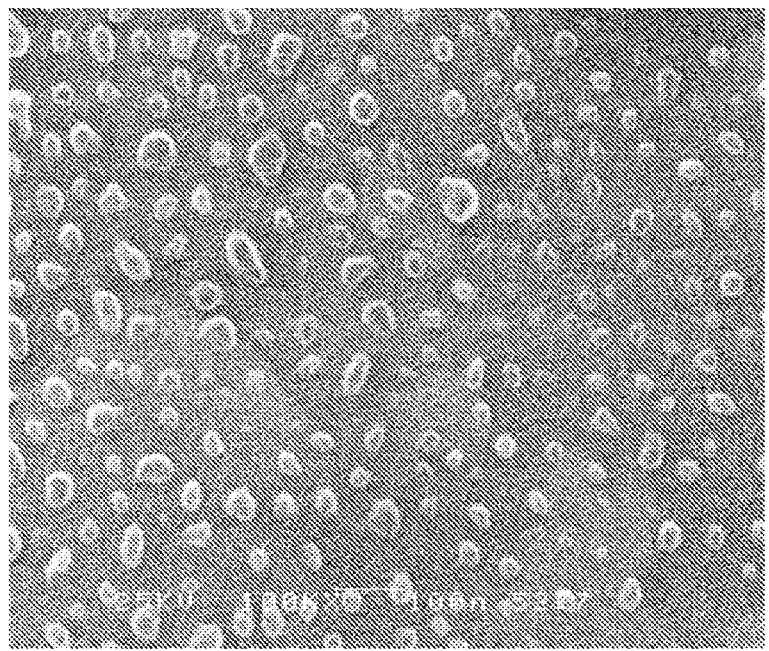

Visualization of individual PEO dendrimers on a planar surface. Cryo-high resolution scanning electron microscopy (cryo-HRSEM) has confirmed that hydrated PEO dendrimers are spherical in projection and can be uniformly distributed in a plane (FIG. 5). These dendrimer-like polymers can function as an artificial molecular channel within a membrane-mimetic structure as well as a cell shape-conforming barrier, thereby providing an opportunity to modulate surface physiochemical properties of barrier films, including an mode for tailoring molecular transport across an immunoisolation barrier.

The stability and biocompatibility of membrane-mimetic films coated on alginate microbeads was evaluated by direct implantation of empty beads into the peritoneal cavity of C57BL/6J mice for periods of up to 8 weeks (103). Film stability was assessed by monitoring the development of film defects in a subgroup of beads in which film coatings were doped with 0.1 mol % of Texas Red labeled polymerizable lipid conjugate. Biocompatibility was determined by inspection of cell adhesion to bead surfaces by light microscopy and by analysis of cell content in the peritoneal fluid using Fluorescence Activated Cell Sorting (FACS). Anti-CD4 and anti-CD8 were used to identify T Cell subsets and anti-CD19 was used for B Cells. Anti-CD11b was used in combination with anti-Ly6G (Gr-1) to identify neutrophils. Macrophages were characterized by their high expression of CD11b, high autofluorescence, and ability to phagocytose fluorescent beads. An inflammatory cell response was not observed by FACS analysis and membrane-mimetic coatings remained largely intact. However, in a minority of microbeads, adhesion of vimentin positive fibroblasts to the film coating was observed during the 8-week implant period, consistent with observed defects in the encapsulation barrier. In comparison, implantation of beads coated with an outer surface of PLL or alkylated terpolymer alone, in the absence of an outer lipid layer, uniformly produced a very robust and early fibroblast cell response. Notably, prior studies from our group and others have demonstrated that membrane-mimetic surfaces, exhibit little protein adsorption or cell adhesion (95, 105-108). However, we have noted that changes in bead diameter can occur during the coating process as a consequence of changes in $CaCl_2$ concentration, which can be capable of inducing inhomogeneities in film coating with exposure of underlying cell reactive PLL and terpolymer. Changes in bead volume can be minimized during the microencapsulation and film coating procedure.

These studies illustrate successful protocols for encapsulating islets in a membrane-mimetic barrier, with preservation of islet viability and function. Transplantation studies in diabetic NOD/SCID mice confirm that euglycemia can be achieved and maintained for prolonged periods in vivo. Finally, membrane-mimetic films are stable in vivo and do not elicit an overt inflammatory response.

Conformal coating of pancreatic islets by electrostatic LbL self-assembly of alginate and poly-L-lysine. Porcine and human islets were conformally coated by brief alternate incubations in aqueous solutions of alginate (Alg; UP LVM, Pronova Biomedical, Norway) and poly-L-lysine (PLL; MW 300 kD). To assess coating efficiency, the film was visualized using confocal fluorescence microscopy after a final incubation with either fluorescein isothiocyanate-labeled PLL (FITC-PLL e.g. (PLL/Alg)$_4$PLL-FITC) or rhodamine B-labeled poly(allylamine hydrochloride) (PAH-RhB; e.g. (PLL/Alg)$_4$PAH-RhB) (data not shown). Uniform coatings were rapidly generated with minimal islet loss and maintenance of islet viability.

Figure 6:
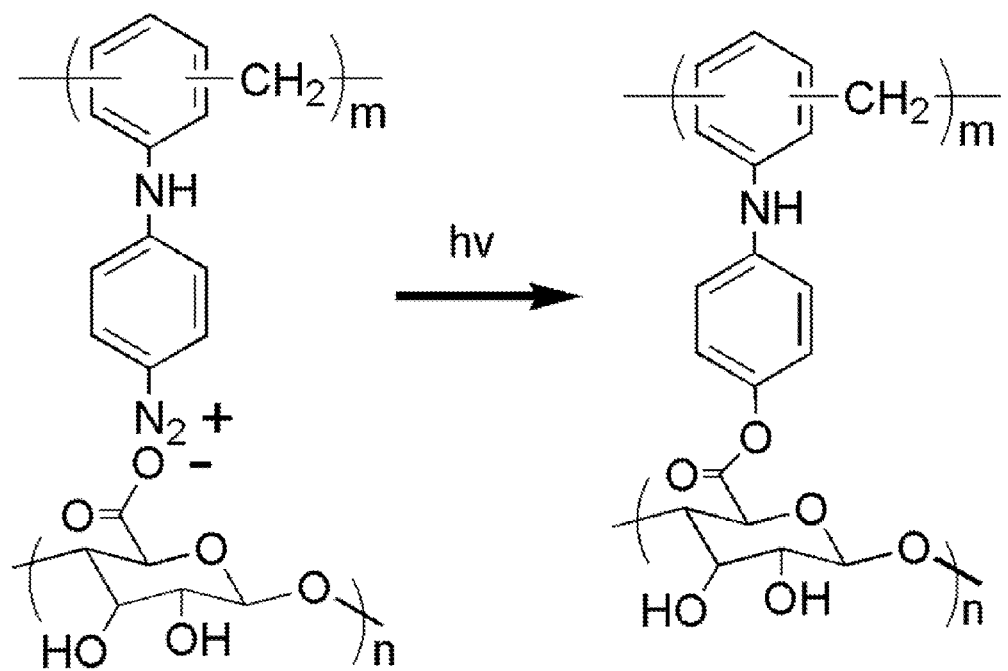
FIG. 6: Diazonium-bearing polymers carry positive charges and can form polyelectrolyte multilayers by sequential adsorption with negatively charged polymers, such as alginate, from aqueous solution. When exposed to light (depicted as "hv"), ionic crosslinks are transformed to covalent adducts.

Multilayer film formation by covalent LbL self-assembly of alginate and a diazonium-bearing polymer. We have recently demonstrated that extremely robust conformal cell coatings can also be generated by electrostatic LbL polymer assembly followed by photomediated covalent crosslinking. LbL polymer films were produced through electrostatic self-assembly of alternating layers of alginate and a synthesized diazonium-bearing polymer (DR). When the latter polymer system is exposed to light, ionic crosslinks between the positively charged diazonium groups and the carboxylate residues of alginate are transformed to covalent crosslinks (75, 112) (FIG. 6).

Figure 7A:
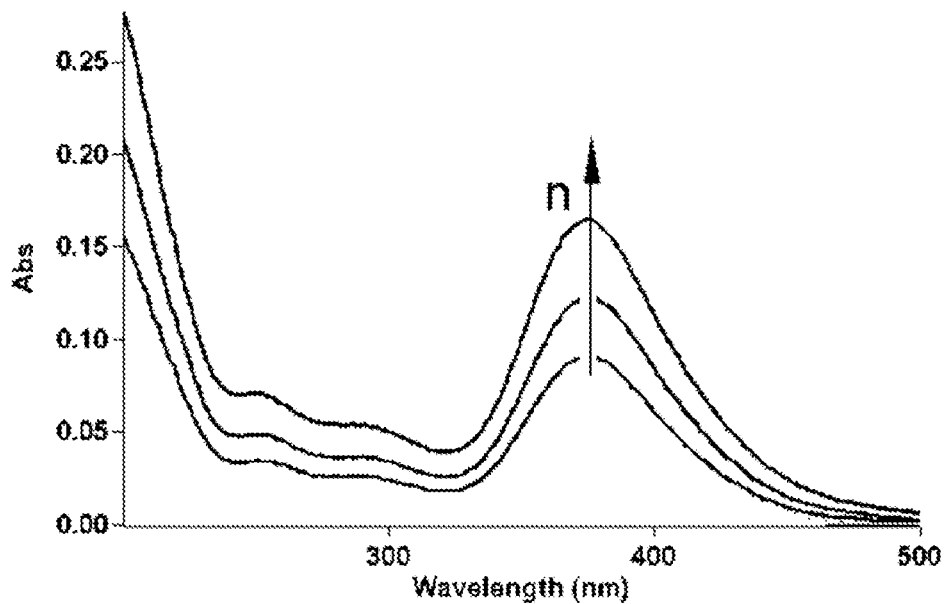
FIGS. 7A-B: (A) UV-vis spectra of $(Alg/DR)_n$ films illustrating the effect of increasing number of polymer layers (n). (B) UV-vis spectra of $(DR/Alg)_4$ films illustrating the effect of increasing irradiation time.
Figure 7B:
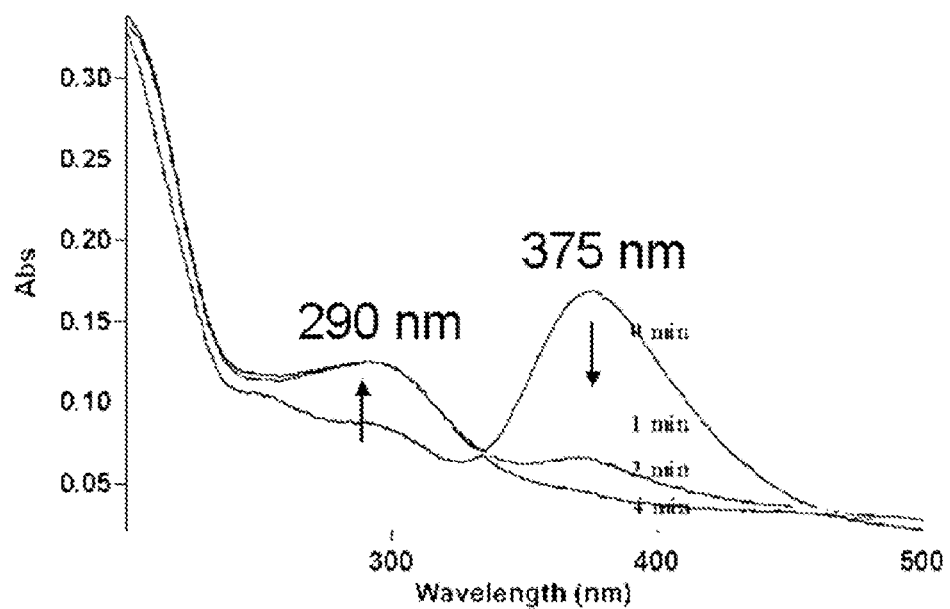

After completion of the desired number of dip cycles in a dark environment, coated quartz substrates were irradiated using a quartz halogen illuminator. The pronounced optical absorbance of DR provides unique insight into the film growth (FIG. 7). For example, the peak at 375 nm in FIG. 7 is associated with the contribution of $\pi$-$\pi$* transition of the diazonium group and increases linearly during formation of a DR/Alg multilayer as a function of dip cycle (n) (FIG. 7A). In the absence of alternating layers of alginate, repeating dip cycles in DR alone does not result in an increase in the absorbance peak at 375 nm, due to a lack of film growth. After irradiation, FIG. 7B demonstrates that the absorption band at 375 nm decreases as a function of illumination exposure period, with complete disappearance of the band within 3 to 4 minutes. The concomitant appearance of a new peak at 290 nm is consistent with the formation of covalent crosslinks between the diazonium and the carboxylate residues. As a simple test system, $Ca^{2+}$ crosslinked alginate microbeads (diameter of 300 µm) were coated with an (Alg/DR)$_4$ multilayer by brief alternate incubations in aqueous solutions of alginate and DR. After irradiation, the alginate core was removed by citrate treatment with the production of stable hollow microcapsules and visualized (data not shown). This system establishes a second complementary approach for the formation of a conformal islet barrier.

Figure 8A:
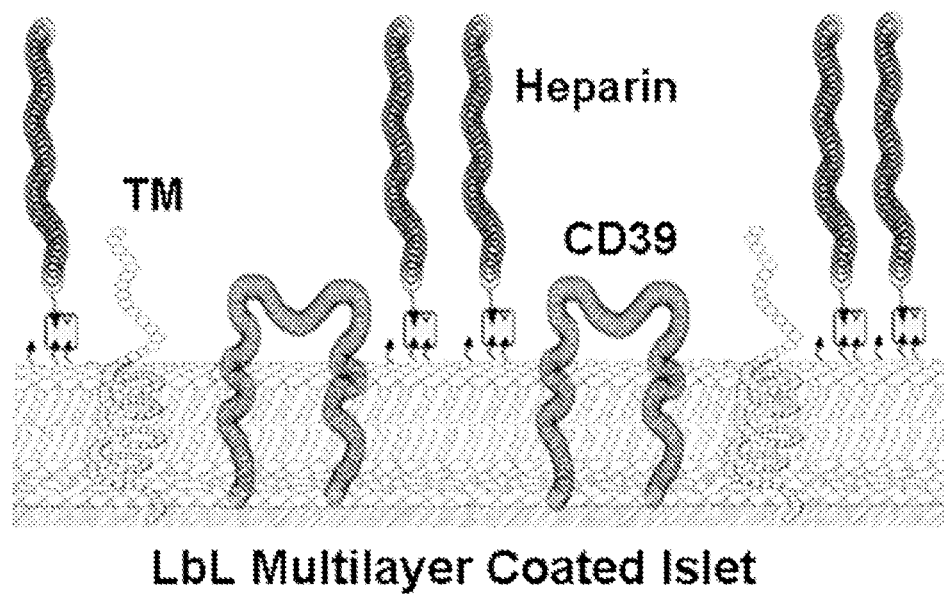
FIGS. 8A-B: Illustration of two techniques to incorporate proteins/carbohydrates into a conformally coated islet encapsulation barrier. (A) Localized within a membrane-mimetic film bound to a polyelectrolyte LbL multilayer. (B) TM, heparin and CD39 containing vesicles bound through biotin/avidin interactions directly to polyelectrolyte multilayer without an intervening membrane-mimetic thin film. Alternatively, proteins can be bound directly to the multilayer without vesicles.
Figure 8B:
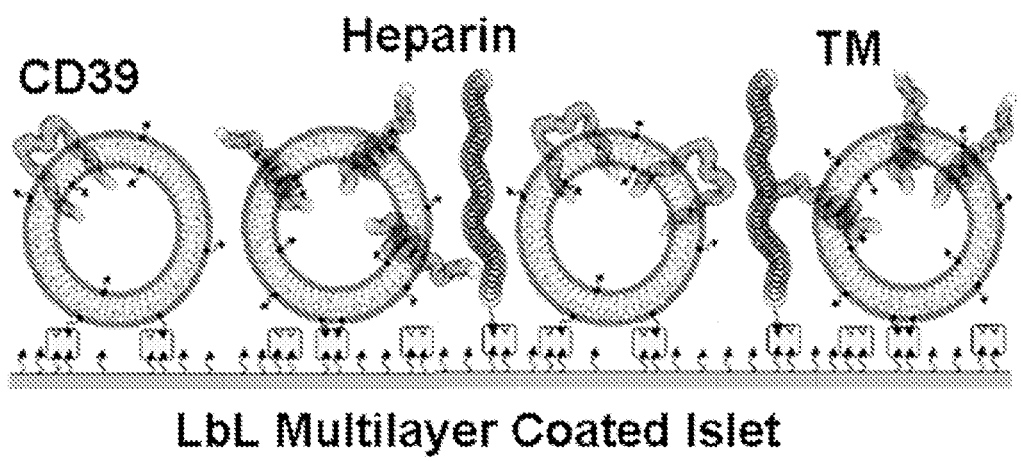
Figure 9:
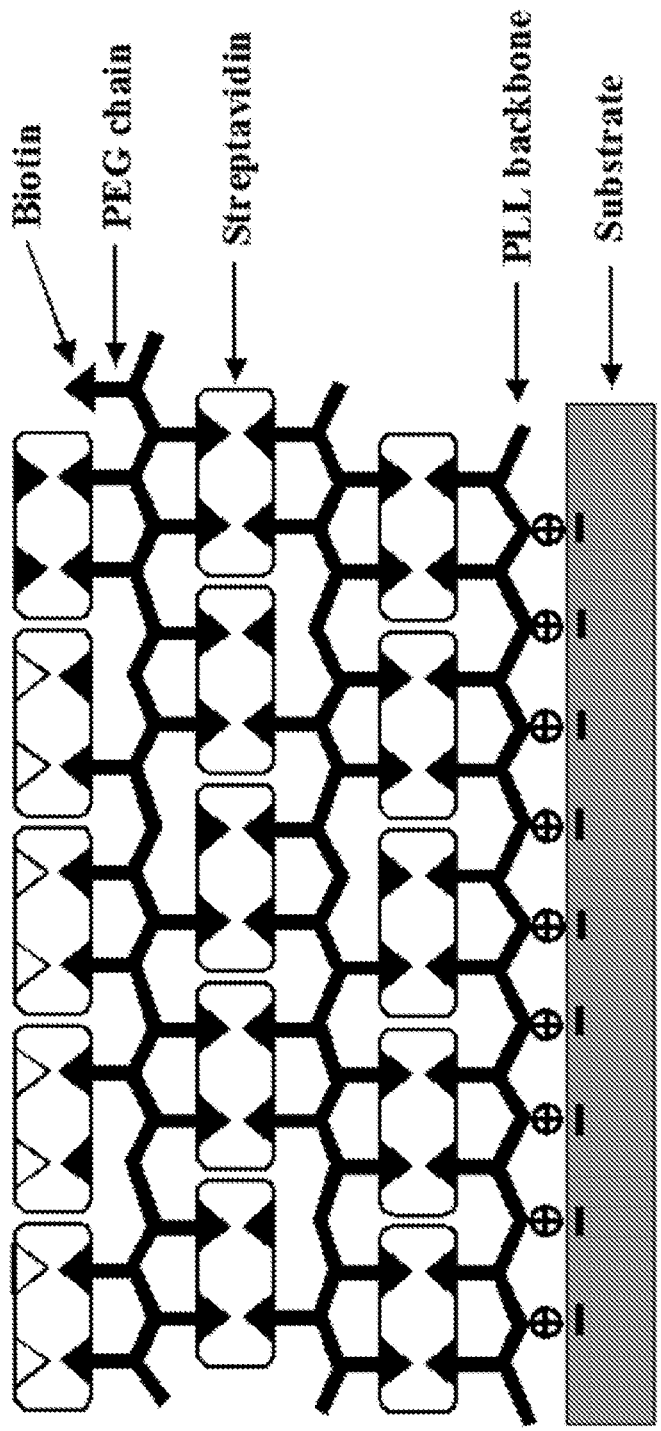
FIG. 9: Schematic illustration of the layer-by-layer assembly of the biotinylated PLL-g-PEG and (strept)avidin multilayer architectures with densely packed PEG mushroom providing resistance to protein adsorption and cell adhesion via biotin/(strept)avidin interaction. PLL-g-PEG adsorbs onto the negatively charged surface via the PLL backbone through electrostatic interaction.

Anti-inflammatory/immunomodulatory proteins and carbohydrates can be incorporated onto a conformal barrier using any of several options. One approach is construction of a conformal islet barrier by alternating oppositely charged layers of alginate (Alg; UP LVM, Pronova Biomedical) and poly-L-lysine (PLL; MW approximately 300 kD) produced and stabilized through electrostatic self-assembly. Alternatively, the coating can consist of alternating layers of alginate and a diazonium-bearing polymer (DR), produced by electrostatic self-assembly, but stabilized by covalent crosslinks. When this polymer system is exposed to visible light, ionic crosslinks between the positively charged diazonium groups and the carboxylate residues of alginate are transformed to form covalent crosslinks (75). A LbL barrier system can be combined with membrane-mimetic film formation, to incorporate TM, heparin, and/or CD39 into a conformal barrier, as shown in FIG. 8A. Another approach involves direct tethering of biotinylated molecules or vesicles to the film surface, as shown in FIG. 8B. As an example of this strategy, we have fabricated alginate-PLL multilayers in which the outermost film layer was doped with a biotin-derivatized alginate. Films were then incubated with Texas Red labeled streptavidin in order to assess the accessibility of biotin binding sites. Confocal microscopy confirms significant streptavidin binding that occurs only in the presence a surface layer of biotin-alginate. Streptavidin did not bind to unmodified alginate (data not shown). Likewise, the use of a PLL-g-PEG-biotin conjugate generates a surface with PEG tethered biotin groups (FIG. 9).

Bioactive molecules can be tethered to a conformal islet barrier. Tethering of intact TM and/or CD39 containing lipid vesicles, as well as heparin binding directly to LBL coated (e.g. islets coated with alginate/PLL alone) via avidin/biotin binding interactions (FIG. 8B). This approach loses some of the advantages provided by the presence of a complete membrane-mimetic film (FIG. 8A), including a second level of control over interfacial transport processes. However, tethering intact functionalized lipid vesicles to conformally coated islets reduces the total number of coating steps and eliminates the requirement for postcoating photopolymerization. Thus, this approach can be more amenable to coating large numbers of islets required for clinical transplantation with minimal islet loss and optimal preservation of islet viability. A variant of this approach encompasses direct derivatization of a polymer LbL coating with both biotinylated heparin and a PEG-TM conjugate, in the absence of either a bound membrane-mimetic film or lipid vesicles.

Generation of Protein C Activating Lipid Assemblies. Localization of thrombomodulin (TM) within a lipid membrane accelerates activated protein C (APC) production by concentrating and coordinating reacting substrates with TM (53). Within this framework we have reformulated TM into vesicles composed of both natural and polymerizable lipids and investigated photopolymerization as a mechanism for enhancing the stability of the TM/vesicle assembly (91, 113). The incorporation efficiency of TM exceeded 95% as determined by sucrose gradient and TM containing vesicles composed of monoacrylate-PC could be polymerized by exposure to visible light in the presence of eosin Y/triethanolamine. Overall, $k_{cat}/K_m$ values reveal that protein C activation is catalytically efficient in polymeric vesicles, despite a modest increase in $K_m$ (Table 1).

TABLE 1

Determination of $K_m$ and $k_{cat}$ for TM as a function of local lipid microenvironment†

|  | Free TM | TM in POPC vesicles | TM in acryl-PC vesicles | TM in polymerized acryl-PC vesicles |
|---|---|---|---|---|
| $K_m$ (μM) | 3.6 ± 1.1 | 0.66 ± 0.14 | 0.86 ± 0.10 | 4.5 ± 0.9 |
| $K_{cat}$ (min⁻¹) | 7.0 ± 1.0 | 4.6 ± 0.2 | 2.6 ± 0.1 | 5.7 ± 0.6 |
| $k_{cat}/K_m$ (min⁻¹·μM⁻¹) | 1.94 | 6.97 | 3.02 | 1.27 |
| $K_m$ (μM) (Ref. 60) | 7.5 | 0.7 | NA | NA |

†Rabbit TM, human protein C, and human thrombin were utilized.

Figure 10A:
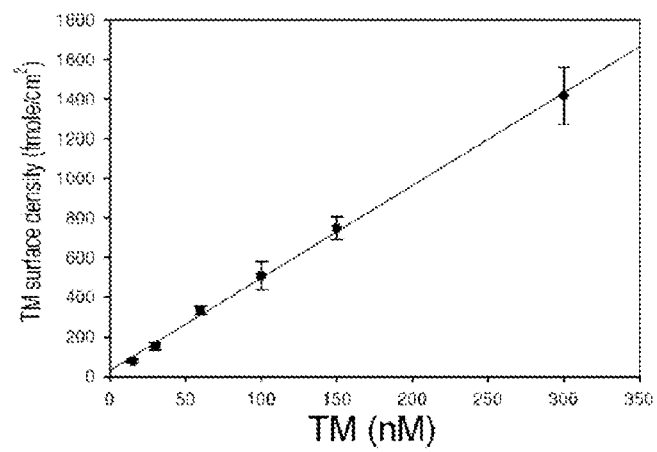
FIGS. 10A-C: (A) TM surface density as a function of molar concentration of TM in a TM/vesicle solution. (B) Rate of APC production from a TM containing substrate (Sample) and endothelial cell (EC) monolayers from human umbilical venous EC (HUVEC), bovine arterial EC (BAEC) and human dermal microvascular EC (HDMEC). (C) Concentration of activated protein C as a function of TM surface density was measured at two shear rates (50 and 500 $s^{-1}$).
Figure 10B:
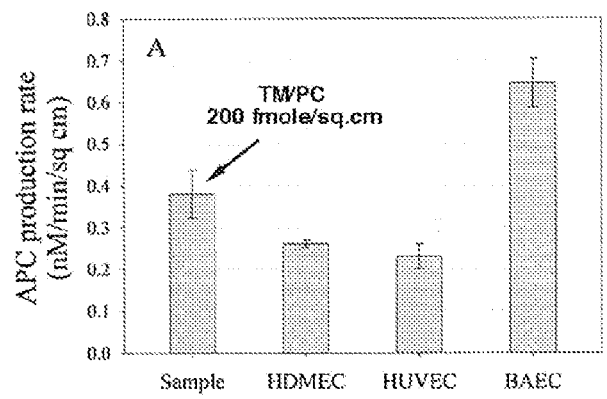
Figure 10C:
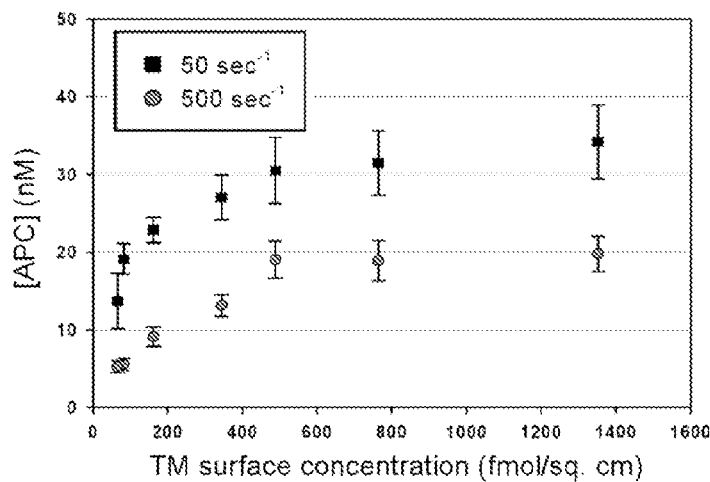

Relationship of TM surface concentration to protein C activation rate. Non-polymerized lipid vesicles can be fused onto an alkylated alginate/PLL multilayer to create a bioactive, TM containing supported lipid bilayer that is subsequently stabilized by in situ photopolymerization (91). TM containing polymerized membrane-mimetic surfaces were prepared on alginate/PLL substrates using varying molar concentrations of $^{125}$I-labeled-TM/vesicle solutions (91). A linear relationship was observed between TM surface content and the molar concentration of TM in the aqueous solution (FIG. 10A) and a commensurate increase in the rate of protein C activation was noted. At a TM density of 200 fmole/cm², the rate of APC production is comparable to that produced by monolayers of venous (HUVEC), arterial (BAEC), or microvascular (HDMEC) endothelial cells (FIG. 10B). Moreover, we demonstrated that a mass transfer limited regime was achieved at TM surface concentrations, which exceeded 600 fmol/cm² (FIG. 10C). In other words, the rate of APC generation was primarily dependant on the concentration of protein C and its transport to the surface and independent of TM surface concentration. Concentrations of activated protein C observed in the mass transfer limited regime were approximately three orders of magnitude greater than that normally observed in vivo (20-80 pM) (114, 115).

Figure 11A:
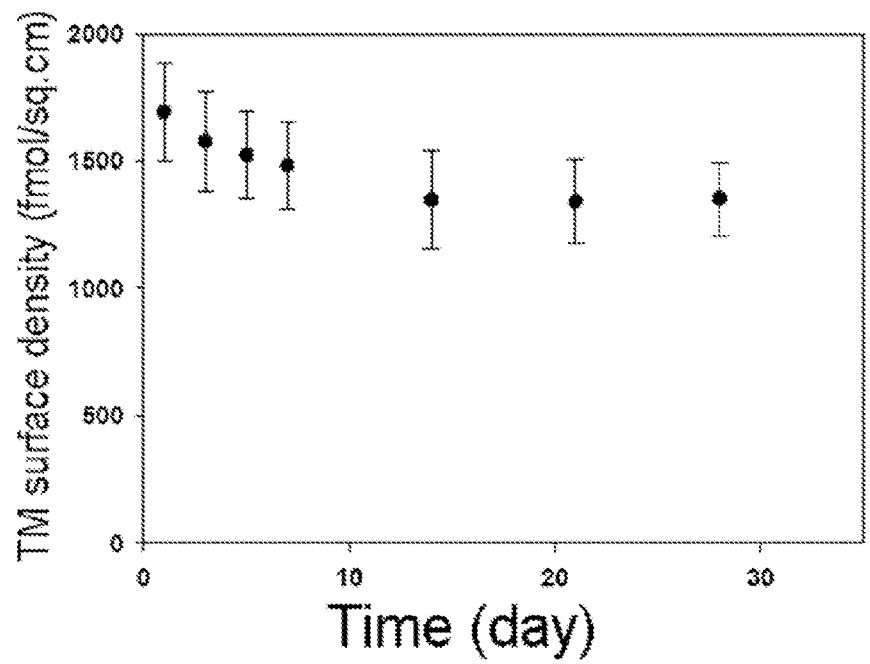
FIGS. 11A-C (A) TM surface density as a function of incubation time in PBS at 37° C. (B) Duration of TM activity in human plasma at 37° C. at two shear rates. (C) The rate of thrombin production over time in the presence of lipid vesicles with TM (60 and 100 nM) or without TM. Similar results were observed with planar films.
Figure 11B:
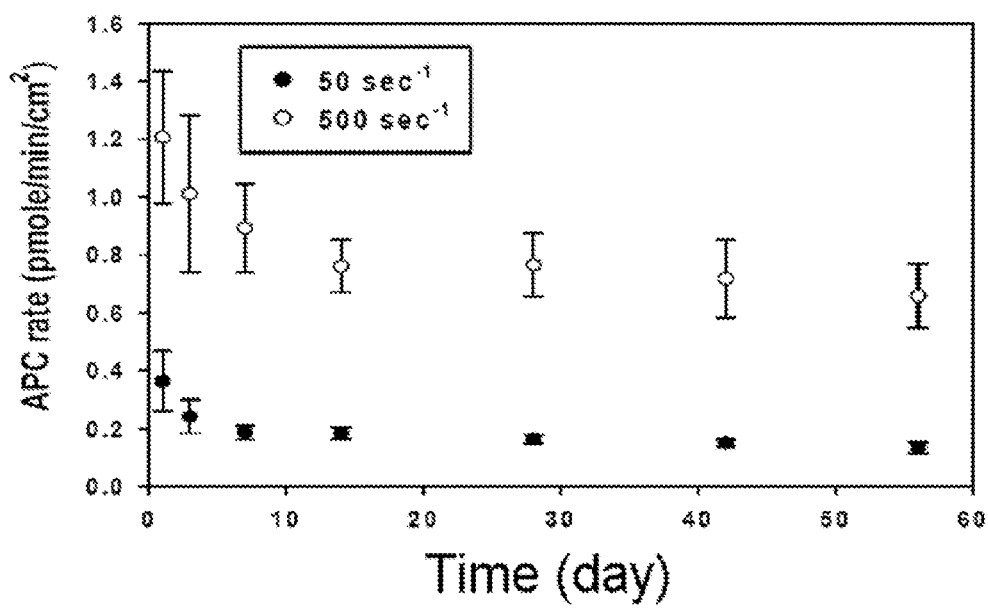
Figure 11C:
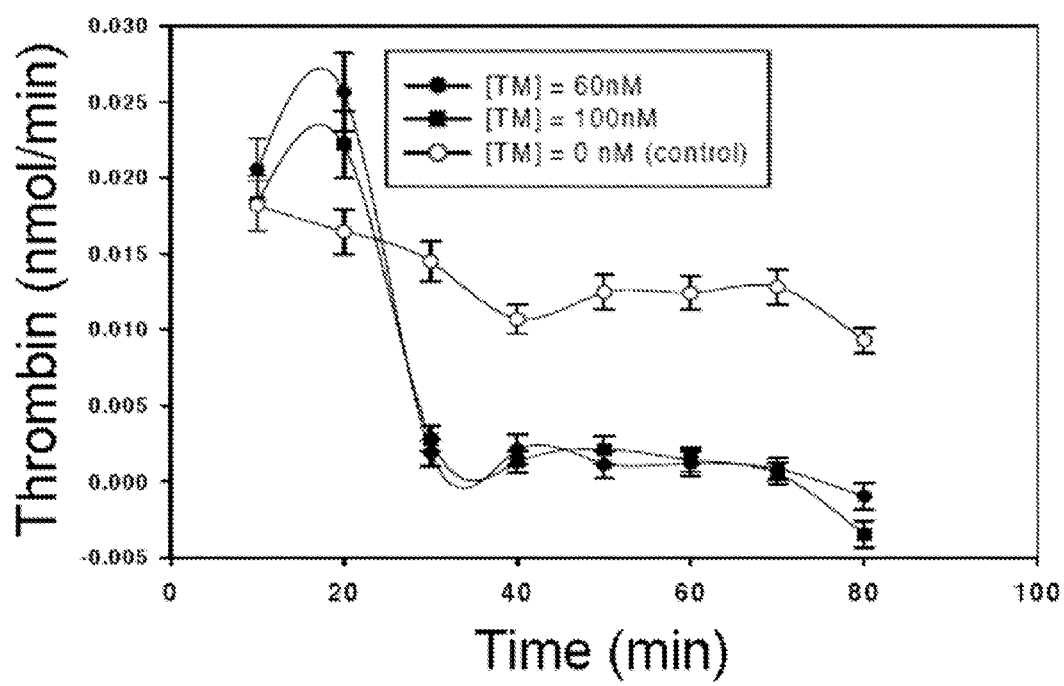

The stability of TM containing films was initially assessed by incubating test samples in PBS at 37° C. We observed an initial loss of ~20% of $^{125}$I-labeled-TM during the first week of incubation, which we attribute to the loss of unfused TM containing vesicles (FIG. 11A). Little change in TM surface concentration was observed thereafter over incubation periods exceeding 30 days in PBS at 37° C. As a surrogate assessment of the durability of catalytic activity in vivo, TM containing lipid films were incubated in human plasma at 37° C. with fresh plasma exchanges three times each week. An initial decrease in the rate of APC production over the first week was observed, which was consistent with the loss of unfused vesicles. As illustrated in FIG. 11B, the rate of APC production has been very stable for periods exceeding two months with ongoing measurements confirming undiminished activity that now extend beyond three months. The capacity of TM containing lipid assemblies to inhibit thrombin generation in an artificial protein plasma mixture was confirmed using both polymerized TM/lipid vesicles, as well as a TM containing membrane-mimetic planar lipid assembly produced on an Alg/PLL coated glass slide (FIG. 11C) (91).

Figure 12:
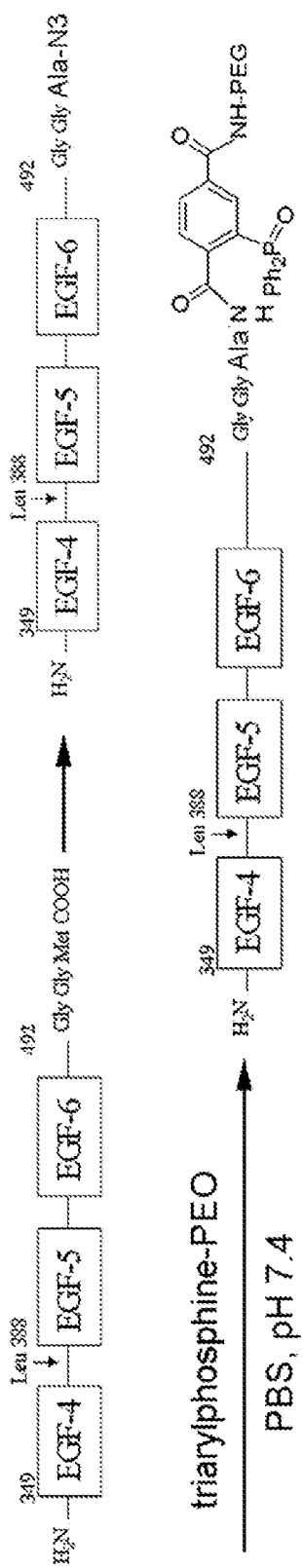
FIG. 12: Biosynthesis of a truncated human TM with a C-terminal Ala-$N_3$ and chemical modification with PEO.

Synthesis of a PEO-TM conjugate for immobilization onto an islet barrier. As an additional strategy for incorporating TM into thin films, we have used genetically directed synthesis to create a short TM construct containing the catalytic region of EGF domains 4-6. In the process, we synthesized an azido ($N_3$)-functionalized alanine analog and incorporated this non-natural amino acid biosynthetically into the TM construct as a C-terminal linker (FIG. 12). Through Staudinger ligation with a suitable PEO derivative (MW 3000), a TM-PEO conjugate was created. The TM construct and TM-PEO conjugate have been fully characterized by Western blotting and SDS-PAGE. The catalytic activity ($k_{cat}$, $K_m$) of the TM-PEO conjugate was identical to the TM mutant alone, as well as a commercially available soluble TM protein (Table 2). Use of a biotin or diene terminated PEG derivative can facilitate rapid and direct coupling of the TM catalytic site to a barrier surface.

TABLE 2

| | TM Catalytic Activity | | |
|---|---|---|---|
| | $K_m$ (μM) | $k_{cat}$ (min⁻¹) | $k_{cat}/K_m$ (min⁻¹ μM⁻¹) |
| Human TM Ala-$N_3$ analogue | 1.0 ± 0.5 | 0.16 ± 0.05 | 0.16 ± 0.05 |
| TM-PEG conjugate | 1.0 ± 0.5 | 0.20 ± 0.05 | 0.20 ± 0.05 |
| Commercial soluble human TM | 0.7 ± 0.1 | 0.14 ± 0.02 | 0.21 ± 0.02 |

Figure 13:
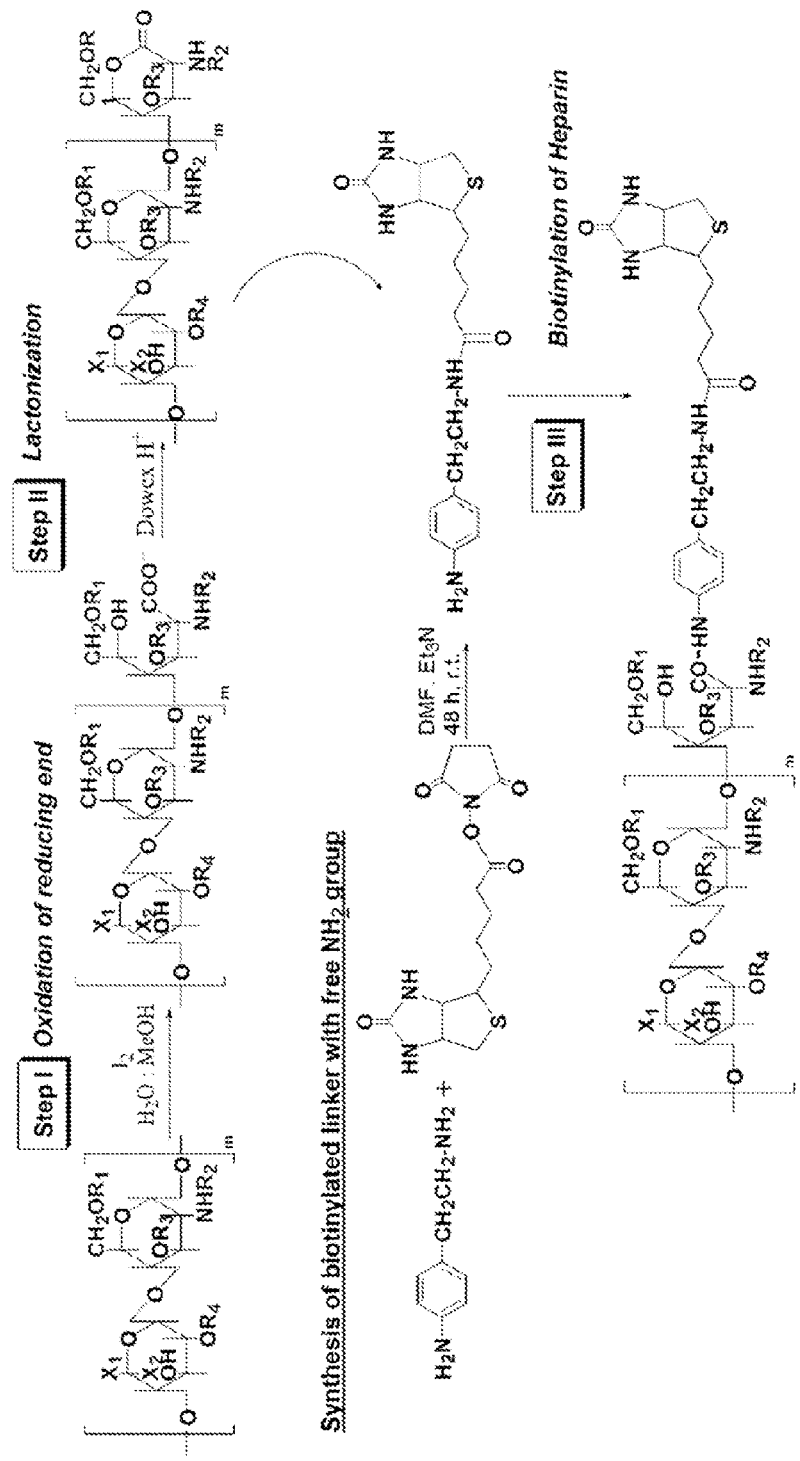
FIG. 13: Synthesis of a biotin-terminated heparin conjugate.
Figure 14:
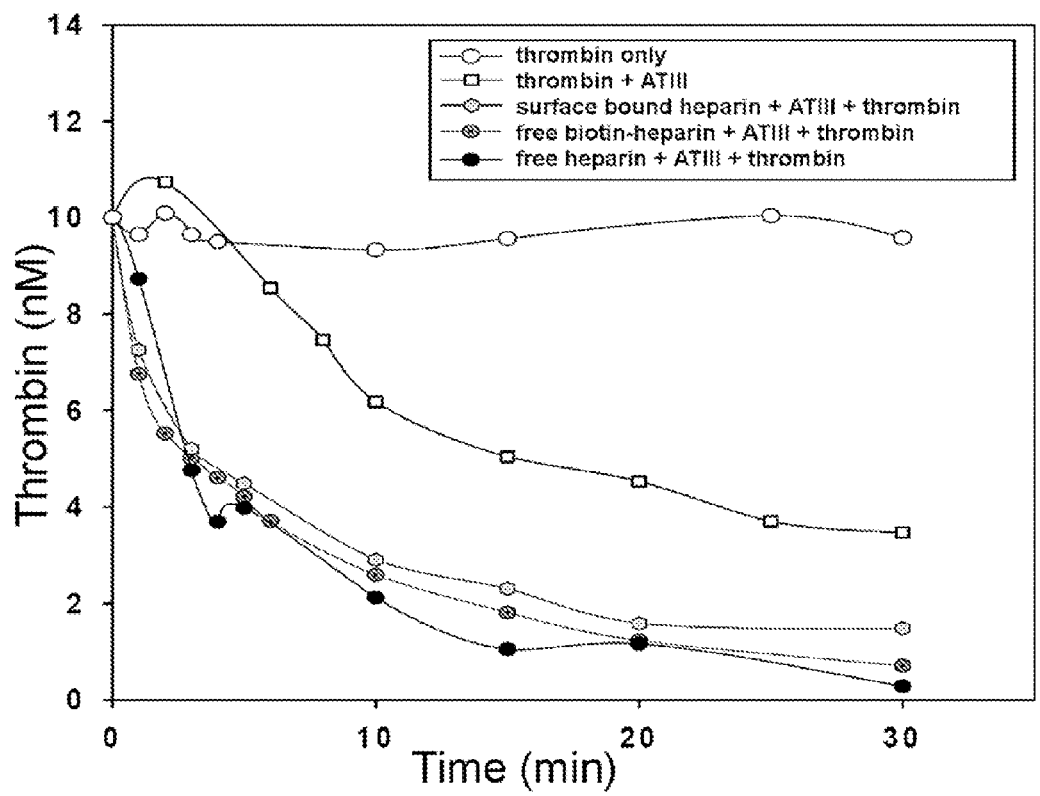
FIG. 14: Rate of thrombin inactivation over time illustrating surface bound heparin maintains efficacy.
Figure 15:
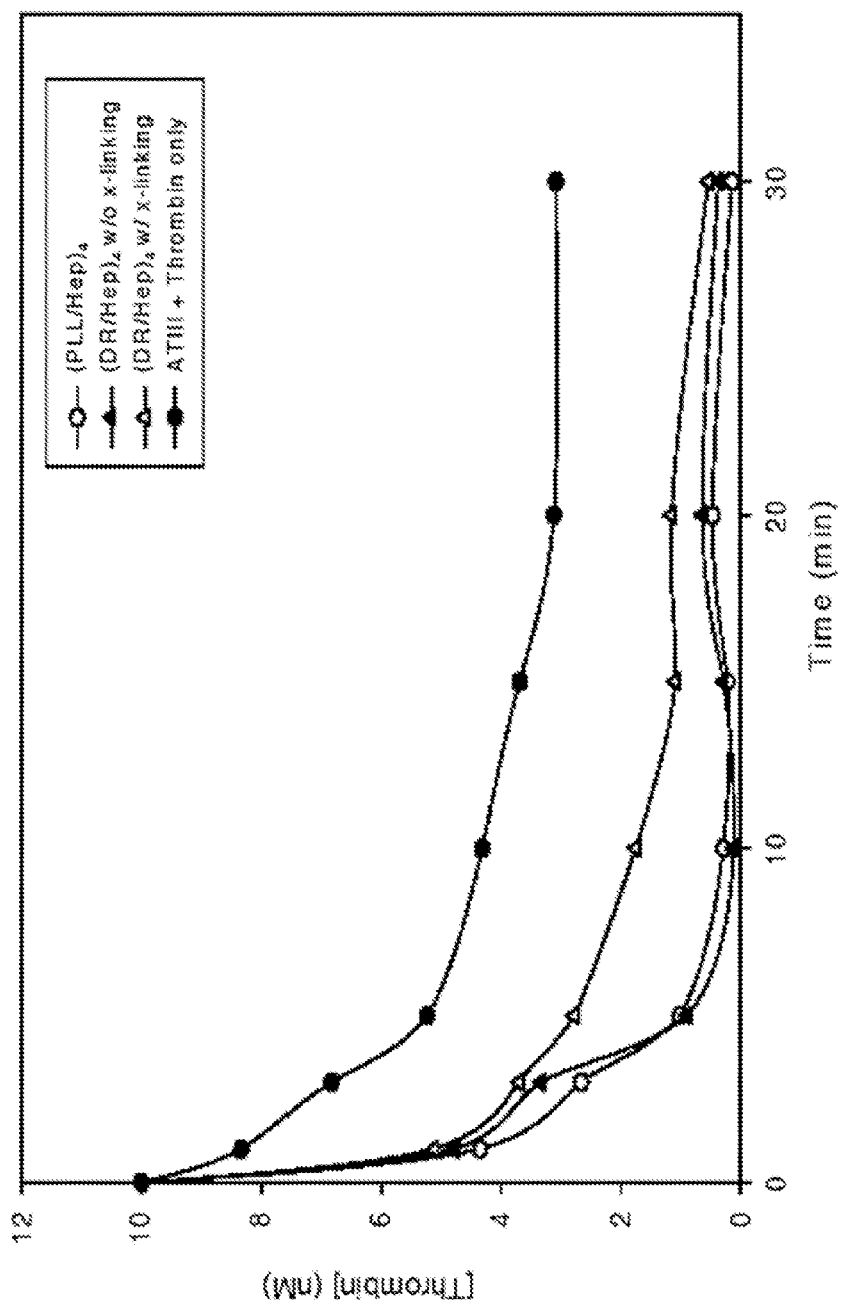
FIG. 15: Thrombin activity as a function of time after incubation of various planar substrates in solutions containing ATIII and thrombin. Heparin containing polyelectrolyte multilayers (containing cross-links generated by photoactivation) enhances the ability of antithrombin III to inhibit thrombin.

Synthesis and activity of a biotin-heparin conjugate. A biotin-terminated heparin conjugate was synthesized (MW 10 kD, Sigma) as outlined in FIG. 13 with an overall yield of 60%. Anti-thrombin activity was assessed by incubating test samples at a final concentration of 1 μM in Hepes buffer at 37° C. along with thrombin (10 nM) with or without ATIII (200 nM). At timed intervals, aliquots were removed and quenched by Tris buffer containing EDTA and chromogenic substrate S-2238 (Chromogenix, Italy). The amount of thrombin remaining in solution was determined by measuring absorbance at 405 nm. As summarized in FIG. 14, the activity of the biotin-heparin conjugate was identical to that of unmodified heparin. In a similar manner, biotin-heparin conjugates were bound to test surfaces (circular glass slide, d=18 mm) containing 5 mol % streptavidin, and the surface was washed extensively to remove unbound heparin. Test surfaces were then incubated at 37° C. in Hepes buffer along with thrombin and ATIII, as described above, and thrombin levels measured as a function of incubation time. As illustrated (FIG. 14), the surface bound biotin-heparin conjugate was capable of accelerating the rate of ATIII-mediated thrombin inactivation. This conjugate provides an efficient means for adding a surface bound layer of heparin to conformally coated islets. A similar affect was observed for heparin containing polyelectrolyte multilayers generated by electrostatic interactions (PLL/Hep)$_n$ and by photomediated crosslinking (DR/Hep)$_n$ (FIG. 15).

We have expressed and purified human CD39 from *Pichia pastoris* and confirmed both ecto-ATPase and ecto-ADPase activity. Moreover, we have demonstrated an increase in catalytic activity upon reconstitution of CD39 in synthetic lipid vesicles. Briefly, the plasmid carrying the CD39 human coding sequence was provided by Dr. Simon C. Robson (Harvard Medical School, USA). Polymerase chain reaction (PCR) was utilized to add a Kozak sequence flanked by EcoRI to the 540 end of CD39 and a FLAG tag flanked by XbaI to the 3' end of CD39. The construct was harbored in pCR 2.1-TOPO (Invitrogen, San Diego, Calif.) and multiplied in One Shot Top10 (Invitrogen). To express CD39 in yeast, the EcoRI/XbaI digestion product was cloned into pPICZ (Invitrogen) and transformed into *Pichia pastoris* strain SMD1168 (Invitrogen). The expression construct was confirmed through DNA sequencing analysis. *P. pastoris* cultures were grown at 30° C. and expression induced for 4 days with 0.5% methanol. Cells were harvested, resuspended in breaking buffer, and cell lysates centrifuged to separate membrane and soluble fractions. Western blot analysis with CD39 mAb BU61 (An-Cell Co., Bayport, Minn.) revealed all native CD39 to be expressed exclusively in yeast membrane fractions. CD39 was extracted from membrane fractions using 1% Igepal CA-630 and purified on anti-FLAG M2 affinity columns (Sigma, Saint Louis, Mo.). Kinetic parameters were measured for both detergent-solubilized CD39 and for protein reconstituted in POPC lipid vesicles at varying molar ratios of CD39 to lipid (1:85,714, 1:33,613, 1:16,806). The reaction was started by the addition of substrate (ATP or ADP) at concentrations between 50-1500 µM. Inorganic phosphate was measured as described by Ames (116). As summarized in Table 3, reconstitution of CD39 in lipid vesicles is associated with a reduction of Km of nearly an order of magnitude with a significant increase in both ADPase and ATPase catalytic activity.

The experiments contained herein illustrate that a conformal islet barrier of varied type and composition can be generated by LbL polymer assembly. In addition, we have demonstrated that membrane-based immunomodulatory and anti-inflammatory molecules, such as thrombomodulin, heparin, and CD39, can be manipulated in a manner that facilitates their controlled incorporation into a cell encapsulation barrier. All told, a rational design strategy has been presented so that an "actively" anti-inflammatory barrier can be disposed on cell surfaces prior to transplantation to reduce early graft injury and later induction of an immune response.

Assessing barrier effectiveness. LbL polymer films produced on silicon wafers can be investigated by molecular level techniques to assess physiochemical properties, including UV-vis and external reflectance IR spectroscopy, electron spectroscopy for chemical analysis (ESCA), and high-resolution scanning electron microscopy (HR-SEM). Film thickness is determined by ellipsometry. Data from these films permit optimization of barrier parameters including selection of polymer concentration and molecular weight (e.g. alginate or PLL), as well as solvent conditions (e.g. culture medium), which influence film growth relevant to the formation of a conformal islet coating. All told, a process that requires the fewest number of LbL polymer adsorption steps to generate a uniform coating with a thickness in the range of 5-20 µm can be used for subsequent studies with mouse (B10.BR strain) and/or porcine islets. In an embodiment the uniform coating has a thickness less than approximately one micron.

Avidin is incorporated into the outermost layers of alginate for those systems in which biotinylated vesicles or heparin is bound to the surface of an LbL film. A previous report has documented that, as a positively charged protein, avidin can be stably incorporated into polymer films by electrostatic self-assembly (117). The surface concentration of avidin can be defined by radiochemical titration of $^{125}$I-avidin and its spatial distribution characterized using FITC-avidin in conjunction with confocal fluorescence microscopy. The capacity of avidin to bind biotinylated heparin and vesicles is determined as a function of avidin surface concentration using fluorophore-labeled molecules (e.g. biotin-FITC, biotin-heparin-FITC, or biotin-lipid vesicles doped with 1 mol % FITC-lipid). Nonspecific surface adsorption is assessed using related, non-biotinylated molecules.

Surface thickness and uniformity of a conformal barrier on a cell surface is assessed by confocal fluorescence microscopy. Specifically, FITC-labeled PLL can be incorporated as a marker polymer within the LbL multilayer and film thickness determined by area and pointwise measurements using at least 50 coated cells, as detailed elsewhere (109). In selected coated cells, the spatial distribution and concentration of surface accessible avidin can be defined using biotinylated molecules that are conjugated to a fluorescent or radiochemical label, respectively. Viability of conformally

TABLE 3

Determination of Km and kcat for CD39 as a function of local lipid microenvironment

|  | Free CD39:ADPase activity | Free CD39:ATPase activity | CD39 in POPC vesicles:ADPase activity† | CD39 in POPC vesicles:ATPase activity† |
|---|---|---|---|---|
| $K_m$ (µM) | 45.8 | 58.5 | 6.5 | 5 |
| $k_{cat}/K_m$ (min$^{-1}$·M$^{-1}$) | $3.9 \times 10^5$ | $3.4 \times 10^5$ | $2.2 \times 10^6$ | $1.8 \times 10^6$ |

†Data illustrated for vesicles comprised of a molar ratio of CD39:POPC of 1:33,613.

encapsulated cells (e.g. porcine and mouse (B10.BR strain) pancreatic islets) can be evaluated 24 h after encapsulation using the Live/Dead Viability-Cytotoxicity Kit (Molecular Probes). Percent viability can be graded, as detailed elsewhere (109). Cell function can be assessed by monitoring insulin release (ng/min/islet) by radioimmunoassay after a static glucose challenge. Small gaps in the conformal barrier can be indirectly detected by an in vitro assay for complement permeation and killing. It is important to minimize small gaps in the conformal coating barrier to prevent or minimize coated-islet destruction after transplantation. Islet viability can be measured before and after exposure to rabbit complement (109). Briefly, islets in 100 µL of RPMI 1640 are placed in a well of a 96-well plate and 100 µL of rabbit complement (Pel-Freez, sterile 3 to 4-week-old rabbit complement) added. Following a 1-h incubation, islets are washed in PBS, and viability determined. Control islets are incubated with heat-inactivated complement. Of note, this assay is reflective of barrier defects and not permselectivity, since complement proteins degrade rapidly at room temperature and exposure is brief (1 h).

In vivo biocompatability can be assessed using empty capsules. Empty capsules are produced by coating alginate beads with a LbL polymer film followed by citrate treatment to remove the alginate core. We have previously determined that the majority of islets are approximately 200-300 µm in diameter. Therefore, alginate beads in this size range, produced using an electrostatic bead generator, are used. Approximately 250 empty capsules are injected into the portal circulation of C57BL/6J mice and in vivo plasma markers, which are elevated upon activation of platelets and coagulation enzymes, are monitored over a 48 h period. We have chosen this quantity of capsules to approximate the estimated number of islets that will be needed to achieve euglycemia. After capsule infusion, thrombin formation is determined by measuring levels of thrombin-antithrombin III complexes (Dade Behring, Germany). Consumption of fibrinogen and its cleavage by thrombin is assessed by measurements of fibrinogen and fibrinopeptide A (FPA) levels (American Diagnostica, Conn.). Activation of platelets is assessed by the change in platelet count and by plasma levels of the releasable platelet α-granule protein, β-thromboglobulin (Diagnostica Stago, N.J.).

In addition to plasma markers of coagulation, the local hepatic inflammatory response is assessed by light microscopy and immunohistochemistry at 1, 3, 7, 14, and 28 days after infusion of empty capsules. Specifically, liver sections are embedded in freezing medium, serially sectioned, and fixed in 2% acetic acid (vol/vol)/10% buffered formalin to wash out non-crosslinked fibrinogen/fibrin (118). The following primary antibodies are used: anti-myeloperoxidase (NeoMarkers, rabbit anti-mouse polyclonal), as a marker for neutrophil infiltration and MOMA-2 (Research Diagnostics, rat anti-mouse monoclonal), as a marker of mouse monocyte and macrophage infiltration. In addition, the presence of a local intraportal coagulant response is determined by staining with rabbit anti-fibrin(ogen) antibody (Dako Corp, Calif.; cross-reacts with mouse fibrin), as well as rat anti-mouse CD-41 (MWReg30; BD Pharmingen) and CD62p (RB40.34, BD Pharmingen), which recognize platelet GPIIb/IIIa complex and P-selectin, respectively. Negative control slides are incubated with nonimmune immunoglobulin under the same conditions.

In vivo biostability. Although a temporary film coating may be sufficient to counteract the acute adverse effects of a blood mediated inflammatory response and enhance islet engraftment, the presence of a durable anti-inflammatory coating may yield a useful adjunct to standard immunosuppressive regimens and potentially improve long-term islet survival. Thus, the biostability of empty capsules, which do not elicit a procoagulant/pro-inflammatory response, are characterized after portal vein infusion by direct capsule visualization by light and fluorescence microscopy 2, 4, and 8 weeks after implantation. Fluorescence imaging is performed on specimens in which FITC-PLL is incorporated into the barrier wall. As an additional marker of barrier integrity, capsules are loaded with quantum dot-labeled IgG (Quantum Dot, Inc.) and intracapsular retention assessed by fluorescence microscopy. A "brush-border" like layer of PEO can be coupled to the outer surface of the polymer coating to reduce non-specific protein and cell adsorption. Alternative biopolymers for multilayer formation are available. For example, heparin or hyaluronan can substitute for alginate as negatively charged polymers. Of interest, hyaluronan decreases the activity of neutrophils and stimulates the differentiation of macrophages into a non-cytocidal, non-inflammatory subpopulation (123, 124). Likewise, chitosan can be substituted for PLL.

As a positively charged protein, prior reports have documented that avidin incorporates into polymer films by electrostatic self-assembly (117). In addition, a number of examples now exist in which molecules that carry no net charge can be entrained within a polymer multilayer, otherwise generated by electrostatic self-assembly. Therefore, other biotin binding proteins, such as streptavidin, may be utilized. In addition, commercial sources exist for biotin derivatized hyaluronan, alginate, and heparin that can be co-mixed with non-derivatized alginate as an alternate means to present surface biotin groups as avidin/streptavidin binding sites.

Immunogenicity of avidin. Avidin (as well as streptavidin) and biotin have been used in the design of a number of novel drug delivery applications and extensive animal investigations suggest that these compounds are well tolerated (125). In addition, as a component of an islet barrier, surface bound avidin is not delivered in soluble form or in repeated doses. Therefore, an immunogenic response to avidin, especially when complexed to another biomolecule or vesicle, is avoided. An antibody response to avidin could affect long-term islet survival. Serum antibody levels to avidin are measured to assess antibody response. Briefly, recipient mice are tail bled 15, 30 and 45 days after transplantation and the serum (1:10 dilution) incubated with avidin derivatized polystyrene microbeads (Polysciences) at room temperature for 30 min. Beads are washed and incubated with anti-mouse IgG FITC-conjugated antibody (1:100 dilution) for 30 min at room temperature. Beads incubated with the secondary antibody only are used to determine background fluorescence. The avidin-specific antibody (ab6675; Abcam, UK) are used as a positive control and normal mouse serum as negative control. The beads are washed and fixed in 1% paraformaldehyde and flow cytometry performed to assess mean channel fluorescence of each individual serum sample. If an antibody response is detected, alternative coupling strategies to biotin exist. For example, aminooxy, hydrazide, and thiosemicarbazide groups, are all capable of reacting under physiologically benign conditions to form a stable covalent adduct with ketone groups. Indeed, these schemes have been used to selectively decorate the surface of living cells with unique organic compounds (126, 127).

Permeability control of LbL polymer assembly. The conformal cell-coating by LbL polymer assembly can permit free exchange of glucose, insulin and other essential nutrients, while excluding entry to IgG (MW 150 kD), complement (MW>79 kD), and free shedding of tissue factor. In this regard, although the molecular weight of tissue factor (TF) is 47 kD, Moberg and colleagues (37) have noted that TF activity appears to be completely associated with much larger shed lipid microparticles. Release of tissue factor by conformally coated islets is assessed in culture by direct ELISA measurements (American Diagnostica, Conn.), as well as by measuring rates of thrombin generation. The latter is performed by incubating coated islets in a defined plasma protein solution for 30 min, quenching with EDTA, and measuring thrombin generation using the chromogenic substrate S-2238 (128). Transport characteristics of polymer multilayers are characterized by calculating mass transfer and permeability coefficients for diffusing species ranging in molecular weight from $10^2$ to $10^5$. Model films are produced on empty alginate microbeads, after which the core is liquefied by citrate treatment, and the capsules incubated in phosphate buffered saline (PBS) at 37° C. The uptake and release of $^{125}$I-labeled markers of varying size (e.g. glucose 180 MW, vitamin B12 1300 MW, insulin 11 kD MW, carbonic anhydrase 29 kD MW, bovine serum albumin 66 kD MW, IgG 150 kD MW) is measured at regular intervals. The unsteady-state diffusion of the marker is analyzed, as described by Skelland (129) and the overall mass transfer coefficient determined (130). In one embodiment, the molecular weight cutoff (MWCO) is between 50 to 100 kDa for conformal islet barriers. PEO dendrimers are utilized, as necessary, to modulate barrier permeability of LbL polymer films. Film permeability can be modulated either by altering the number of multilayers, by utilizing polymers of different molecular weight, and/or by use of PEO dendrimers, as described. However, even in the absence of a defect free film or perfect permselectivity, the capacity to enhance the anti-inflammatory properties of the islet microenvironment via incorporation of proteins and/or carbohydrates can be beneficial to engraftment and long-term cell transplantation survival.

Coating barriers of the present invention elicit minimal non-specific inflammatory and/or pro-coagulant responses, limit release of islet associated tissue factor, and exclude access to IgG and complement. In order to assess whether the presence of a conformal polymer coating enhances portal islet engraftment in the absence of either surface bound TM or heparin, we use a mouse model of primary islet nonfunction (29). The minimum number of islets required to achieve euglycemia in a streptozotocin treated C57BL/6J mouse model is defined using both B10.BR mouse islet allografts and porcine islet xenografts. Briefly, initial dose-response studies are conducted in which streptozotocin treated C57BL/6J mice are divided into five groups (n=8), each receiving either 100, 150, 200, 250, or 300 islets by intraportal injection. The proportion of animals that become euglycemic as a function of time is defined for each group. After identification of the minimum number of uncoated islets that is necessary to consistently achieve euglycemia (estimated ~250 islets), the effectiveness of a given coating strategy is measured using doses of islets that falls below that for which euglycemia is predictably achieved. A beneficial effect is defined by an increase in percentage of successful grafts and/or a reduction of the lag time to normoglycemia.

Rates of engraftment are correlated with plasma markers of platelet activation and thrombin generation during the initial 48-hour period after intraportal islet infusion. As described, thrombin formation is determined by measuring levels of thrombin-antithrombin III complexes and consumption of fibrinogen is assessed by measurement of fibrinogen and fibrinopeptide A levels. In addition, both platelet count and β-thromboglobulin are measured. Graft function is monitored daily by measurement of random blood glucose for 2 weeks and then weekly. Graft rejection is defined as a random blood glucose >250 mg/dL for 2 consecutive days. The portal inflammatory response to coated and uncoated islets is analyzed at 1, 3, 7, 14, and 28 days and then at monthly intervals by immunohistochemistry, FACS, and PCR analysis.

Light microscopic and immunohistochemical characterization of inflammatory cell responses. Liver sections are embedded in freezing medium, serially sectioned, and fixed. Using an alkaline phosphatase strepavidin system (DAKO, Denmark), the following primary antibodies are used: anti-myeloperoxidase (NeoMarkers, Calif.), as a marker for neutrophils; MOMA-2 (Research Diagnostics), as a marker of mouse monocyte and macrophages; anti CD3 (145-2C11; RDS Inc., MN, rat anti-mouse monoclonal), as a marker of total T cells; and anti CD45R (RA3 6B2; BD Pharmingen), as a marker of total B cells. In addition, as a measure of complement activation, we stain for deposition of C4d (M4D3; Connex) and C3b/C3bi (13-15; Connex). The presence of a local intraportal coagulant response is determined by staining with rabbit anti-fibrin(ogen) antibody (Dako Corp, Calif.), as well as rat anti-mouse CD-41 (MWReg30; BD Pharmingen) and CD62p (RB40.34, BD Pharmingen), which recognize platelet GPIIb/IIIa complex and P-selectin, respectively.

Isolation and characterization of lymphomyeloid cells from the mouse liver. The local hepatic inflammatory response is investigated after islet implantation by FACS analysis of lymphomyeloid cells isolated from the mouse liver. This analysis providesa quantitative assessment of the local cell response. A modified version of the method of Goossens et al. (131, 132) is used. Briefly, the liver is finely diced, ground through a coarse-mesh sieve and the resulting cell suspension passed through a 100-μm mesh sieve. The cells are pelleted at 400 xg for 10 min at 4° C. and resuspended to a volume of 30 mL in 3% fetal calf serum in a balanced saline solution and mixed with 17 mL of isotonic Percoll, giving a final concentration of 36% isotonic Percoll. This suspension is thoroughly mixed, and separation performed at 500 xg for 10 min at 4° C. The supernatant is removed and the pellet of lymphomyeloid cells resuspended in 5 mL of ammonium chloride. Approximately $10^5$ cells per sample are stained with unconjugated primary monoclonal antibody, resuspended in anti-immunoglobulin, and total cell numbers and distributions determined by FACS. Primary antibodies include anti CD3 (145-2C11; total T cells); anti CD8a (Ly 2; 53 6.7, cytotoxic T cells; BD Pharmingen); anti CD4 (GK1.5, helper T cells; BD Pharmingen); anti CD45R (RA3 6B2; total B cells); and MOMA-2 (total monocytes and macrophages).

PCR studies of IFN-gamma and IL-4 expression. The Th2 response is characteristic of evoked antibody responses to foreign antigens processed through the indirect antigen presentation pathway, while Th1 response is defined by cytolytic T cell-mediated rejection as a consequence of direct antigen presentation. In order to differentiate between these two potential pathways of islet destruction, mRNA from liver lymphomyeloid cells are recovered using the Quickprep Micro mRNA purification kit (Pharmacia) and real time quantitative RT-PCR performed with oligonucleotide primers corresponding to interferon-gamma (Th1 response) and IL-4 (Th2 response).

Film stability after implantation of coated islets is assessed by fluorescence imaging of specimens in which FITC-PLL has been incorporated into the barrier wall. Islet function is evaluated by monitoring random blood glucose levels with graft rejection defined as glucose>250 mg/dL for 2 consecutive days. Graft survival curves are calculated and compared by the log-rank test. The mean day to rejection is determined for barrier type. An indirect assessment of functional islet mass is determined by calculation of the glucose disposal rate (Kg) from an intraperitoneal glucose tolerance test (2 g/kg body weight) (133). In addition, liver sections are stained with an anti-insulin antibody (ICN Biomedicals) to assess insulin production in islet grafts.

RT-PCR studies can assess the production of additional cytokines (eg. TNF-a, IL-1b) within the liver that may contribute to islet destruction. Mouse models of diabetes and coagulation. The data generated in streptozotocin treated C57BL/6J mice are relevant to graft survival for primate studies, particularly with respect to early islet engraftment and the acute blood mediated inflammatory response. Significantly, the transplantation of B10.BR islets in streptozotocin treated C57BL/6J mice is a well-established model of allograft rejection (29). Moreover, the coagulation system in the C57BL/6J mouse closely resembles that of man (134). For example, a variety of knockouts of Protein C−/−, Factor V Leiden−/−, and disruption of TM cofactor function on a C57BL/6J background recapitulate the major hallmarks of hypercoaguable states observed in human disease. Likewise, $TF^{-/-}$, Factor $V^{-/-}$ Factor $X^{-/-}$, and Factor $II^{-/-}$ models demonstrate a propensity towards major bleeding with a high degree of embryonic lethality. The NOD mouse is an excellent model of juvenile onset diabetes and exhibits autoimmune rejection of islets not seen in streptozotocin induced models.

Heparin, TM and CD39. In recognition of the prothrombotic effects of intraportal islet infusion, most centers performing allogeneic islet transplantation currently use systemic heparin at the time of transplantation. Heparin is usually administered as a bolus dose of ~75 U/kg body weight, corresponding to ~5,000 U for a 70 kg person (~1 U/mL blood) (135). In a recent report, Korsgren and colleagues (135) observed that heparin prevented islet-induced coagulation in an ex vivo model, but at a four-fold higher concentration than that used clinically (4 U/mL blood). Furthermore, despite heparin administration at 4 U/mL blood, extensive platelet and fibrin formation, as well infiltration of CD11b+ cells continued to be observed on blood-exposed islets. Finally, even if one were to accept the risk of bleeding complications to be anticipated at a dosing level of 300 U heparin/kg, systemic heparin has a half-life of one hour and is therefore active for only a few hours. Thus, the potential therapeutic impact of intravenously administered heparin or, for that matter, activated Protein C (APC) is limited both by their systemic anticoagulant activity that increase the risk of bleeding complications and short half-life. By incorporating TM and heparin into a conformal islet coating, a rational strategy is established for locally generating an "actively" anticoagulant/anti-inflammatory barrier. It is noteworthy that heparin and APC demonstrate significant synergy in vivo due to three mechanisms that simultaneously decrease thrombin generation. First, heparin enhances antithrombin III-dependent inactivation of thrombin thereby limiting thrombin mediated Factor V activation; second, APC directly inactivates Factor Va; and third, heparin enhances by four-fold APC's ability to inactivate Factor V (52, 136). It also bears reemphasis that a variety of pro-inflammatory cytokines downregulate the expression of TM on endothelial cells with a concomitant decrease in APC production. Of particular relevance to intraportal islet transplantation, Kume (137), Terada (138), and Mochida (139, 140) have all observed that inflammatory stimuli decreases thrombomodulin expression in hepatic sinusoidal endothelial cells with fibrin deposition and microthrombus formation in vivo.

Any of three techniques can incorporate TM, heparin or CD39 into an LbL islet barrier. As outlined in FIG. 8, TM or heparin can be incorporated within a MM film, coupled directly to the surface via TM or heparin containing biotinylated vesicles to alginate-based polyelectrolyte multilayers and/or direct derivatization with both biotinylated heparin and PEG-TM conjugates. The multiple means for attaching molecules and biologics to the surface of LbL conformal barriers provides flexibility in the design of an anti-inflammatory/immunomodulatory islet barrier to maximize biocompatibility, stability and permeability properties.

The morphological, structural, and chemical properties of TM and/or heparin containing films are investigated in model LbL polymer films produced on silicon wafers using UV-vis and IR spectroscopy, as well as by HR-SEM. In addition, the surface concentration of TM can be quantified by radiochemical titration of $^{125}$I-TM. A TM surface density >500 fmol/cm$^2$ is required to achieve a maximum rate of protein C activation that is otherwise substrate limited (i.e. independent of TM surface concentration and solely dependant upon plasma protein C concentration). Barrier catalytic activity is defined, as detailed elsewhere (91), by measuring $K_m$ and $k_{cat}$ for conversion of protein C to activated protein C. In parallel investigations, LbL films are incubated directly with biotin-heparin conjugates and the surface concentration of heparin determined either by radiochemical titration of $^3$H-labeled heparin (American Radiolabeled Chemicals, St. Louis Mo.) or by hexosamine analysis using p-dimethylaminobenzaldehyde (141, 142). The rate of thrombin inactivation by antithrombin III is defined as a function of surface heparin concentration using the chromogenic substrate S-2238 (Chromogenix, Italy), as described elsewhere (91). This gives a heparin surface concentration above which the rate of thrombin inactivation is solely dependent on plasma ATIII concentration. Following optimization of model planar film studies, conditions to attain targeted heparin and/or TM surface concentrations are determined for both barrier-coated islets and empty microcapsules. Other investigators have determined that human TM can efficiently activate murine protein C (143-146). However, these in vitro studies are performed using human plasma proteins for both cost effectiveness and for in vitro investigations with human whole blood, outlined below.

The ability of barrier associated TM and/or heparin to limit blood mediated coagulant and non-immune inflammatory responses is initially assessed in vitro. Specifically, we use minimally altered whole blood in which contact activation (i.e. factor XIIa) is suppressed by addition of corn trypsin inhibitor (CTI; Hematologic Technologies, VT). This model, initially described by Mann and colleagues (147, 148), facilitates short-term (<60 min) investigations of coagulation related processes under in vitro conditions that closely approximate the clotting of native blood in vivo. The significance of this approach is that it allows examination of initial blood-islet interactions under allogeneic (human islets+ABO compatible human blood) or xenogeneic (porcine islets+human blood) conditions to obtain data relevant to both barrier design and optimization, as well as to correlative animal studies. In addition, a foundation will be established for potential future primate or clinical investigations. Human islets are obtained from donor preparations of good quality, but of insufficient islet volume for clinical transplantation. Porcine islets are obtained through the Emory University JDRF Core Islet Facility.

In both allogeneic and xenogeneic systems, whole blood interactions are characterized using both encapsulated (bearing heparin alone vs. TM alone vs. heparin+TM) and unencapsulated islets, as well as empty capsules. In addition, responses to non-TM, non-heparin containing capsules are characterized as additional controls. Briefly, approximately 800 islets are washed twice in RPMI 1640, three times with PBS, resuspended in 50 μL RPMI 1640, and placed in polystyrene tubes incubated on a rocker at 37° C. Non-anticoagulated human blood is collected from normal donors with no history of either blood disorders, tobacco, aspirin or drug use and rapidly distributed to a series of polystyrene test tubes (1 mL/tube) containing CTI (100 mg/mL) and islets. All subjects are tested for glucose, fibrinogen, prothrombin time, activated partial thromboplastin time, and a hemogram obtained to ensure that all values fall within normal range. A tube without islets is added as a control to determine the quality of the phlebotomy and the extent of contact pathway inhibition by CTI. Blood samples are collected at 0, 1, 5, 10, 15 and 30 minutes and quenched with a mixture of coagulation inhibitors, 50 mM EDTA with 20 mM benzamidine-HCl in HBS, pH 7.4. The following assays are performed: (a) Thrombin formation is determined by measuring prothrombin fragments 1 and 2, thrombin-antithrombin III complex formation, and fibrinopeptide A (FPA) levels. In the presence of TM containing barriers, activated protein C levels are measured in order to provide correlative data to the observed response. (b) Activation of platelets is assessed from the change in platelet count (Coulter differential analyzer; Beckman Coulter) and by plasma levels of the releasable platelet α-granule protein, β-thromboglobulin. (c) Leukocyte activation is evaluated by measuring change in leukocyte count (monocyte and neutrophils) and myeloperoxidase (MPO) release. (d) Complement activation is defined by assays for C3a and sC5b-9. Commercial ELISA kits are available for all of these assays.

Islets are also collected at these time points, embedded in freezing medium, serially sectioned (5 μm), and stained to examine both islet morphology and surface deposition of fibrin, complement, platelets, and leukocytes. The following anti-human primary antibodies are used: mouse anti-fibrin (Immunotech); antibodies against complement components, C4d (M4D3; Connex) and C3b/C3bi (13-15; Connex); mouse anti-human CD-41a (DD4.1; R&D Systems) and CD62p, which recognize platelet GPIIb/IIIa complex and P-selectin, respectively; and anti-CD11b (clone 2LPM 19c, DAKO), which is expressed on leukocytes.

The capacity to inhibit acute blood mediated inflammatory responses in vivo is evaluated using barriers that contain either (a) TM alone; (b) heparin alone; or (c) both TM and heparin, all at surface concentrations that maximize APC production and/or thrombin inactivation. Following the protocol described above, approximately 250 empty capsules are injected into the portal circulation of C57BL/6J mice and in vivo plasma markers, which are typically elevated upon activation of platelets and coagulation enzymes, are monitored over a 48-hour period. Thrombin formation is determined by measuring levels of thrombin-antithrombin III complexes and consumption of fibrinogen and its cleavage by thrombin is assessed by measurements of plasma clottable fibrinogen and fibrinopeptide A (FPA) levels. Activation of platelets is assessed from the change in platelet count and by plasma levels of β-thromboglobulin. Likewise, the local hepatic inflammatory response is investigated by light microscopy and immunohistochemistry 1, 3, 7, 14, and 28 days after infusion of empty capsules. The following are used as primary antibodies: anti-myeloperoxidase, as a marker for neutrophil infiltration and MOMA-2 (Research Diagnostics), as a marker of mouse monocyte and macrophage infiltration. In addition, the presence of a local intraportal coagulant response is determined by staining with rabbit anti-fibrin (ogen) antibody (Dako Corp), as well as rat anti-mouse CD41 (MWReg30; BD Pharmingen) and CD62p (RB40.34, BD Pharmingen), which recognize platelet GPIIb/IIIa complex and P-selectin, respectively.

Biostability of empty TM/heparin containing capsules is characterized after portal vein infusion by light and fluorescence microscopy 2, 4, and 8 weeks after implantation. Fluorescence imaging is performed on selected specimens in which, FITC-PLL has been incorporated into the barrier wall. The persistence of barrier associated TM and heparin is assessed using anti-TM (21-5D2; American Diagnostica) and anti-heparin (MAB2040; Chemicon) antibodies.

Species specificity of TM. Human TM is commercially available and is the most appropriate form of TM for the studies of human blood-islet interactions, outlined herein. Moreover, results with human TM establish a useful foundation for future primate investigations. Of note, we and other investigators have determined that human TM can efficiently activate mouse protein C. Indeed, soluble human thrombomodulin has been used to activate protein C in a variety mouse models of thrombosis and inflammatory injury (143-146). Duration of in vivo TM activity. Studies have demonstrated that TM remains active for a minimum of 2 to 3 months when incubated in plasma at 37° C. Immunogenicity of human TM and CD39 in C57BL/6J mice. In general terms, the immunogenicity of a given protein can be difficult to predict and is dependant upon the route of administration, duration and schedule of dosing, the cumulative dosage of the protein, as well as peptide structure. Antibody responses will not limit the proposed studies. Mice receive only a single administration of human TM and/or CD39 bound to the barrier film surface. Serum antibody levels to human TM and CD39 can be measured. Briefly, recipient mice are tail bled 15, 30 and 45 days after transplantation and the serum (1:10 dilution) incubated with TM or CD39 derivatized polystyrene microbeads (Polysciences) at room temperature for 30 min. Beads are washed and incubated with anti-mouse IgG FITC-conjugated antibody (1:100 dilution) for 30 min at room temperature. Beads incubated with the secondary antibody only are used to determine background fluorescence. The TM-specific antibody (21-5D2; American Diagnostica) and CD39 specific antibody (BU61; AnCell Co., Bayport, Minn.) are used as positive controls and normal mouse serum, as a negative control. The beads are washed and fixed in 1% paraformaldehyde and flow cytometry performed to assess mean channel fluoresence of each individual serum sample. If an antibody response to human TM or CD39 is detected, mouse TM and CD39 can be expressed from their available cDNA clones (TM clone MGC:29138, CD39 MGC:18369, Life Technologies/Invitrogen).

Whether a conformal polymer coating, which contains TM and/or heparin, enhances portal islet engraftment is assessed by measuring the fraction of streptozotocin treated C57BL/6J mice that become euglycemic as a function of islet number, as detailed hereinabove. Both B10.BR mouse islets and porcine islets are used. A beneficial effect is defined by observing an increase in the fraction of animals that achieve euglycemia as a function of time. Rates of engraftment are correlated with plasma markers of platelet activation and thrombin generation, as previously described. Time to graft rejection is determined and the portal inflammatory response analyzed at 1, 3, 7, and 28 days and at monthly intervals thereafter. As outlined above, immunohistochemical staining of islet-grafted liver tissue provides the primary assessment of the local coagulant and inflammatory/immune responses. FACS and RT-PCR (for IFN-gamma and IL-4) of lymphomyeloid cells from the mouse liver are performed selectively to quantitate, respectively, cell type, as well as Th1 vs Th2 response. Islet function is assessed by monitoring blood glucose levels, IP glucose tolerance tests, and immunohistochemical staining of intraportal islets for insulin. In select experiments, film integrity is defined by doping barriers with FITC-PLL. In addition, the persistence of barrier associated TM and/or heparin is evaluated by immunohistochemical staining with anti-TM and anti-heparin monoclonal antibodies.

Local release of ATP and ADP from activated endothelium and platelets strongly promote proinflammatory and prothrombotic events (61, 62, 149). By reducing local concentrations of ATP and ADP, CD39 represents a physiologically important antithrombotic/anti-inflammatory regulatory mechanism (66, 67). Moreover, by rapidly metabolizing extracellular ATP and ADP, locally generated AMP can lead to a major increase in adenosine. By activating A2A receptors, adenosine inhibits platelet aggregation, as well as histamine and cytokine release from mast cells and macrophages, and the expression of adhesion molecules, such as P-selectin and ICAM-1 on endothelium (62, 150). Furthermore, activation of A2A receptors on human monocytes inhibits secretion of IL-1 2, a proinflammatory cytokine and a major inducer of Th1 responses (151, 152). Finally, it bears emphasis that expression of CD39 on endothelial cells is rapidly decreased by reperfusion injury, oxidant stress, or cytokine-mediated activation responses, all of which occur at the time of portal islet infusion (65). Thus, the incorporation of CD39 into a conformal islet barrier provides a useful strategy either alone or in concert with TM and/or heparin to limit proinflammatory and procoagulant events, which contribute to acute islet non-function and late islet destruction. The concentration of surface-bound CD39 is correlated to inhibition of acute blood mediated inflammatory response initiated on infusion of intraportal islets. This correlation establishes a foundation for determining the effectiveness of CD39 either alone or in combination with surface bound TM and/or heparin in enhancing islet engraftment and long-term islet survival.

Barriers that limit local purinergic receptor activation can enhance portal engraftment of islets and long-term islet survival in both allogeneic and xenogeneic transplant models. CD39 bearing films are produced (in an analogous manner to TM and/or heparin bearing films) and enzymatic activity characterized. The capacity of these films to limit acute blood mediated inflammatory responses is determined in vivo both in the context of empty capsules and as conformal islet barriers. Finally, the impact of this strategy on allo- and xenogeneic islet engraftment and long-term survival is defined.

CD39 containing films are initially produced on silicon wafers and surface properties characterized using UV-vis and IR spectroscopy, as well as by HR-SEM. As outlined previously, CD39 is incorporated either in the context of a planar membrane-mimetic film or as surface bound vesicles (FIG. 8). The surface concentration of CD39 containing films is defined by radiochemical titration of $^{125}$I-labeled protein. The rate of ATP and ADP dephosphorylation is defined as a function of CD39 surface concentration in order to define the mass transfer limited regime in which the rate of dephosphorylation is maximum and independent of surface ATPase or ADPase activity. Following optimization of model film studies, the ability to attain targeted CD39 surface concentrations is determined on both barrier-coated islets and empty microcapsules.

The ability of barrier associated CD39 to limit blood-mediated coagulant and non-immune inflammatory responses is initially assessed in vitro. As described above, experiments use minimally altered whole blood in which contact activation is suppressed by addition of corn trypsin inhibitor (147, 148). We examine blood-islet interactions under allogeneic (human islets+ABO compatible human blood) or xenogeneic (porcine islets+human blood) conditions. In both systems, whole blood interactions are characterized using both encapsulated and unencapsulated islets, as well as empty capsules. Briefly, approximately 800 islets are washed twice in RPMI 1640, three times in PBS, resuspended in 50 μL RPMI 1640 and placed in polystyrene tubes incubated on a rocker at 37° C. Non-anticoagulated blood is collected from normal donors and rapidly distributed to a series of test tubes (1 mL/tube) containing CTI (100 mg/mL) and islets. A tube without islets is added as a control to determine the quality of the phlebotomy and the extent of contact pathway inhibition by CTI. Blood samples are collected at 0, 1, 5, 10, 15 and 30 minutes and quenched with a mixture of coagulation inhibitors, 50 mM EDTA with 20 mM benzamidine-HCl in HBS, pH 7.4. The following assays are performed: (a) Thrombin formation is determined by measuring prothrombin fragments 1 and 2, thrombin-antithrombin III complex formation, and fibrinopeptide A (FPA) levels. (b) Activation of platelets is assessed from the change in platelet count and by plasma levels of β-thromboglobulin. (c) Leukocyte activation is evaluated by measuring change in leukocyte count (monocyte and neutrophil) and myeloperoxidase (MPO) release. (d) Complement activation is defined by assays for C3a and sC5b-9. Commercial ELISA kits are available for all of these assays.

Islets are also collected at these time points, embedded in freezing medium, serially sectioned, and stained to examine both islet morphology and surface deposition of fibrin, complement, platelets, and leukocytes. The following anti-human primary antibodies are used: mouse anti-human fibrin (Immunotech); antibodies against complement components, C4d (M4D3; Connex) and C3b/C3bi (13-15; Connex); mouse anti-human CD41a (DD4.1; R&D Systems) and CD62p, which recognize platelet GPIIb/IIIa complex and P-selectin, respectively; and anti-CD11b (clone 2LPM 19c, DAKO), which is expressed on leukocytes.

The capacity to inhibit acute blood mediated inflammatory responses is evaluated using films that contain CD39 at optimized surface concentration. In a manner analogous to that described for TM and heparin bearing barriers, approximately 250 empty capsules are injected into the portal circulation of C57BL/6J mice and in vivo plasma markers, which are elevated upon activation of platelets and coagulation enzymes, are monitored over a 48-hour period. As outlined previously, thrombin formation is determined by measuring levels of thrombin-antithrombin III complexes and consumption of fibrinogen and its cleavage by thrombin is assessed by measurements of fibrinogen and fibrinopeptide A. Activation of platelets is assessed from the change in platelet count and by levels of β-thromboglobulin. The local hepatic inflammatory response is investigated by light microscopy and immunohistochemistry 1, 3, 7, 14, and 28 days after infusion of empty capsules. The following are used as primary antibodies: anti-myeloperoxidase, as a marker for neutrophil infiltration and MOMA-2, as a marker of mouse monocyte and macrophage infiltration. In addition, the presence of a local intraportal coagulant response is determined by staining with rabbit anti-fibrin(ogen) antibody (Dako Corp), as well as rat anti-mouse CD-41 (MWReg30; BD Pharmingen) and CD62p (RB40.34, BD Pharmingen), which recognize platelet GPIIb/IIIa complex and P-selectin, respectively.

Biostability of empty CD39 containing capsules is characterized after portal vein infusion by light and fluorescence microscopy 2, 4, and 8 weeks after implantation. Fluorescence imaging is performed on selected specimens in which, FITC-PLL has been incorporated into the barrier wall. In addition, the persistence of barrier associated CD39 is assessed by staining with an anti-CD39 MAb (BU61; AnCell Co., Bayport, Minn.).

To assess whether a conformal polymer coating containing CD39 enhances portal islet engraftment, the fraction of streptozotocin treated C57BL/6J mice that become euglycemic is defined as a function of islet number. Both B10.BR mouse islets and porcine islets are used. A beneficial effect is defined by observing an increase in the fraction of animals that achieve euglycemia as a function of time. Rates of engraftment are correlated with plasma markers of platelet activation and thrombin generation. Time to graft rejection is determined and the portal inflammatory response analyzed at 1, 3, 7, and 28 days and at monthly intervals thereafter. As outlined above, immunohistochemical staining of islet-grafted liver tissue provides an assessment of the local coagulant and inflammatory/immune responses. FACS and RT-PCR (for IFN-gamma and IL-4) of lymphomyeloid cells from the mouse liver are performed selectively to quantitate, respectively, cell type, as well as Th1 vs Th2 response. Islet graft function is evaluated by serial blood glucose measurements, IP glucose tolerance testing, and immunohistochemical staining of grafts for insulin production.

Blockade of both thrombin- and purinergic-dependent proinflammatory and prothrombotic pathways maximizes portal engraftment of islets and long-term islet survival. In order to assess whether a coating, which blocks both thrombin- and purinergic-dependant proinflammatory and prothrombotic pathways enhances islet engraftment and limits subsequent immune rejection, islets are coated with a barrier containing optimized surface concentrations of TM, heparin, and CD39. Blood-islet interactions in vitro under allogeneic (human islets+ABO compatible human blood) or xenogeneic (porcine islets+human blood) conditions are examined. A minimally altered whole blood model is used, and both blood and islets serially analyzed, as detailed above. The fraction of streptozotocin treated C57BL/6J mice that become euglycemic is defined as a function of islet number, as detailed above. Both B10.BR mouse islets and porcine islets are used. A beneficial effect is defined by observing an increase in the fraction of animals that achieve euglycemia as a function of time. Rates of engraftment are correlated with plasma markers of platelet activation and thrombin generation. Time to graft rejection is determined and the portal inflammatory response analyzed, as outlined above, by immunohistochemistry, FACS, and RT-PCR of islet-grafted liver tissue. In select experiments, film integrity, as well as the persistence of surface bound TM, CD39, and heparin are evaluated, as previously described. Finally, islet graft function is evaluated by serial blood glucose measurements, IP glucose tolerance testing, and immunohistochemical staining of grafts for insulin production. LbL conformal coating (with or without TM, CD39 and/or heparin) can be used in combination with current immunosuppression and tolerance inducing strategies, as known in the art, for islet transplantation.

Construction of Pegylated Multilayer Architectures via (Strept)avidin/Biotin Interactions. Layer-by-layer (LbL) self-assembly provides a versatile approach for the formation of multifunctional thin films with well-defined nanoscale architectural features (Decher, Science 277 (1997) 1232). For example, core-shell structures have been produced by a template LbL assembly of a polymeric multilayer onto a central sacrificial core. Subsequent removal of the core yields hollow capsules (Donath et al., Angew. Chem. Int. Ed. 37 (1998) 2202); Dai et al., Chem. Eur. J. 8 (2002) 4751; Langmuir 18 (2002) 9533; Chem. Int. Ed. 41 (2002) 4019)). Indeed, core-shell architectures are of increasing interest in areas of cell encapsulation, controlled drug delivery, and bioimaging (Keller et al., J. Am. Chem. Soc. 117 (1995) 12879; Chen et al., J. Am. Ceram. Soc. 81 (1998) 140; Dokoutchaev et al., Chem. Mater. 11 (1999) 2389). Moreover, free-standing hollow capsules may be useful as protective containers or as confined reaction vessels (Nature 369 (1994) 298; Adv. Mater. 13 (2001) 1339; Langmuir 18 (2002)4553; J. Phys. Chem. 106 (2002) 11501).

To date, electrostatic attraction between anionic and cationic polyelectrolytes has been used as the principle driving force for LbL assembly of multilayered polymer films. Hence, limitations are often encountered in the fabrication of thin films composed of nonionic polymers or polyelectrolytes of identical charge. To overcome these problems, (strep)avidin/biotin binding interactions have been recently applied in the construction of layer-by-layer thin films (Anal. Chem. 67 (1995) 770; Langmuir 15 (1999) 221). Of note, each avidin molecule contains four biotin binding sites characterized by an exceedingly high binding affinity (log >>15) (Anal. Biochem. 171 (1988) 1; Biochemistry 28 (1989) 8214; Langmuir 8 (1992) 1413; Science 262 (1993) 1706). These four binding sites are located in pairs on either side of the protein molecule. Thus, upon binding to a biotinylated surface via both binding sites on one face of the protein, the binding sites on the opposite face are accessible to other biotinylated molecules (Scheme 1). In this manner, the potential exists to generate a variety of unique multilayer assemblies for use in molecular diagnostics, drug or cell encapsulation, as well as biofunctional coatings to improve the performance of implanted medical devices [Anal. Biochem. 171 (1988) 1; J. Am. Chem. Soc. 120 (1998) 1665). In this example, we investigate (strept)avidin/biotin interactions as a driving force for LbL fabrication of films on planar substrates, as shells on colloidal particles, and as free-standing hollow capsules.

Poly(L-lysine) (PLL, mol wt ~15-30 kDa), alginate (Alg), avidin, and streptavidin, avidin labeled with FITC (AF) and streptavidin labeled with FITC (SAF), and biotin-amidocaproate N-hydroxysuccinimide ester were all purchased from Sigma. The $\alpha$-biotin-$\omega$-N-hydroxysuccinimidyl ester of poly(ethylene glycol)-carbonate (biotin-PEG-$CO_2$-NHS, mol wt ~3.4 kDa) was obtained from Shearwater Polymers, Inc., Huntsville, Ala. Melamine formaldehyde (MF, 4.34 µm) particles were purchased from Microparticles, GmbH, Germany. An electrostatic bead generator (Pronova Biomedical, Inc.) set at 4.7 kV was used for the fabrication of alginate microbeads (d~300 µm). The alginate solution (2.0% w/v, pH 7.4) was extruded at a flow rate of 0.2 mL/min through a flat end needle with an internal diameter of 0.10 mm into a 1.1% w/v $CaCl_2$ solution.

Synthesis of biotin-derivatized poly(L-lysine)-g-poly(ethylene glycol)(PPB). The synthesis was performed as detailed elsewhere (Chem. Biol. 5 (1998) 177). Poly-L-lysine hydrobromide (PLL-HBr, 100 mg) was dissolved in 2.5 mL of 50 mM sodium tetraborate buffer (pH 8.5). The resulting solution was filtered through a 0.22 mm Durapore membrane (sterile Millex GV, Sigma-Aldrich). The stoichiometric amount of Biotin-PEG-$CO_2$-NHS was then slowly added to the solution while it was vigorously stirred. After 6 more hours of vigorous stirring at room temperature, the solution was transferred to a dialysis tube (Spectr/Por dialysis tubing, MWCO of 15 kDa). Dialysis was carried out for 24 h in 2 L of 10 mM phosphate-buffered saline (PBS, pH 7.4), followed by 24 additional hours of dialysis in 2 L of deionized water. A small fraction of PLL-g-PEG copolymers with high molecular weight PLL backbones that was poorly soluble in water was removed using a 5 mm syringe filter. The product was then freeze-dried for 48 h.

The $^1$H NMR chemical shifts (in $D_2O$) were assigned based on comparison with spectra of the individual reagents as follows: 1.2-1.3 and 1.3-1.6 ppm (m, —$CH_2$—, carbons of the lysine side chains and —$CH_2CH_2CH_2$— in biotin that are nearest to the thiophene ring), 2.09 ppm (t, —$CH_2CH_2CH_2C(O)NH$—, biotin), 2.60 ppm (incompletely resolved q, —$CH_aH_bS$—, biotin), 2.79 ppm (m, —$CH_aH_bS$— in biotin and —$CH_2NH_3^+$ in ungrafted lysine chains), 2.99 and 3.13 ppm (incompletely resolved multiplets, $CH_2NHC(O)OCH_2$— from biotinylated PEG linked to lysine and —$CH_2NHC(O)CH_2$— from biotinylated PEG itself), 3.21 ppm (m, —CHS—, biotin), 3.50 ppm (m, —$CH_2CH_2O$—, ethylene glycol), 4.10 ppm (m, —NHC(O)CH—, lysine backbone), 4.25 and 4.42 ppm (m, 13 CHNHC(O)—, biotin).

To estimate the percentage of available lysine residues that have reacted with biotin-PEG-$CO_2$—NHS, it was necessary to use the integrated intensities of peaks, which could be both unambiguously assigned and have little or no overlap with neighboring peaks. The optimal peaks for these were at 2.09 ppm (t, —$CH_2CH_2CH_2C(O)NH$—, biotin) and at 4.10 ppm (m, —NHC(O)CH—, lysine backbone). The percentage is given by the intensity of the peak at 4.10 ppm (0.88) divided by half the intensity of the peak at 2.09 ppm (0.5) (28%).

Figure 16B:
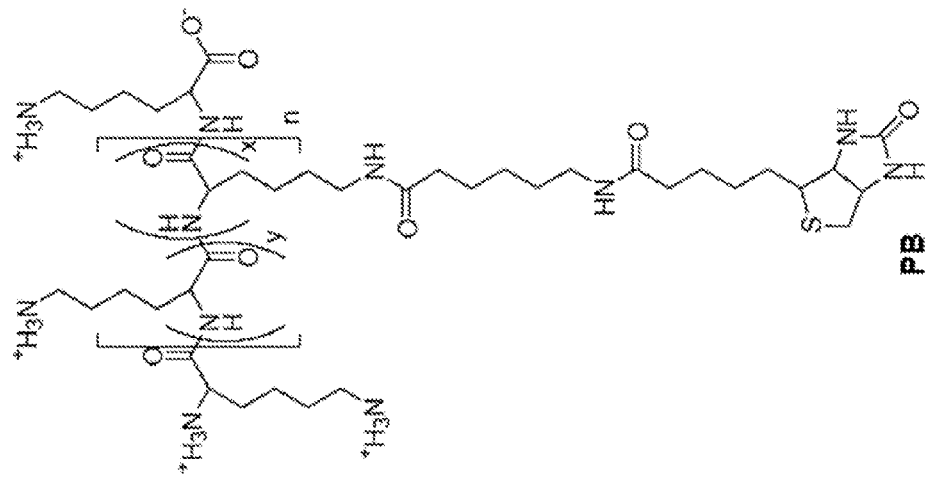
FIGS. 16A-B: Chemical structure of (A) biotin-derivitized poly(L-lysine)-g-poly(ethylene glycol) (PPB) and (B) biotinylated poly-L-lysine (PB).
Figure 16A:
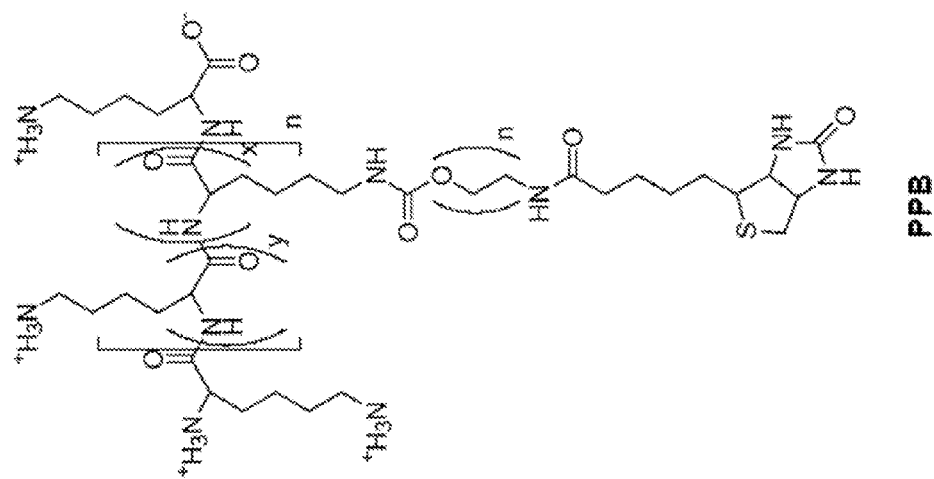

Biotinylated poly-L-lysine (PB) was synthesized from poly-L-lysine hydrobromide (PLL-HBr, 100mg) and biotin-amidocaproate N-hydroxysuccinimide ester (54.5 mg) in a manner analogous to PPB. The percentage of lysine residues reacted with NHS-biotin was estimated to be 23%. The chemical structures of PPB and PB are shown in FIG. 16.

Preparation of multilayers on planar substrates. The surface of a quartz slide (0.5×1 inch) was first cleaned and made hydrophilic by immersion in a $H_2SO_4/H_2O_2$ (7:3) bath for 1 h and then in a $H_2O/H_2O_2/NH_3$ (5:1:1) bath at 60° C. for 30 min. The surface was then carefully rinsed in distilled water. This cleaned quartz slide was immersed in a PB solution (1 mg/mL in phosphate-buffered saline (PBS), pH 7.4) for 30 min to deposit the first layer of PB. After being rinsed with PBS for a few minutes, the quartz slide was immersed in an avidin-FITC (AF) solution (0.1 mg/mL in PBS) for 30 min and rinsed with PBS. This process provides both sides of the quartz slide with a PB/AF bilayer. In order to deposit the second bilayer of PB/AF, the coated quartz slide was treated similarly with the PB and AF solutions. The same procedure was repeated until the desired number of layers was obtained. The absorption spectra were recorded after every deposition. All of the experiments were carried out at room temperature.

Engineering multilayer shells on alginate beads. At room temperature, alginate beads were incubated with 1 mg/ml PLL solution in PBS for 1 min and then rinsed twice with PBS. Beads were then incubated in dilute 2 mg/mL ALG solution in PBS for 3 min followed by two brief saline rinses. This process completed a cycle of forming a single PLL/Alg bilayer and was repeated three times followed by 3 min incubation in PPB. The beads were then incubated in a solution containing streptavidin labeled with FITC (SAF) for 30 min and subsequently rinsed three times with PBS.

Layer-by-layer assembly of hollow capsules. The first two layers of Alg and PPB were consecutively deposited onto positively charged MF colloidal particles from 2 mg/mL Alg solution in PBS and 1 mg/mL PPB solution in PBS with an adsorption time of 15 min (Chem. Int. Ed. 37 (1998) 2202), providing biotin sites on the MF particle surface for streptavidin binding. Thereafter, 1.5 mL of SAF solution (0.1 mg/mL) in phosphate-buffered saline was added to a 0.1 mL suspension of alginate/PPB coated MF colloid particles and incubated for 30 min at room temperature on a mechanical rocker. The particles coated with SAF were separated from unreacted SAF by three repeated centrifugation (2000 g, 2 min)/washing/redispersion cycles. The PPB solution was then added to the suspension of the alginate/PPB/SAF coated particles and the sample was incubated for 30 min. All unattached PPB was removed in the same manner. Subsequently, alternating SAF and PPB layers were deposited in identical fashion until the desired number of layers was obtained. Hollow capsules were prepared by dissolving the MF core with 0.1 M HCl. The resulting hollow polymer capsules were then centrifuged at 1000 g for 5 min, washed with 0.1 N HCl twice, then washed in water three times. Hollow capsules were also prepared from multilayers of PPB/AF, PB/SAF and PB/AF in the same manner.

Characterization methods. Lyophilized polymers were dissolved in $D_2O$ and $^1$H NMR spectra were recorded on a 300 MHz spectrometer (Varian, Palo Alto, Calif.). Absorption spectra were measured using a Varian Cary 4E UV-visible spectrophotometer. Confocal micrographs were taken with a confocal laser scanning microscope (Zeiss LSM 510) equipped with a 40× oil immersion objective. The morphology of the capsule wall was investigated by transmission electron microscopy (TEM) of ultrathin sections. Hollow capsules were fixed with 2.5% glutaraldehyde in 0.1 M cacodylate buffer, pH 7.2, overnight at 4° C., followed by three washes with the same buffer. Samples were then treated with 1% osmium tetroxide in 0.1M cacodylate buffer for 1 hour at room temperature. After fixation with osmium, samples were dehydrated through an ascending ethanol series and embedded in Eponate 12 resin (Ted Pella Inc) and polymerized in an oven for two days by heating at 60° C. Samples were cut in 70 nm thick sections on an ultramicrotome "Ultracut E", and stained with uranyl acetate and lead citrate. The sections were examined with a Hitachi H-7500 transmission electron microscope.

Figure 17A:
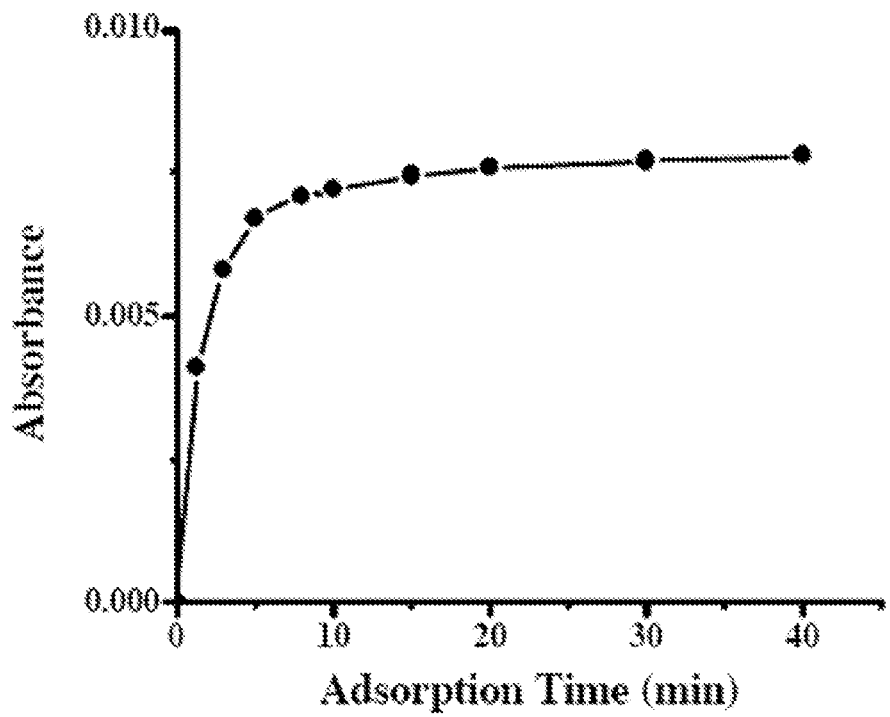
FIGS. 17A-B: (A) Time course of the adsorption of AF on the surface of a PB-coated quartz slide. (B) Absorption spectra of multilayer films of $(PB/AF)_n$ (n=1, 2, 3, 4, 5, 6, 7, 8, 9) formed on quartz slide as a function of the number of depositions. The multilayer films are deposited on both surfaces of the slide. Concentrations of PB and AF in the bathing solutions are 1 mg/mL and 100 mg/mL in PBS, respectively.
Figure 17B:
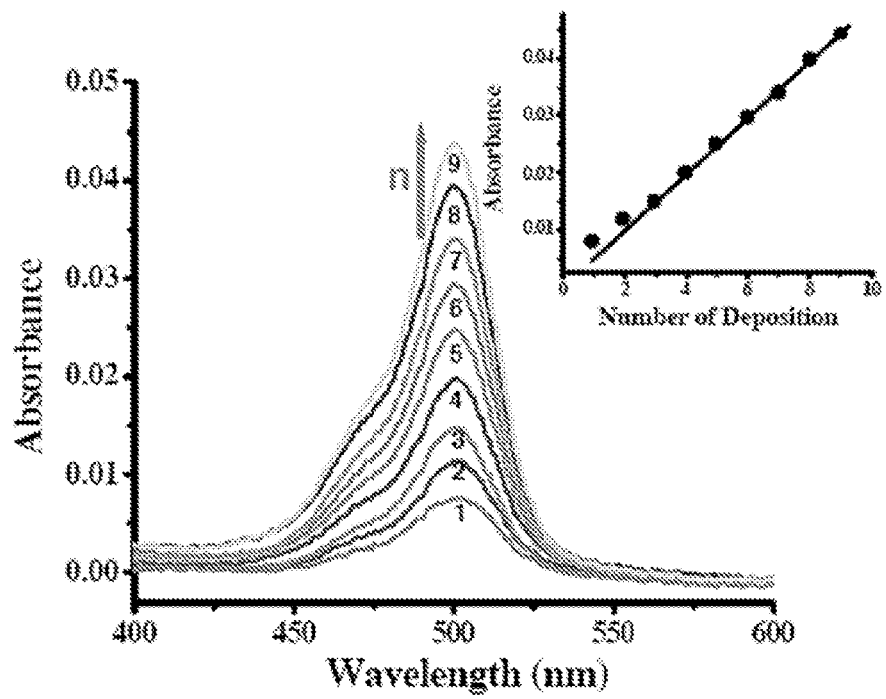

Anzai and colleagues have recently documented that multilayer films can be produced on quartz slides by sequential deposition of avidin and biotinylated polymers, including poly(ethylene imine), poly(allylamine), or poly(amidoamine) dendrimers (Anal. Chem. 67 (1995) 77013; Langmuir 15 (1999) 221). Similarly, we confirmed using UV/vis spectroscopy that FITC labeled avidin rapidly and irreversibly binds to biotinylated poly-L-lysine-coated quartz slides with sequential immersion in solutions of PB and avidin yielding multilayer architectures (FIG. 17). The loading of FITC-avidin was estimated from the absorbance data, using a molar extinction coefficient of 176,000 $M^{-1}cm^{-1}$ at ca. 500 nm. Id. The absorbance of PB/AF multilayer films as a function of deposition number yielded a linear plot with a slope of 0.0044±0.0006/deposition (FIG. 17B). Assuming that AF forms a closely packed monomolecular layer, the surface density of AF is $(6.3±1.3)×10^{-2}$ mol $cm^{-2}$. Since the absorbance of the monomolecular layer of AF at 500 nm is 0.0022±0.0004, depending on the orientation of the AF molecule (Id.), these data suggest that approximately 2 monolayers of FITC-avidin were adsorbed with each deposition.

Confocal fluorescence images provide further evidence of AF adsorption onto thin films containing an outer PB coating. As expected, the biotinylated surface exhibits strong fluorescence after incubation with AF solution (data not shown). In contrast, significant adsorption of avidin was not observed to PLL in the absence of biotin since avidin and PLL are both positively charged, repelling each other electrostatically, and thereby limit nonspecific adsorption.

Figure 18A:
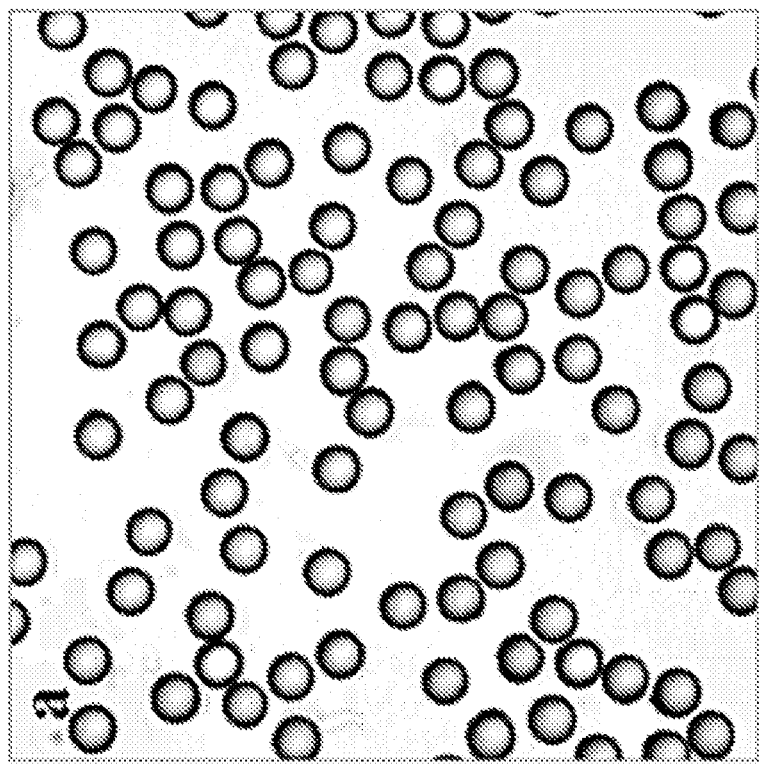
FIGS. 18A-B: Confocal transmission images of (A) MF particles coated with an Alg(PB/AF)$_4$ multilayer and of (B) hollow capsules of Alg(PB/AF)$_4$ obtained by removal of the templated MF cores (4.34 micron diameter) with 0.1 N HCl acid.
Figure 18B:
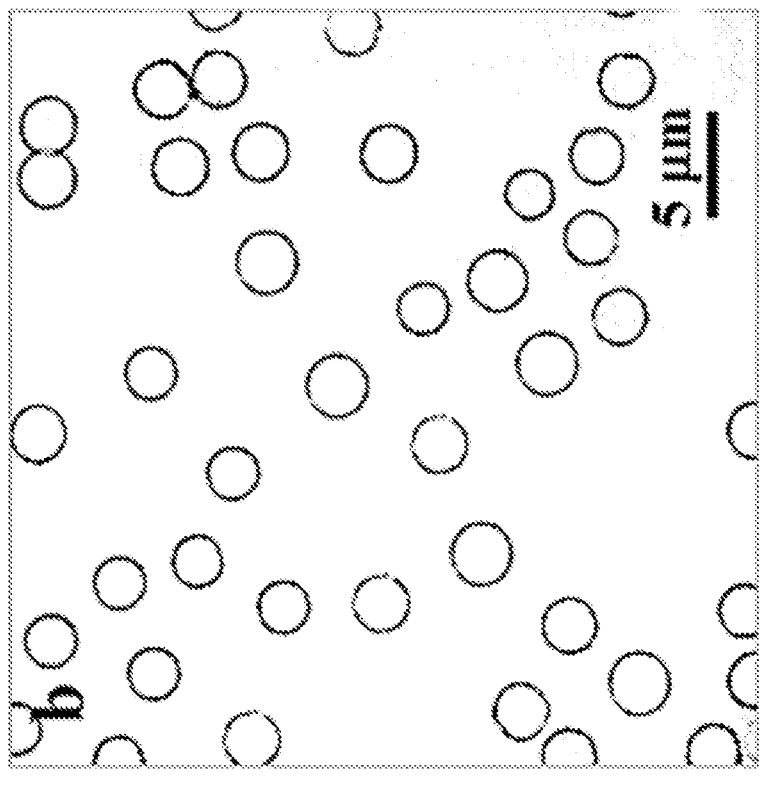

Evidence for the formation of the PB/AF multilayers on colloid particles was obtained by employing decomposable MF colloid templates as supports for multilayer assembly. Time-of-flight mass spectrometry experiments has revealed that the MF particles readily decompose into their constituent oligomers consisting mostly of 5-10 monomers of tetramethylolmelamine upon exposure to acidic solutions of pH<1.6 (Angew. Chem. Int. Ed. 37 (1998) 2202). The pores in the shell comprised of the PB/AF layers are large enough to allow solubilized MF oligomers to diffuse through the capsule wall. Direct visualization of hollow capsules was provided by confocal laser scanning microscopy (CLSM) measurements (FIGS. 18A-B). The structures seen in the transmission image (FIG. 18B) are due to the contrast of the remaining PB/AF complex layers from the original coating of particles, thus confirming the LbL assembly of the polymer and biomaterials on the particles. Obviously, the resulting hollow capsules preserve their integrity and the spherical shapes of the original colloidal particles. This suggests that during core removal only a small osmotic pressure is transiently established and polymer shells can resist this pressure. This result is also consistent with the visual observation that the polymer-coated MF microparticle suspensions lost their turbidity upon addition of 0.1 N HCl.

Overlapped confocal transmission and fluorescence images after incubation with SAF shows no fluorescence of the (PLL/Alg)$_3$PLL coated alginate beads. In contrast, a fluorescent ring is observed surrounding the (PPB/Alg)$_3$PPB coated beads (data not shown). Thus, SAF is adsorbed onto bead surfaces via the strong interaction between streptavidin and biotin conjugated to PLL.

Without wishing to be constrained to any particular theory, we believe that PEO structured multilayer assemblies offers improved in vivo biocompatibility, reduced non-specific protein adsorption, and an additional mechanism to control thin film physiochemical properties, including film permeability, as well as the capacity of a film to host guest compounds (J. Biomater. Sci. Polym. Ed. 9 (1998) 163; Artif. Organs 22 (1998) 821). As such, PEG was incorporated into these multilayer assemblies by chemical conjugation of PEG to PLL.

Figure 19B:
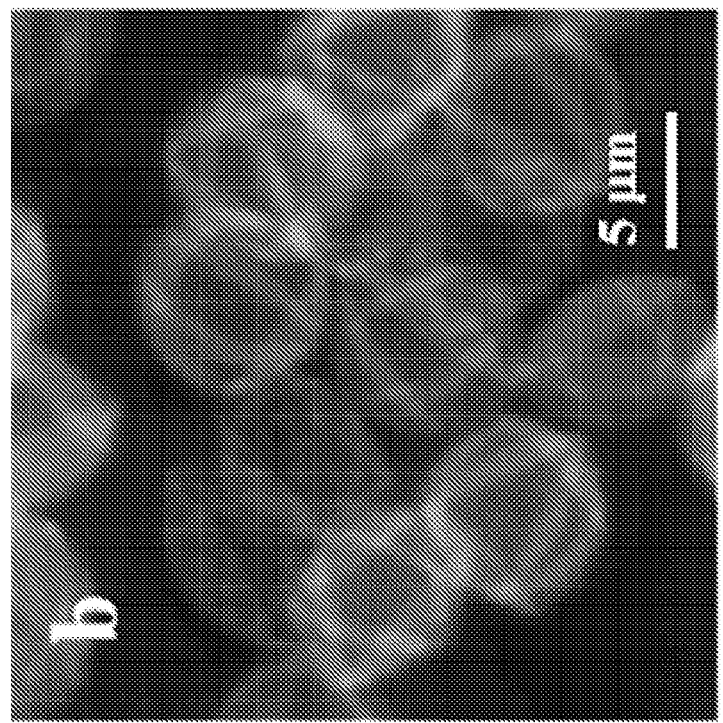
FIGS. 19A-B: Confocal fluorescence images of (A) hollow capsules of Alg(PPB/SAF)$_4$ obtained by removal of the templated MF cores (4.34 micron diameter) by treatment with HCl acid and (B) air-dried hollow capsules of Alg(PPB/SAF)$_4$.
Figure 19A:
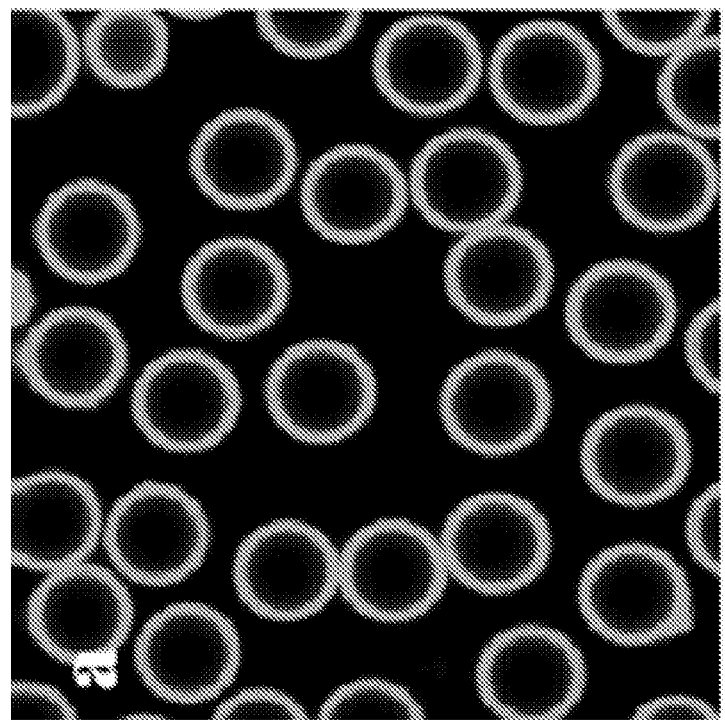

Although our initial interest was to use biotin-PEG grafted PLL as a means to functionalize the outer film surface, we observed that hollow capsules could be obtained when PPB was used as a multilayer building block along with avidin, despite the strong steric hindrance of PEG. In solution PPB/SAF hollow capsules typically maintain the spherical shape of the template particle (FIG. 19A). After air-drying, hollow capsules clearly reveals a number of folds and creases due to their collapse (FIG. 19B). The shells are also flattened and some spreading is noticed; the diameters (both short- and long-axis) of the shells are larger than that of the MF particle. This increase in diameter is ascribed to a combination of drying and the forces exerted on the shells upon their immobilization onto glass substrates (Angew. Chem. Int. Ed. 37 (1998) 2202). The shells also exhibit a somewhat rough surface texture. This may be characteristic of the polymer film.

Figure 20B:
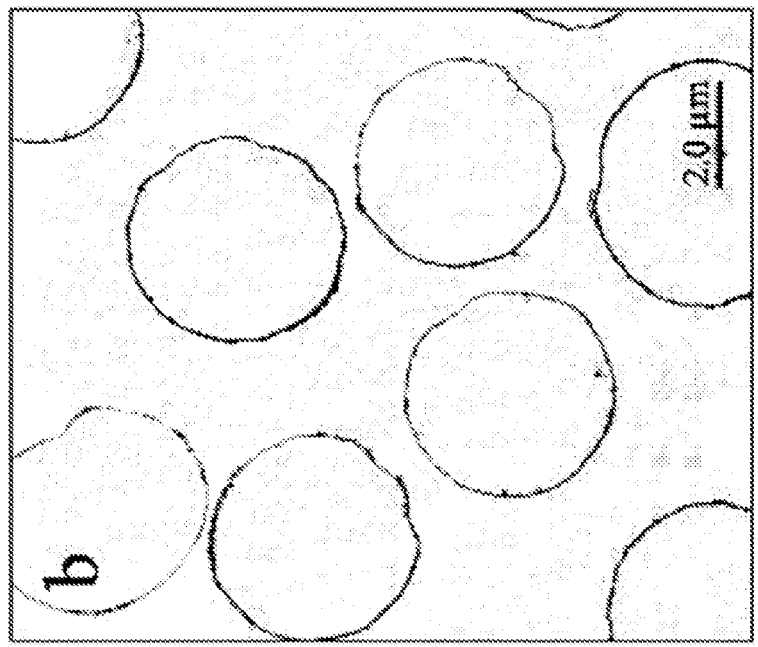
FIGS. 20A-B: TEM image of nine-layer hollow capsules of (A) Alg(PB/SAF)$_4$ and (B) Alg(PPB/SAF)$_4$ produced by templating on MF particles (4.34 micron diameter).
Figure 20A:
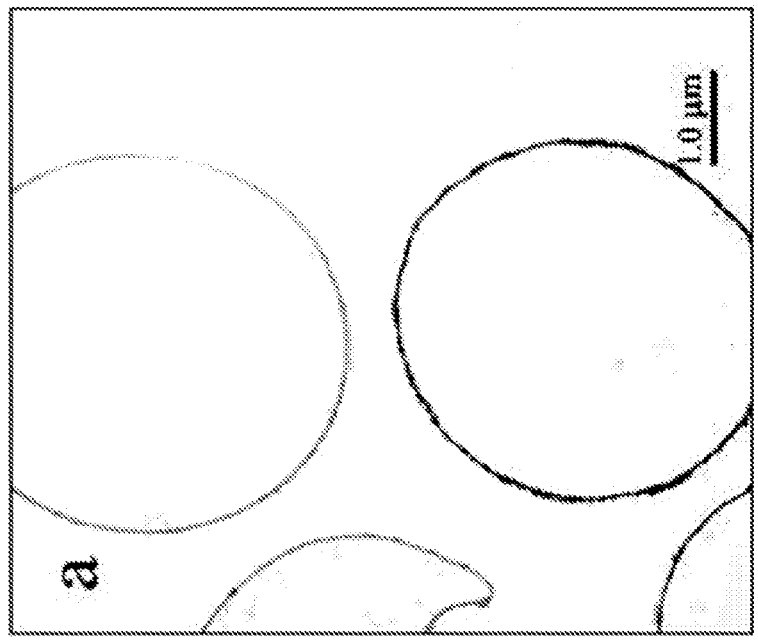

The wall structure of nine-layer hollow capsules of Alg(PB/SAF)$_4$ and Alg(PPB/SAF)$_4$ was further examined by TEM (FIG. 20). The stained polymeric shell surrounding the liquid interior can be clearly identified. Some invaginations are noted, but are likely caused by the embedding technique. Apart from some longitudinal deformation, the hollow capsules are almost spherical in shape, which is also observed in the CLSM images. The homogeneous curvature of the shells proves that, provided the interior liquid has not been removed, the fabricated shells preserve both the diameter and the spherical shape of the template particles. In contrast, creases and folds seen in the CLSM pictures are due to bending and tension forces exerted on the polymeric shell upon drying. Notably the outer surface of the polymer film is seen to be rough, and there is no evidence of a distinct layered structure to the film. In addition, the TEM image does not provide any evidence of existing holes larger than a few nanometers in the polymeric shells. From the TEM image the wall thickness can also be deduced. Interestingly, no difference is observed in the capsule wall thickness within the resolution of the TEM measurements for these two systems, despite the differences in molecular structures between PB and PPB. Both Alg(PB/SAF)$_4$ and Alg(PPB/SAF)$_4$ have wall thicknesses on the order of 50 nm. Thus, we speculate that the PEG layer is in a flattened or mushroom conformation in the Alg(PPB/SAF)$_4$ capsule wall. Otherwise, Alg(PPB/SAF)$_4$ capsule would be expected to possess greater wall thickness than Alg(PB/SAF)$_4$. A single polyelectrolyte layer thickness is reported to be ca. 1.5-2 nm (Langmuir 16 (2000) 4059; Biomacromolecules, 2 (2001) 921). Hence, the thickness for the five polyelectrolyte layers (one Alg layer and four PB or PPB layers) is approximately 7-10 nm. The molecular dimensions of avidin are reported to be 6.0×5.5×4.0 nm. Therefore, it is feasible to suggest that approximately 2 layers of FITC-streptavidin are adsorbed onto the surface of colloidal particles with each deposition, which would yield wall thickness of 50 nm. This conclusion is in good agreement with the aforementioned absorbance data.

It should be noted that FITC labeled (strept)avidin was applied to form fluorescent layers on the surface of flat substrates and colloidal particles only for observation with confocal fluorescence microscopy. FITC alone does not play a role in the formation of such multilayer architectures since hollow capsules have also been obtained with the FITC-free streptavidin and PB (data not shown). Moreover, hollow capsules were not obtained when PLL without conjugated biotin was used, in part, due to the electrostatic repulsion between FITC-avidin and PLL and the absence of any interaction between FITC-streptavidin and PLL.

Overall, the microscopy data provide unambiguous evidence that multilayer hollow biocapsules with PEG chains embedded inside walls have been successfully created by the LbL strategy. The bioaffinity between (strept)avidin and biotin is strong enough to overcome the steric repulsive effects of the PEG chains.

Hollow capsule stability was examined in a hyperosmolar salt solution. PPB/SAF capsules were found to decompose when exposed to 5 M NaCl for 12 h. In contrast, PB/SAF capsules were stable upon exposure to 5 M NaCl concentrations over a several day period. The difference in behavior between these two types of capsules is most likely related to swelling of the PEG chains, which may lead to disruption of the multiplayer. Nonetheless, decomposable hollow capsules may be utilized to activate the release of encapsulated compounds for certain applications.

Pegylated multilayered architectures have been created by a layer-by-layer deposition of (strept)avidin and biotinylated PLL through avidin/biotin complexation, despite electrostatic repulsion arising from the net positive charge of both avidin and PLL and the steric hindrance of PEG chains. To extend the colloid-templated LbL technique and the family of capsules, novel hollow biocapsules have been constructed by using a sacrificial core as a template onto which multilayers are assembled via avidin/biotin affinity and not by conventional electrostatic interaction. Both the UV-vis absorbance and TEM wall thickness data suggest that approximately two layers of FITC-streptavidin are adsorbed onto the surface with each deposition. In contrast, multilayered architectures were not formed when unmodified PLL was used in place of biotin-labeled PLL. Significantly, use of avidin-enzyme or avidin-antibody conjugates, as well as other biotinylated polymers containing unique functional groups provides additional opportunities to enhance coating bioactivity and functionality, including site specific targeting.

Transplantation of islets microencapsulated within a membrane-mimetic barrier. Evaluation of cell viability. Initial experiments used CHO cells as a readily available model system to assess cell viability after encapsulation. Cells were suspended into alginate solution at $6 \times 10^6$ cells/mL and then coated with a photopolymerized membrane-mimetic lipid film. Cell viability of >95% at 24 and 48 hours was confirmed using a Live/Dead cell assay (Molecular Probes, Inc.). In the next phase of this effort, we determined the viability of encapsulated rat islets (103). Rat islets were isolated from outbred male Wistar rats and suspended at a concentration of 1000 islets in 0.25 mL of 2% alginate (UP LVM, Pronova Biomedical, Norway). Alginate encapsulated islets were coated with a membrane-mimetic film and after overnight culture viability was graded with respect to the proportion of viable cells within a given islet. As described elsewhere, we determined that the addition of two anti-apoptotic agents, nicotinamide (10 mM) and Z-VAD.fmk (40 µM), were important adjuncts for maximizing islet viability (103, 104). Overall, viability of rat islets after an additional coating with a membrane-mimetic thin film compared favorably with viability measurements obtained on islets coated with a multilayer of alginate/PLL alone.

Figure 22A:
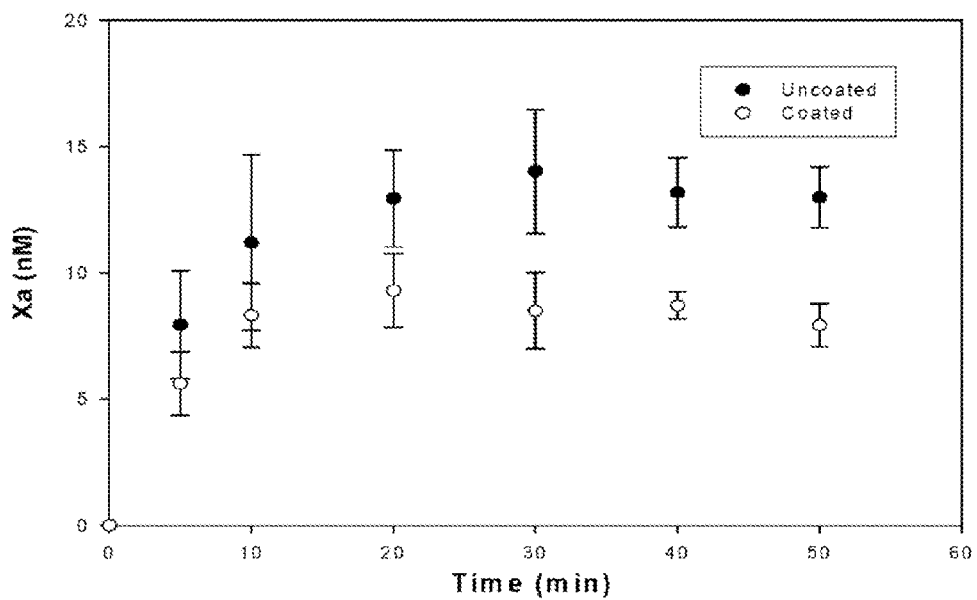
FIGS. 22A-B: Human islets coated with a shape-conforming barrier have reduced Factor Xa production. (A) shows Xa concentration as a function of time with respect to test groups each containing 3,000 islet equivalents. (B) shows Xa concentration as a function of time normalized to nanograms of islet DNA.
Figure 22B:
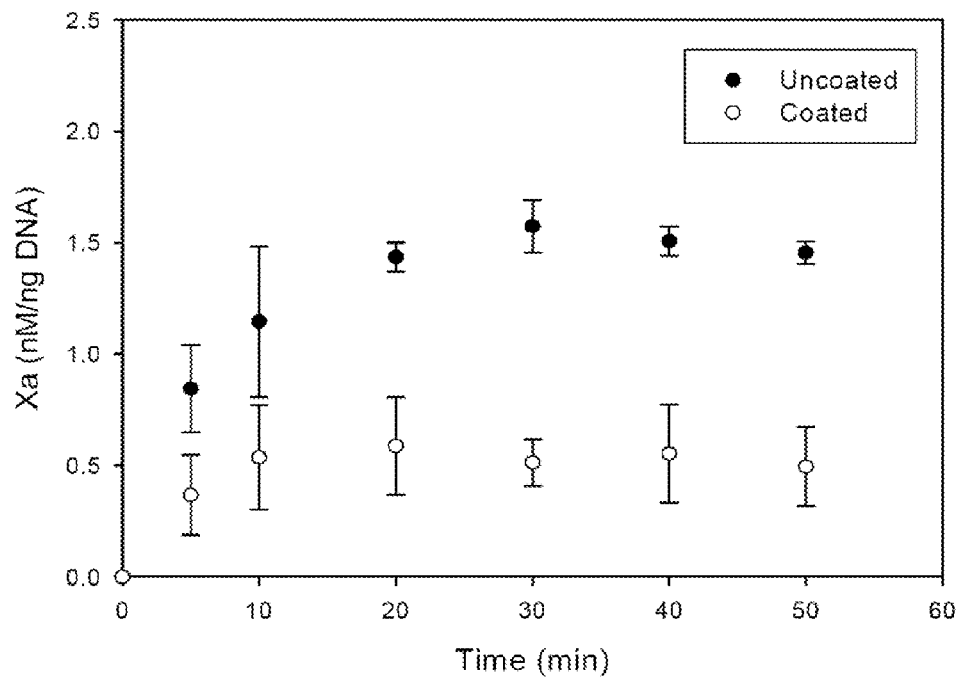

Islet viability is also preserved after direct coating with a conformal polymer barrier. Porcine islets (PI) viability has been assessed using a Live/Dead cell assay (Molecular Probes, Inc.) before and after conformal coating with an alginate/protamine multilayer $(Pro/Alg)_3$. Viability was graded using a previously published classification scheme (Hubbell and colleagues. Biotechnol Bioeng 1998;57(6):655-65). In vitro islet viability was 84% prior to coating and 85% after coating and is summarized in Table 4.

human islets significantly reduces the generation of Factor Xa, which is the rate-limiting step in thrombin production. Specifically, cadaveric human islets were coated with a conformal barrier consisting of an alginate and PLL multilayer, as described hereinabove. Both uncoated and coated islets were prepared and divided into samples each containing 3000 islet equivalents, which were incubated in a 2 mL reaction volume containing FactorX (160 nM), Factor VIIa (10 nM), and $Ca^{2+}$ (2 mM) at 37° C. At timed intervals, 20 µL of the above mixture was aliquoted, quenched with 364 µL of 20 mM EDTA, and 16 µL of the chromogenic substrate S-2222 (0.2 mM final) was added. Measurement of Factor Xa was performed using UV-VIS spectroscopy and Xa concentration was calculated from a standard curve. The data are presented as Xa generation over time with respect to both coated and uncoated groups (FIG. 22). As is evident, a conformal barrier substantially reduces Xa production. Indeed, when the data are corrected for differences in islet mass, as expressed in terms of nanograms of DNA, Xa production was three-fold higher in uncoated islets ($p<0.005$, $n=3$).

Figure 23:
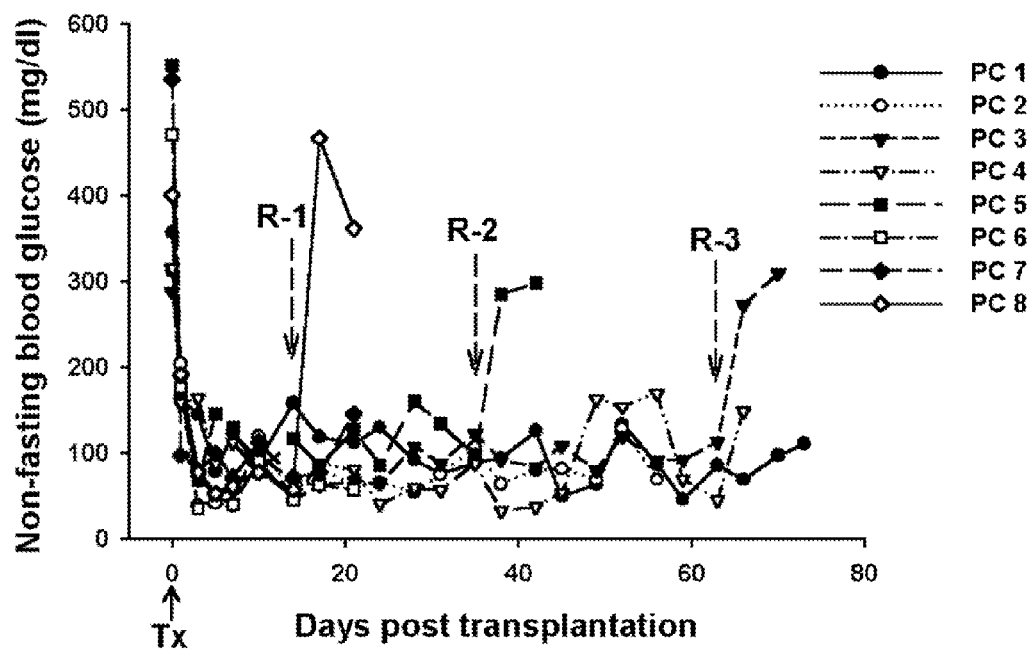
FIG. 23: Non-fasting blood glucose levels in diabetic NOD/SCID mice transplanted with rat islets encapsulated in membrane-mimetic coated alginate microbeads. Prolonged euglycemia was observed for periods exceeding 2 months and intentional removal of islets (R-1, R-2, R-3) confirmed that insulin production was due to transplanted islets.

Transplantation of rat islets encapsulated in a membrane-mimetic thin film. Evaluation of in vivo viability and islet function. Long-term islet viability and function were assessed by transplantation into streptozotocin-treated NOD/SCID mice ($n=8$) (103). Approximately 1000 rat islets were transplanted into the peritoneal cavity and non-fasting blood glucose was assessed every other day during the first week and twice weekly thereafter. In vivo transplantation revealed that non-fasting blood glucose levels declined to normal (<150 mg/dL) within 24 hours after transplantation in all recipients and remained within the normal range in all mice with the longest observed time point currently 73 days (FIG. 23). Intentional graft removal at 17, 35, and 63 days (labeled R-1, R-2 and R-3, respectively) after transplantation induced recurrence of diabetes, confirming that insulin production was solely due to transplanted islets (FIG. 23).

All references throughout this application, for example patent documents including issued or granted patents or

TABLE 4

| | (Pro-ALG)3 PI | | | | | | Naked PI | | | | |
|---|---|---|---|---|---|---|---|---|---|---|---|
| | <100 | 100-200 | >200 | Sum | Viability | | <100 | 100-200 | >200 | Sum | Viability |
| A | 6 | 28 | 0 | 34 | 46% | A | 10 | 33 | 1 | 44 | 52% |
| B | 4 | 24 | 3 | 31 | 42% | B | 4 | 22 | 6 | 32 | 38% |
| C | 1 | 6 | 2 | 9 | 12% | C | 1 | 5 | 2 | 8 | 10% |
| D | 0 | 0 | | 0 | 0% | D | 0 | 0 | | 0 | 0% |
| E | | | | | 0% | E | | | | | 0% |
| Sum | 11 | 58 | 5 | 74 | 100% | Sum | 15 | 60 | 9 | 84 | 100% |
| | 15% | 78% | 7% | 100% | | | 18% | 71% | 11% | 100% | |
| | Viability evaluated with Hubbell's method | | | | | | Viability evaluated with Hubbell's method | | | | |
| | 83.4% | | | | | | 85.7% | | | | |

Figure 21A:
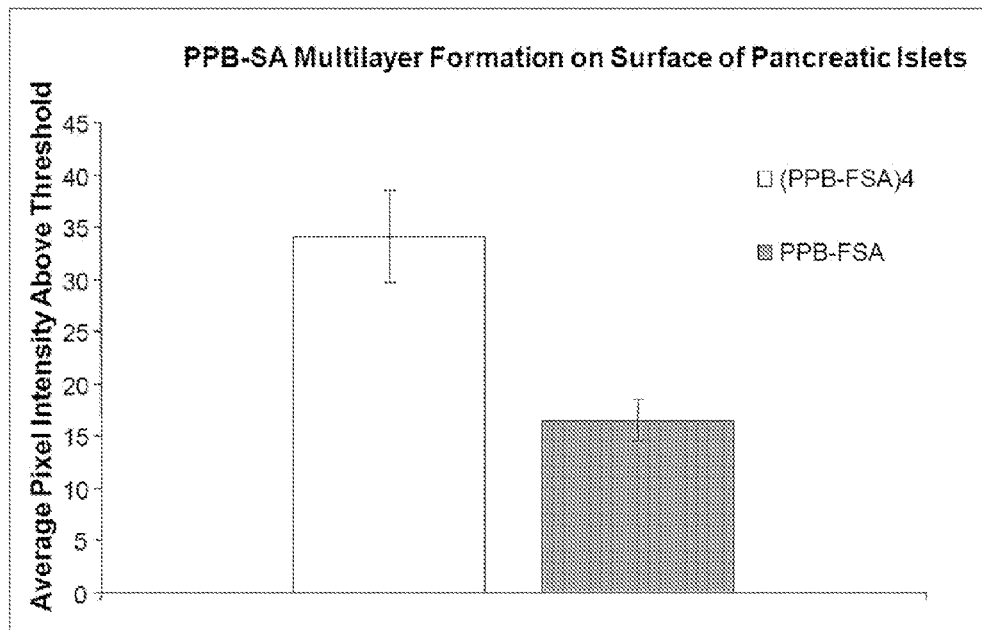
FIGS. 21A-B: (A) Image analysis of confocal fluorescent microscopic images of PPB—SA coated pancreatic islet cells revealed greater fluorescent intensity for four FITC-labeled layers compared to cells composed of a single layer. (B) Islet viability was not significantly different between the (PPB—SA)$_4$ coated islet cells and uncoated islet cells.
Figure 21B:
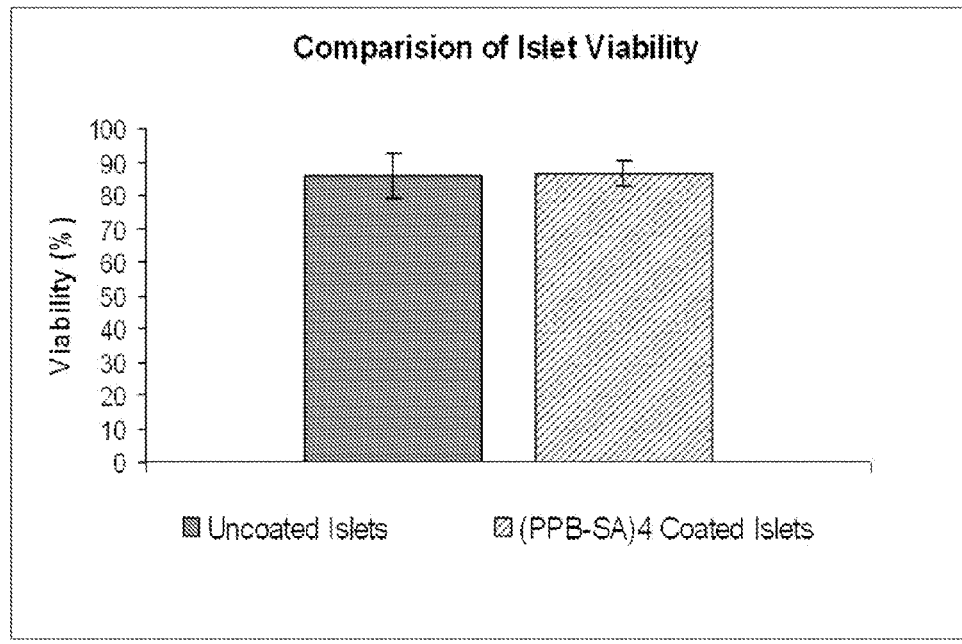

Islet viability is maintained on pancreatic islets coated with $(PPB-SA)_4$ films (FIG. 21). FIG. 21A shows that islets coated with four FITC layers $(PPB-SA)_4$ have a significantly greater fluorescent intensity than those composed of a single layer (PPB-FSA). Coating did not affect islet viability (FIG. 21B).

The expression of tissue factor on pancreatic islets provides at least one known proinflammatory/prothrombotic trigger that may be present after intraportal islet transplantation. A conformal islet barrier can limit access of islet associated tissue factor to blood borne coagulation factors. We have confirmed that the presence of a conformal barrier on equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

Prior work by inventors hereof includes U.S. patent application Ser. No. 09/149,098 filed Sep. 8, 1998, provisional application No. 60/058,194 filed Sep. 8, 1997, provisional application Nos. 60/091,399 and 60/101,252 filed Jun. 30, 1998 and Sep. 21, 1998, respectively, provisional application No. 60/197,072 filed Apr. 13, 2000, provisional application 60/221,618 filed Jul. 28, 2000, provisional application No. 60/198,792 filed Apr. 20, 2000 and 60/221,828 filed Jul. 28, 2000, PCT application US01/12094 filed Apr. 13, 2001, and PCT application No. US01/12918 filed Apr. 20, 2001, PCT application 97/16080 filed Apr. 11, 1997, application Ser. No. 08/729,928 filed Oct. 15, 1996, Ser. No. 09/342,922 filed Jun. 30, 1999, Ser. No. 09/149,098 filed Sep. 8, 1998, Ser. No. 10/257,805 filed Apr. 15, 2003, Ser. No. 10/343,408 filed Jul. 22, 2003, U.S. Pat. No. 6,171,614 issued Jan. 9, 2001, U.S. Pat. No. 6,071,532 issued Jun. 6, 2000, U.S. Pat. No. 5,741,325 issued Apr. 21, 1998, and U.S. Pat. No. 4,906,465 issued Mar. 6, 1990.

REFERENCES

1. Rayhill S C, Heimes M, Kirk A D, Sollinger H W. Simultaneous pancreas-kidney transplantation: Recent experience at the University of Wisconsin. Exp Clin Endocrin Diabetes 1996;104:353-9.
2. Remuzzi G, Ruggenenti P, Mauer S. Pancreas and kidney/pancreas transplants: Experimental medicine or real improvement? Lancet 1994;343:27-31.
3. Warnock G, Rajotte R. Human pancreatic islet transplantation. Transplantation Reviews 1992;6:195-208.
4. Ao Z, Korbutt G S, Warnock G L, Flashner M, Colby C B, Rajotte R V. Microencapsulation enhances canine islet survival during long-term culture. Transplantation Proceedings 1995;27:3350-1.
5. Lacy P. Status of islet cell transplantation. Diabetes Rev 1993;1:76-92.
6. Korbutt G S, Ao Z, Warnock G L, Flashner M, Rajotte R V. Successful reversal of diabetes in nude mice by transplantation of microencapsulated porcine neonatal islet aggregates. Transplantation Proceedings 1995;27:3212-2.
7. Halle J P, Bourassa S, Leblond F A, Chevalier S, Beaudry M, Chapdelaine A, et al. Protection of islets of Langerhans from antibodies by microencapsulation with alginate-poly-L-lysine membranes. Transplantation 1993;44:350-4.
8. Colton C, Avgoustiniatos E. Bioengineering in the development of the hybrid artificial pancreas. J Biochem Eng 1991;113:152-70.
9. Colton C K. The engineering of xenogeneic islet transplantation by immunoisolation. Diab Nutr Metabol 1992;5(145-9).
10. Sun Y, Ma X, Zhou D, Vacek I, Sun A M. Normalization of diabetes in spontaneously diabetic cynomolgus monkeys by xenografts of microencapsulated porcine islets without immunosuppression. J Clin Invest 1996;98:1417.
11. Peterson J D, Haskins K. Transfer of diabetes in the NOD-scid mouse by CD4 T-cell clones: Differential requirement for CD8 T-cells. Diabetes 1996;45:328-36.
12. Haskins K, McDuffe M. Acceleration of diabetes in young NOD mice with CD4+ islet-specific T cell clone. Science 1990;249:1433-6.
13. Jarpe A, Hickman M, Anderson J. Flow cytometric enumeration of mononuclear cell populations infiltrating the islets of Langerhans in prediabetic NOD mice: Development of model of autoimmune insulititis for Type I diabetes. Regional Immunology 1990;3:305-17.
14. Miller B, Appel M, O'Neil J, Wicker L. Both the Lyt-2+ and L3T4+ T cell subsets are required for the transfer of diabetes in nonobese diabetic mice. J Immunol 1988;140:52-8.
15. Akita K, Ogawa M, Mandel T. Effect of FK506 and anti-CD4 therapy on fetal pig pancreas xenografts and host lymphoid cells in NOD/Lt, CBA, and BALB/c mice. Cell Transplantation 1994;3:61-73.
16. Gill R, Wolf L, Daniel D, Coulombe M. CD4+ T cells are both necessary and sufficient for islet xenograft rejection. Transp Proc 1994;26(12034).
17. Loudovaris T, Charlton B, Mandel T. The role of T cells in the destruction of xenografts within cell impermeable membranes. Transplantation Proceedings 1992;24:2938-9.
18. Pierson R, Winn H, Russell P, Auchincloss H. CD4 positive lymphocytes play a dominant role in murine xenogeneic responses. Transplantation Proceedings 1989;21:519-21.
19. Parker W, Saadi S, Lin S S, Holzknecht Z E, Bustos M, Platt J L. Transplantation of discordant xenografts: A challenge revisited. Immunology Today 1996;17:373-8.
20. Weber C J, Zabinsi S, Koschitzky T, Rajotte R, Wicker L, Peterson L, et al. Microencapsulated dog and rat islet xenografts into streptozotocin-diabetic and NOD mice. Horm Metab Res 1990;35:219-226.
21. Takeuchi T, Lowry R, Konoieczny B. Heart allografts in murine systems. Transplantation 1992;53:1281-94.
22. Moses R, Winn H, Auchincloss H. Xenogeneic proliferation and lymphokine production are dependent upon CD4+ helper T cells and self antigen-presenting cells in the mouse. J Exp Med 1990;172:567-75.
23. Lenschow D J, Zeng Y, Thistlethwaite J R, Montag A, Brady W, Gibson M G, et al. Long-term survival of xenogeneic pancreatic islet grafts induced by CTLA41g. Science 1992;257:789-95.
24. Frank M. The role of complement in inflammation and phagocytosis. Immunol Today 1991;12:322-6.
25. Bretzel R G, Brandhorst D, Brandhorst H, Eckhard M, Ernst W, Friemann S, et al. Improved survival of intraportal pancreatic islet cell allografts in patients with type-1 diabetes mellitus by refined peritransplant management. J Mol Med 1999;77:140-143.
26. Shapiro A M, Lakey J R, Ryan E A, Korbutt G S, Toth E, Warnock G L, et al. Islet transplantation in seven patients with type 1 diabetes mellitus using a glucocorticoid free immunosuppressive regimen. N Engl J Med 2000;343::230-38.
27. Hirshberg B, Rother K I, Harlan D M. Islet transplantation: Where do we stand now? Diabetes Metab Res Rev 2003;19(3):175-8.
28. Mattsson G, Jansson L, Carlsson P O. Decreased vascular density in mouse pancreatic islets after transplantation. Diabetes 2002;51:1362-6.
29. Kaufman D B, Platt J L, Rabe F L, Dunn D L, Bach F H, Sutherland D E. Differential roles of Mac-1+ cells, and CD4+ and CD8+ T lymphocytes in primary nonfunction and classic rejection of islet allografts. J Exp Med 1990; 172(1):291-302.
30. Liu X, Hering B J, Mellert J, Brandhorst D, Brandhorst H, Federlin K, et al. Prevention of primary nonfunction after porcine islet allotransplantation. Transplantation Proceedings 1997;29:2701-2072.
31. Deng S, Ketchum R J, Kucher T, Weber M, Naji A, Brayman K L. Primary nonfunction of islet xenografts in rat recipients results from non T-cell mediated immune responses. Transplant. Proc. 1997;29:1726.
32. Brandhorst D, Brandhorst H, Zwolinski A, Nahidi F, Jahr H, Bretzel R G. Primary nonfunction is not caused by accelerated rejection after pig-to-rat islet transplantation. Transplant. Proc. 1998;30:407.

33. Tan M, Di Carlo A, Liu S Q, Tector A J, Tchervenkov J I, Metrakos P. Hepatic sinusoidal endothelium upregulates IL-1alpha, IFN-gamma, and iNOS in response to discordant xenogeneic islets in an in vitro model of xenoislet transplantation. J Surg Res 2002;102:229-36.
34. Berney T, Molano R D, Cattan P, Pileggi A, Vizzardelli C, Oliver R, et al. Endotoxin-mediated delayed islet graft function is associated with increased intra-islet cytokine production and islet cell apoptosis. Transplantation 2001; 71:125-32.
35. Vargas F, Vives-Pi M, Somoza N, Armengol P, Alcalde L, Marti M, et al. Endotoxin contamination may be responsible for the unexplained failure of human pancreatic islet transplantation. Transplantation 1998;65:722-727.
36. Bennet W, Sundberg B, Groth C G. Incompatibility between human blood and isolated islets of Langerhans: A finding with implications for clinical intraportal islet transplantation? Diabetes 1999;48:1907-14.
37. Moberg L, Johansson H, Lukinius A, Berne C, Foss A, Kallen R, et al. Production of tissue factor by pancreatic islet cells as a trigger of detrimental thrombotic reactions in clinical islet transplantation. Lancet 2002;360(9350):2039-45.
38. Ozmen L, Ekdahl K N, Elgue G, Larsson R, Korsgren O, Nilsson B. Inhibition of thrombin abrogates the instant blood-mediated inflammatory reaction triggered by isolated human islets: Possible application of the thrombin inhibitor melagatran in clinical islet transplantation. Diabetes 2002;51(6):1779-84.
39. Froberg M K, Leone J P, Jessurun J, Sutherland D E. Fatal disseminated intravascular coagulation after autologous islet transplantation. Hum Pathol 1997;28:1295-98.
40. Shapiro A M, Lakey J R, Rajotte R V. Portal vein thrombosis after transplantation of partially purified pancreatic islets in a combined human liver/islet allograft. Transplantation 1995;59:1060-63.
41. McGilvray I D, Rotstein O D. Role of the coagulation system in the local and systemic inflammatory response. World J Surgery 1998;22:179-86.
42. Cicala C, Cirino G. Linkage between inflammation and coagulation: An update on the molecular basis of the crosstalk. Life Sciences 1998;62:1817-24.
43. Coughlin S R. Thrombin signalling and protease-activated receptors. Nature 2000;407:258-64.
44. Bottino R, Fernandez L A, Ricordi C, Lehmann R, Tsan M F, Oliver R, et al. Transplantation of allogeneic islets of Langerhans in the rat liver: Effects of macrophage depletion on graft survival and microenvironment activation. Diabetes 1998;47:316-23.
45. Tibell L A, Sethson I, Buevich A V. Characterization of the heparin-binding domain of human extracellular superoxide dismutase. Biochim Biophys Acta 1997;1340:21-32.
46. Edens R E, Linhardt R J, Bell C S, Weiler J M. Heparin and derivatized heparin inhibit zymosan and cobra venom factor activation of complement in serum. Immunopharmacology 1994;27:145-53.
47. Maillet F, Petitou M, Choay J, Kazatchkine M D. Structure-function relationships in the inhibitory effect of heparin on complement activation: Independency of the anticoagulant and anti-complementary sites on the heparin molecule. Mol Immunology 1988;25:917-923.
48. Sahu A, Pangburn M K. Identification of multiple sites of interaction between heparin and the complement system. 1993:679-684.
49. Owen W G, Esmon C T. Functional properties of an endothelial cell cofactor for thrombin-catalyzed activation of protein C. J Biol Chem 1981;256(11):5532-5.
50. Esmon C T, Owen W G. Identification of an endothelial cell cofactor for thrombin-catalyzed activation of protein C. Proceedings of the National Academy of Sciences of the United States of America 1981;78(4):2249-52.
51. Esmon N L, Owen W G, Esmon C T. Isolation of a membrane-bound cofactor for thrombin-catalyzed activation of protein C. Journal of Biological Chemistry 1982; 257(2):859-64.
52. Esmon C T, Gu J M, Xu J, Qu D, Stearns-Kurosawa D J, Kurosawa S. Regulation and functions of the protein C anticoagulant pathway. Haematologica 1999;84(4):363-8.
53. Esmon C T, Ding W, Yasuhiro K, Gu J M, Ferrell G, Regan L M, et al. The protein C pathway: New insights. Thrombosis & Haemostasis 1997;78(1):70-4.
54. Esmon N L, Carroll R C, Esmon C T. Thrombomodulin blocks the ability of thrombin to activate platelets. J Biol Chem 1983;258(20):12238-42.
55. Hancock W W, Bach F H. Immunobiology and therapeutic applications of protein C/protein S/thrombomodulin in human and experimental allotransplantation and xenotransplantation. Trends Cardiovasc Med 1997;7:174-183.
56. Grey S T, Hancock W W. A physiologic anti-inflammatory pathway based on thrombomodulin expression and generation of activated protein C by human mononuclear phagocytes. J Immunol 1996;156(6):2256-63.
57. Grey S T, Tsuchida A, Hau H, Orthner C L, Salem H H, Hancock W W. Selective inhibitory effects of the anticoagulant activated protein C on the responses of human mononuclear phagocytes to LPS, IFN-gamma, or phorbol ester. J Immunol 1994;153(8):3664-72.
58. Blakely M L, Van der Werf W J, Berndt M C, Dalmasso A P, Bach F H, Hancock W W. Activation of intragraft endothelial and mononuclear cells during discordant xenograft rejection. Transplantation 1994;58(10):1059-66.
59. Grinnell B W, Hermann R B, Yan S B. Human protein C inhibits selectin-mediated cell adhesion: Role of unique fucosylated oligosaccharide. Glycobiology 1994;4:221-226.
60. Esmon C T. The anticoagulant and anti-inflammatory roles of the protein C anticoagulant pathway. J Autoimmunity 2000;15:113-6.
61. Marcus A, Broekman M, Drosopoulos J, Pinsky D, Islam N, Gayle R, 3rd, et al. Thromboregulation by endothelial cells: Significance for occlusive vascular diseases. Arterioscler Thromb Vasc Biol 2001;21(2):178-82.
62. Linden J. Molecular approach to adenosine receptors: Receptor-mediated mechanisms of tissue protection. Annu Rev Pharmacol Toxicol 2001;41:775-87.
63. Koziak K, Sevigny J, Robson S C, Siegel J B, Kaczmarek E. Analysis of CD39/ATP diphosphohydrolase (ATPDase) expression in endothelial cells, platelets and leukocytes. Thromb Haemost 1999;82(5):1538-44.
64. Kaczmarek E, Koziak K, Sevigny J, Siegel J B, Anrather J, Beaudoin A R, et al. Identification and characterization of CD39/vascular ATP diphosphohydrolase. J Biol Chem 1996;271(51):33116-22.
65. Imai M, Kaczmarek E, Koziak K, Sevigny J, Goepfert C, Guckelberger O, et al. Suppression of ATP diphosphohydrolase/CD39 in human vascular endothelial cells. Biochemistry 1999;38(41):13473-9.
66. Marcus A J, Broekman M J, Drosopoulos J H, Islam N, Alyonycheva T N, Safier L B, et al. The endothelial cell ecto-ADPase responsible for inhibition of platelet function is CD39. J Clin Invest 1997;99(6):1351-60.
67. Marcus A J, Broekman M J, Drosopoulos J H, Pinsky D J, Islam N, Maliszewski C R. Inhibition of platelet recruitment by endothelial cell CD39/ecto-ADPase: Significance for occlusive vascular diseases. Ital Heart J 2001;2(11): 824-30.
68. Qawi I, Robson S C. New developments in anti-platelet therapies: Potential use of CD39/vascular ATP diphosphohydrolase in thrombotic disorders. Curr Drug Targets 2000;1(3):285-96.
69. Imai M, Takigami K, Guckelberger O, Lin Y, Sevigny J, Kaczmarek E, et al. CD39/vascular ATP diphosphohydrolase modulates xenograft survival. Transplant Proc 2000; 32(5):969.
70. Kaneider N C, Egger P, Dunzendorfer S, Noris P, Balduini C L, Gritti D, et al. Reversal of thrombin-induced deactivation of CD39/ATPDase in endothelial cells by HMG-COA reductase inhibition: Effects on Rho-GTPase and adenosine nucleotide metabolism. Arterioscler Thromb Vasc Biol 2002;22(6):894-900.
71. Decher G. Fuzzy nanoassemblies: Toward layered polymeric multicomposites. Science 1997;277:1232-1237.
72. Dai Z, Voigt A, Donath E, Möhwald H. Novel encapsulated functional dye particles based on alternately adsorbed multi-layers of active oppositely charged macromolecular species. Macromol Rapid Commun 2001;22:756-762.
73. Dai Z, Dähne L, Donath E, Möhwald H. Downhill energy transfer of multichromophores in layer-by-layer self-assembling light-harvesting capsules. J Phys Chem 2002; 106:11501-11508.
74. Dai Z, Dahne L, Möhwald H, Tiersch B. Novel capsules with high stability and controlled permeability. Angew Chem Int Ed 2002;41:4019-4022.
75. Dai Z, Möhwald H. Highly stable and biocompatible Nafion-based capsules with controlled permeability for low molecular species. Chem Eur J 2002;8:4751-4755.
76. Dai Z, Voigt A, Leporatti S, Donath E, Dahne L, Möhwald H. Layer-by-layer self-assembly of polyelectrolyte and low molecular weight species into capsules. Adv Mater 2001;13:1339.
77. Voigt A, Lichtenfeld H, Sukhorukov G B, Zastrow H, Donath E, Baumler H, et al. Membrane filtration for microencapsulation and microcapsules fabrication by layer-by-layer polyelectrolyte adsorption. Ind. Eng. Chem. Res. 1999;38(4037).
78. Neu B, Voigt A, Mitlohner R, Leporatti S, Gao CY, Donath E, et al. Biological cells as templates for hollow microcapsules. J Microencapsulation 2001;18:385.
79. Leporatti S, Voigt A, Mitlohner R, Sukhorukov GB, Donath E, Mohwald H. Scanning force microscopy investigation of polyelectrolyte nano- and microcapsule wall texture. Langmuir 2000;16:4059.
80. Seifert K, Fendler K, Bamberg E. Charge transport by ion translocating membrane proteins on solid supported membranes. Biophys J 1993;64:384-391.
81. Spinke J, Yang J, Wolf H, Liley M, Ringsdorf H, Knoll W. Polymer-supported bilayer on a solid substrate. Biophys J 1992;63:1667-1671.
82. Florin E L, Gaub H E. Painted supported lipid membranes. Biophys J 1993;64:375-383.
83. Orban J, Chaikof E L. Cytomimetic biomaterials. 4. In-situ photopolymerization of phospholipids on an alkylated surface. Macromolecules 2000.
84. Liu H, Orban J, Chaikof E L. Generation of a photopolymerized membrane mimetic monolayer on an alginate/poly-L-lysine coacervate. Polymer Preprints 2000;41:1036-37.
85. Chon J H, Marra K G, Chaikof E L. Cytomimetic biomaterials. 3. Preparation and transport studies of an alginate/amphiphilic copolymer/polymerized phospholipid film. J Biomater Sci Polymer Ed 1999;10:95-108.
86. Perez-Salas U A, Faucher K, Majkrzak C F, Berk N F, Chaikof E L, Krueger S. Characterization of a biomimetic polymeric lipid bilayer by phase sensitive neutron reflectometry. Langmuir 2003;19:7688-7694.
87. Liu H, Faucher K M, Sun X-L, Feng J, Orban J M, Chon J H, et al. A supported lipid bilayer as a membrane-mimetic cell encapsulation barrier. Langmuir 2002;18:1332-1339.
88. Faucher K M, Sun X L, Chaikof E L. Fabrication and characterization of glycocalyx-mimetic surfaces. Langmuir 2003;19:1664-1670.
89. Sun L, Chaikof E L. The synthesis of neoglycophospholipid conjugates via an improved reductive amination of w-oxoalklyglycosides and phosphatidylethanolamines. Carbohydrate Res 1998;370:77-81.
90. Sun X-L, Liu H, Sun L, Orban J M, Chaikof E L. Synthesis and terminal functionalization of polymerizable phosphatidylethanolamine. Bioconjug Chem 2001;12:673-677.
91. Feng J, Tseng P-Y, Faucher K M, Orban J M, Sun X-L, Chaikof E L. Functional reconstitution of thrombomodulin within a substrate supported membrane-mimetic polymer film. Langmuir 2002;18:9907-0013.
92. Sun X L, Faucher K M, Houston M, Grande D, Chaikof E L. Design and synthesis of biotin chain-terminated glycopolymers for surface glycoengineering. J Am Chem Soc 2002;124(25):7258-9.
93. Holland N B, Qiu Y, Ruegsegger M, Marchant R E. Biomimetic engineering of non-adhesive glycocalyx-like surfaces using oligosaccharide surfactant polymers. Nature 1998;392(6678):799-801.
94. Ruegsegger M A, Marchant R E. Reduced protein adsorption and platelet adhesion by controlled variation of oligomaltose surfactant polymer coatings. J Biomed Mater Res 2001;56(2):159-167.
95. Sun X-L, Faucher K M, Chaikof E L. Cytomimetic biomaterials: Fabrication, characterization, and applications. In: Dillow A K, Lowman T, editors. Biomimetic Materials and Design: Marcel Dekker; 2002. p. 139-158.
96. Chon J H, Mara K G, Chaikof E L. Cytomimetic Biomaterials. 3. Preparation and transport studies of an alginate/amphiphilic copolymer/polymerized phospholipid film. J Biomat Sci Polymer Ed 1999;10(95-108).
97. Chaikof E L. Engineering and materials considerations in islet cell transplantation. Ann Rev Biomed Eng 1999;1: 103-127.
98. Chaikof E L, Safely S, Weber C J. Microencapsulation methods: Alginate-poly(L-lysine). In: Atala A, Lanza R P, editors. Methods of Tissue Engineering: Academic Press; 2002. p. 803-808.
99. Rele S, Hou S, Chaikof E L. Design and characterization of novel carbohydrate terminated polyethylene oxide dendrimers. In review Organic Letters 2003.
100. Taton D, Saule M, Logan J, Duran R, Hou S, Chaikof E L, et al. Synthesis of functionalized multiarm poly(ethylene oxide) stars. Polymer 2003;44:5067-5074.
101. Taton D, Saule M, Logan J, S. H, Chaikof E L, Gnanou Y. Polymerization of ethylene oxide using a calixarene-based precursor: Synthesis of eight arm poly(ethylene oxide) stars by the core-first methodology. J Polymer Science: Part A: Polymer Chemistry 2003;41:1669-1676.
102. Hou S, Chaikof E L, Taton D, Gnanou Y. Synthesis of water-soluble star-block and dendrimer-like copolymers based on poly(ethylene oxide) and poly(acrylic acid). Macromolecules 2003;36:3874-3881.

103. Cui W, Barr G, Faucher K M, Safley S, Weber C J, Chaikof E L. A membrane-mimetic barrier for xenogeneic islet encapsulation. Transplantation Proceedings 2003.

104. Cui W, Barr G, Faucher K, Chaikof E. A novel approach for islet encapsulation with bio-membrane mimetic system. Transplantation 2003;76:146.

105. Marra K C, Winger T M, Hanson S R, Chaikof E L. Cytomimetic biomaterials. 1. In-situ polymerization of phospholipids on an alkylated surface. Macromolecules 1997;30:6483-6487.

106. Conboy J C, Liu S C, O'Brien D F, Saavedra S S. Planar supported bilayer polymers formed from bis-diene lipids by Langmuir-Blodgett deposition and UV irradiation. Biomacromolecules 2003;4:841-849.

107. Ross E E, Rozanski L J, Spratt T, Liu S C, O'Brien D F, Saavedra S S. Planar supported lipid bilayer polymers formed by vesicle fusion. 1. Influence of diene monomer structure and polymerization method on film properties. Langmuir 2003;19:1752-1765.

108. Ross E E, Spratt T, Liu S C, Rozanski L J, O'Brien D F, Saavedra S S. Planar supported lipid bilayer polymers formed by vesicle fusion. 2. Adsorption of bovine serum albumin. Langmuir 2003;19:1766-1774.

109. Cruise G M, Hegre O D, Scharp D S, Hubbell J A. A sensitivity study of the key parameters in the interfacial photopolymerization of poly(ethylene glycol) diacrylate upon porcine islets. Biotechnol Bioeng 1998;57(6):655-65.

110. Cruise G M, Hegre O D, Lamberti F V, Hager S R, Hill R, Scharp D S, et al. In vitro and in vivo performance of porcine islets encapsulated in interfacially photopolymerized poly(ethylene glycol) diacrylate membranes. Cell Transplant 1999;8(3):293-306.

111. Hill R S, Cruise G M, Hager S R, Lamberti F V, Yu X, Garufis C L, et al. Immunoisolation of adult porcine islets for the treatment of diabetes mellitus. The use of photopolymerizable polyethylene glycol in the conformal coating of mass-isolated porcine islets. Ann N Y Acad Sci 1997; 831:33243.

112. Ziani-Cherif H, Imachi K, Matsuda T. Preparation of aryldiazonium-, aryldiazo-, and arylazido-derivatized copolymers and their surface photografting. Macromolecules 1999;32:3428-3447.

113. Feng J, Chaikof E L. Reconstitution of thrombomodulin into polymerizable phospholipid vesicles. Polymer Preprints 2000;41:1653-1654.

114. Espana F, Zuazu I, Vicente V, Estelles A, Marco P, Aznar J. Quantification of circulating activated protein C in human plasma by immunoassays—enzyme levels are proportional to total protein C levels. Thromb Haemost 1996; 75(1):56-61.

115. Gruber A, Griffin J H. Direct detection of activated protein C in blood from human subjects. Blood 1992;79 (9):2340-8.

116. Ames B N. Methods Enzymol 1966;8:115-117.

117. Anzai J, Tomonori H, Nobuyuki N. Construction of multilayer thin films containing avidin by a layer-by-layer deposition of avidin and poly(anion). Langmuir 2000;1 6(6306-6311).

118. Weiler-Guettler H, Christie P D, Beeler D L, Healy A M, Hancock W W, Rayburn H, et al. A targeted point mutation in thrombomodulin generates viable mice with a prethrombotic state. J Clin Invest 1998;101 (9):1983-91.

119. Clayton H, London N, Colloby P, Bell P, James R. The effect of capsule composition on the biocompatibility on the biocompatibility of alginate-poly-l-lysine capsules. J Microencapsulation 1991;8:221-233.

120. Weber C, Ayres-Price J, Costanzo M, Stall A. NOD mouse peritoneal cellular response to poly-L-lysine-alginate microencapsulated rat islets. Transplantation Proceedings 1994;26:1116-1119.

121. Segal H C, Hunt B J, Gilding K. The effects of alginate and nonalginate wound dressings on blood coagulation and platelet activation. J Biomater Appl 1998; 12:249-57.

122. Keurena J F W, Wieldersb S J H, Willems G M, Morrac M, Cahaland L, Cahaland P, et al. Thrombogenicity of polysaccharide-coated surfaces. Biomaterials 2003;24: 1917-1924.

123. Forrester J V, Wilkinson P C. Inhibition of leukocyte locomotion by hyaluronic acid. J Cell Sci 1981;48:315-331.

124. Riches D W H. Macrophage involvement in wound repair, remodeling, and fibrosis. In: Clark RAF, editor. The Molecular and Cellular Biology of Wound Repair. New York: Plenum Press; 1996. p. 95-142.

125. Wilbur D S, Pathare P M, Hamlin D K, Stayton P S, To R, Klumb L A, et al. Development of new biotin:streptavidin reagents for pretargeting. Biomolecular Engineering 1999;16:113-118.

126. Mahal L K, Yarema K J, Bertozzi C R. Engineering chemical reactivity on cell surfaces through oligosaccharide biosynthesis. Science 1997;276:1125-1128.

127. Sampson N S, Mrksich M, Bertozzi C R. Surface molecular recognition. Proc Nat Acad Sci (USA) 2001;98: 12870-12871.

128. Neuenschwander P F, Fiore M M, Morrissey J H. Factor VII autoactivation proceeds via interaction of distinct protease-cofactor and zymogen-cofactor complexes. Implications of a two-dimensional enzyme kinetic mechanism. J Biol Chem 1993;268(29):21489-92.

129. Skelland A H P. Diffusional Mass Transfer. New York: John Wiley & Sons, Inc.; 1974.

130. Crooks C A, Douglas J A, Broughton R L, Sefton M V. Microencapsulation of mammalian cells in a HEMA-MMA copolymer: Effects on capsule morphology and permeability. J Biomed Mater Res 1990;24:1241-1262.

131. Goossens P L, Jouin H, Marchal G, Milon G. Isolation and flow cytometric analysis of the free lymphomyeloid cells present in murine liver. J Immunol Methods 1990; 132:137.

132. Hardy C L, Bhathal P S, Snibson K J, Adams T E. Comparison of intrahepatic lymphocytes from normal and growth hormone transgenic mice with chronic hepatitis and liver cancer. Immunology 1997;90:412-420.

133. Contreras J L, Bilbao G, Smyth C A, Eckhoff D E, Jiang X L, Jenkins S, et al. Cytoprotection of pancreatic islets before and early after transplantation using gene therapy. Kidney Int Suppl 2002;61 Suppl 1:79-84.

134. Hogan K A, Weiler H, Lord S T. Mouse models in coagulation. Thromb Haemost 2002;87(4):563-74.

135. Bennet W, Sundberg B, Groth C G, Brendel M D, Brandhorst D, Brandhorst H, et al. Incompatibility between human blood and isolated islets of Langerhans: a finding with implications for clinical intraportal islet transplantation? Diabetes 1999;48(10):1907-14.

136. Petaja J, Fernandez J A, Gruber A, Griffin J H. Anticoagulant synergism of heparin and activated protein C in vitro. Role of a novel anticoagulant mechanism of heparin, enhancement of inactivation of factor V by activated protein C. J Clin Invest 1997;99(11):2655-63.

137. Kume M, Hayashi T, Yuasa H, Tanaka H, Nishioka J, Ido M, et al. Bacterial lipopolysaccharide decreases thrombomodulin expression in the sinusoidal endothelial cells of 137. ...rats—a possible mechanism of intrasinusoidal microthrombus formation and liver dysfunction. J Hepatol 2003; 38(1):9-17.
138. Terada Y, Eguchi Y, Nosaka S, Toba T, Nakamura T, Shimizu Y. Capillary endothelial thrombomodulin expression and fibrin deposition in rats with continuous and bolus lipopolysaccharide administration. Lab Invest 2003;83(8): 1165-73.
139. Arai M, Mochida S, Ohno A, Ogata I, Obama H, Maruyama I, et al. Blood coagulation equilibrium in rat liver microcirculation as evaluated by endothelial cell thrombomodulin and macrophage tissue factor. Thromb Res 1995;80(2):113-23.
140. Mochida S, Arai M, Ohno A, Yamanobe F, Ishikawa K, Matsui A, et al. Deranged blood coagulation equilibrium as a factor of massive liver necrosis following endotoxin administration in partially hepatectomized rats. Hepatology 1999;29(5): 1532-40.
141. Lindhout T, Blezer R, Schoen P, Willems G M, Fouache B, Verhoeven M, et al. Antithrombin activity of surface-bound heparin studied under flow conditions. J Biomed Mater Res 1995;29(10):1255-66.
142. Blezer R, Willems G M, Cahalan P T, Lindhout T. Initiation and propagation of blood coagulation at artificial surfaces studied in a capillary flow reactor. Thrombosis & Haemostasis 1998;79(2):296-301.
143. Gomi K, Zushi M, Honda G, Kawahara S, Matsuzaki O, Kanabayashi T, et al. Antithrombotic effect of recombinant human thrombomodulin on thrombin-induced thromboembolism in mice. Blood 1990;75(7):1396-9.
144. Taoka Y, Okajima K, Uchiba M, Johno M. Neuroprotection by recombinant thrombomodulin. Thromb Haemost 2000;83(3):462-8.
145. Uchiba M, Okajima K, Murakami K, Johno M, Mohri M, Okabe H, et al. rhs-TM prevents ET-induced increase in pulmonary vascular permeability through protein C activation. Am J Physiol 1997;273(4 Pt 1):L889-94.
146. Uchiba M, Okajima K, Murakami K, Johno M, Okabe H, Takatsuki K. Recombinant thrombomodulin prevents endotoxin-induced lung injury in rats by inhibiting leukocyte activation. Am J Physiol 1996;271(3 Pt 1):L470-5.
147. Brummel K E, Butenas S, Mann K G. An integrated study of fibrinogen during blood coagulation. J Biol Chem 1999;274(32):22862-70.
148. Rand M D, Lock J B, van't Veer C, Gaffney D P, Mann K G. Blood clotting in minimally altered whole blood. Blood 1996;88(9):343245.
149. Langston H P, Ke Y, Gewirtz A T, Dombrowski K E, Kapp J A. Secretion of IL-2 and IFN-gamma, but not IL4, by antigen-specific T cells requires extracellular ATP. J Immunol 2003;170(6):2962-70.
150. Di Virgilio F, Chiozzi P, Ferrari D, Falzoni S, Sanz J M, Morelli A, et al. Nucleotide receptors: An emerging family of regulatory molecules in blood cells. Blood 2001;97(3): 587-600.
151. Fan C, Zwacka R M, Engelhardt J F. Therapeutic approaches for ischemia/reperfusion injury in the liver. J Mol Med 1999;77(8):577-92.
152. Link A A, Kino T, Worth J A, McGuire J L, Crane M L, Chrousos G P, et al. Ligand-activation of the adenosine A2a receptors inhibits IL-12 production by human monocytes. J Immunol 2000;164(1):43642.
153. Weber C J, Kapp J, Hagler M, Safley S, Chryssochoos J, Chaikof E L. Long-term survival of poly-L-lysine-alginate microencapsulated islet xenografts in spontaneously diabetic NOD mice. In: Lanza R, Chick W, editors. Handbook of Cell Encapsulation Technology. New York: Springer-Verlag; 1999. p.117-137.
154. Balamurugan A N, Gu Y, Tabata Y, Miyamoto M, Cui W, Hori H, et al. Bioartificial pancreas transplantation at pre-vascularized intermuscular space: effect of angiogenesis induction on islet survival. Pancreas 2003;26(3):279-85.
155. Cui W, Kim D H, Imamura M, Hyon S H, Inoue K. Tissue-engineered pancreatic islets: Culturing rat islets in the chitosan sponge. Cell Transplant 2001;10(4-5):499-502.
156. Gu Y, Tabata Y, Kawakami Y, Balamurugan A N, Hori H, Nagata N, et al. Development of a new method to induce angiogenesis at subcutaneous site of streptozotocin-induced diabetic rats for islet transplantation. Cell Transplant 2001; 10(4-5):453-7.
157. Kawakami Y, Iwata H, Gu Y, Miyamoto M, Murakami Y, Yamasaki T, et al. Modified subcutaneous tissue with neovascularization is useful as the site for pancreatic islet transplantation. Cell Transplant 2000;9(5):729-32.
158. Gu Y J, Miyamoto M, Cui W X, Xu B Y, Kawakami Y, Yamasaki T, et al. Effect of neovascularization-inducing bioartificial pancreas on survival of syngeneic islet grafts. Transplant Proc 2000;32(7):2494-5.
159. Cui W, Gu Y, Miyamoto M, Tanaka M, Xu B, Imamura M, et al. Novel method for isolation of adult porcine pancreatic islets with two-stage digestion procedure. Cell Transplant 1999;8(4):391-8.
160. Miyamoto M, Inoue K, Hoki M, Gu Y J, Cui W X, Ohyanagi H. Effect of "acidic oxidative potential water" on microbial contamination harvesting porcine pancreas for islet xenotransplantation. Transplant Proc 1998;30(7):3431-2.
161. Yamasaki T, Inoue K, Hayashi H, Gu Y, Setoyama H, Ida J, et al. Effect of a new immunosuppressive agent, FTY720, on survival of islet allografts. Cell Transplant 1998;7(4):403-6.
162. Miyamoto M, Inoue K, Gu Y, Tun T, Cui W, Fujiwara I, et al. Improved large-scale isolation of breeder porcine islets: possibility of harvesting from nonheart-beating donor. Cell Transplant 1998;7(4):397-402.
163. Gu Y J, Inoue K, Miyamoto M, Cui W X, Tanaka M, Setoyama H, et al. Improvement of adult porcine pancreatic islet isolation; employment of an innovative enzyme solution. Transplant Proc 1998;30(2):356-7.

We claim:

1. A method for coating a living cell surface with a shape-conforming barrier, said method comprising the steps of:
   a. providing an isolated living cell having a surface; and
   b. conformally coating the cell surface with a shape-conforming barrier layer, wherein the layer comprises a negatively charged polymer and a positively charged polymer so that the charged polymers electrostatically interact within the layer,
   wherein there is a plurality of layers, and wherein one layer is an outermost layer and at least one polymer layer comprises photoactive groups for forming interlayer covalent bonds.

2. The method of claim 1, wherein there is between three or more layers and ten or less layers.

3. The method of claim 1, further comprising coating the outermost layer with a film selected from the group consisting of a membrane-mimetic film, a charged polymer, and a charged avidin-containing polymer.

4. The method of claim 1, wherein the negatively charged polymer is alginate.

5. The method of claim 1, wherein the positively charged polymer is protamine or poly-L-lysine.

6. The method of claim 1, wherein the barrier further comprises one or more bioactive agents selected from the group consisting of an anticoagulant agent and an anti-inflammatory agent.

7. The method of claim 6, wherein the bioactive agent is selected from the group consisting of thrombomodulin, heparin and CD39.

8. The method of claim 1, wherein the living cell is selected from the group consisting of islets, insulin secreting cells, genetically engineered cells designed to secrete bioactive compounds, neurons, cardiac myoblasts, myocardial cells, chondrocytes, and dopamine secreting cells.

9. A method for coating a living cell surface with a shape-conforming barrier, said method comprising the steps of:
   a. providing an isolated living cell having a surface; and
   b. conformally coating the cell surface with a shape-conforming barrier layer, wherein the layer comprises a negatively charged polymer and a positively charged polymer so that the charged polymers electrostatically interact within the layer, wherein there is a plurality of layers, wherein one layer is an outermost layer and wherein the polymers within a layer are bound by one or more of electrostatic, covalent, or non-covalent interaction.

10. The method of claim 9 where, the non-covalent interaction is a biotin-streptavidin interaction.

11. The method of claim 9, wherein there is between three or more layers and ten or less layers.

12. The method of claim 9, further comprising coating the outermost layer with a film selected from the group consisting of a membrane-mimetic film, a charged polymer, and a charged avidin-containing polymer.

13. The method of claim 9, wherein the negatively charged polymer is alginate.

14. The method of claim 9, wherein the positively charged polymer is protamine or poly-L-lysine.

15. The method of claim 9, wherein the barrier further comprises one or more bioactive agents selected from the group consisting of an anticoagulant agent and an anti-inflammatory agent.

* * * * *